United States Patent [19]

Goto et al.

[11] Patent Number: 4,943,314
[45] Date of Patent: * Jul. 24, 1990

[54] PYRIDINE-3-CARBOXAMIDE DERIVATIVES HAVING PLANT GROWTH INHIBITING ACTIVITY

[75] Inventors: Yukihisa Goto; Kazuhisa Masamoto; Hiroshi Yagihara, all of Himeji; Yasuo Morishima, Kobe; Hirokazu Osabe, Himeji, all of Japan

[73] Assignee: Daicel Chemical Industries, Ltd., Osaka, Japan

[ * ] Notice: The portion of the term of this patent subsequent to Feb. 12, 2005 has been disclaimed.

[21] Appl. No.: 318,818

[22] Filed: Mar. 3, 1989

Related U.S. Application Data

[62] Division of Ser. No. 922,038, Oct. 20, 1986, Pat. No. 4,844,732.

[30] Foreign Application Priority Data

Oct. 24, 1985 [JP] Japan .................................. 60-238524

[51] Int. Cl.$^5$ .................. C07D 211/84; C07D 211/86; C07D 211/90; A01N 43/40
[52] U.S. Cl. ........................................ 71/94; 546/156; 546/261; 546/283; 546/291; 546/298; 546/112
[58] Field of Search ..................... 546/298, 291; 71/94

[56] References Cited

U.S. PATENT DOCUMENTS 4,777,256 10/1988 Ueda et al. ........................... 546/291

Primary Examiner—Alan L. Rotman
Attorney, Agent, or Firm—Bryan, Cave, McPheeters & McRoberts

[57] ABSTRACT

A compound of the formula (I)

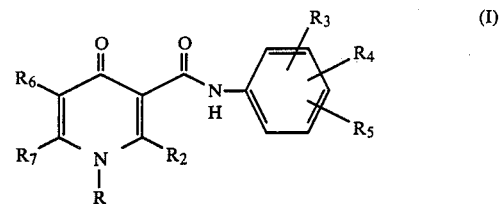

or a salt thereof, wherein R is hydrogen atom, phenyl group which may be substituted freely or a group of —(CH$_2$)$_n$—R$_1$ wherein n is an interger from 1 to 3 and R$_1$ is hydrogen atom, hydroxy group, lower alkoxy group, mercapto group, lower alkylthio group, amino group, di-lower alkylamino group, C$_{3-11}$ alkyl group, lower alkenyl group, lower alkynyl group, cycloalkyl group, 5- or 6-membered heterocyclic group, or phenyl group which may be substituted by one or two substituents of halogen, lower alkyl or lower alkoxy;

R$_2$ and R$_7$ are different, hydrogen atom, C$_{1-11}$ alkyl group, lower alkenyl group, lower alkylyl group, cycloalkyl group, lower alkoxyalkyl group, lower alkylthioalkyl group, phenyl group which may be substituted freely, aralkyl group whose nucleus may be subsituted by one or two substituents of halogen, lower alkyl or lower alkoxy or haloalkyl group or 5- or 6-membered heterocyclic group;

R$_3$, R$_4$ and R$_5$ are, the same or different, hydrogen atom, halogen atom, cyano group, nitro group, amino group, lower alkyl group, lower haloalkyl group, hydroxy group, lower alkoxy group, aryloxy group, carboxy group or lower alkoxycarbonyl group;

R$_6$ is hydrogen atom, halogen atom, lower alkyl group, phenyl group which may be substituted freely or aralkyl group which may be substituted freely; or R$_6$ and R$_7$ may be combined to form a group of —(CH$_2$)$_m$— (m is 3 or 4), which is useful e.g., a plant growth inhibitor.

12 Claims, No Drawings

PYRIDINE-3-CARBOXAMIDE DERIVATIVES HAVING PLANT GROWTH INHIBITING ACTIVITY

This is a divisional of U.S. application Ser. No. 922,038, filed Oct. 20, 1986, now U.S. Pat. No. 4,844,732.

BACKGROUND OF THE INVENTION

1. Field of the Invention

This invention relates to novel compounds which belong to 1,4-dihydro-4-oxo-3-pyridinecarboxamides. The compounds of this invention show growth inhibitory activities on plants and also antiinflammatory activity.

2. Description of the Prior Arts

Some compounds belonging to 1,4-dihydro-4-oxo-3-pyridinecarboxamides are found in literatures.

In Bull. Acad. Pol. Sci., Ser. Sci. Chim. 23(11), 901 (1975), Zankowska-Jasinska. W. et al., reported on N-(4-chlorophenyl)-1,4-dihydro-4-oxo-1,2,6-triphenyl-3-pyridinecarboxamide and 1-(4-chlorophenyl)-1,4-dihydro-4-oxo-N,2,6-triphenyl-3-pyridinecarboxamide. In Zesz. Nauk. Uniw. Jagiellon., Pr. Chim, 21., 141 (1976), Zankowska-Jasinska. W. et al., reported on 1,4-dihydro-4-oxo-N,2,6-triphenyl-3-pyridinecarboxamide, 1,4-dihydro-4-oxo-N,1,2,6-tetraphenyl-3-pyridinecarboxaminde, 1,4-dihydro-2,6-dimethyl-4-oxo-N,1-diphenyl-3-pyridinecarboxamide.

In Yakugakuzassi, 101, 40 (1981), Kato et al. reported on four compounds, namely N-(4-chlorophenyl)-1,4-dihydro-2,6-dimethyl-4-oxo-3-pyridinecarboxamide, 1,4-dihydro-2,6-dimethyl-4-oxo-N-phenyl-1-(phenylmethyl)-3-pyridinecarboxamide, 1,4-dihydro-N-(4-methoxyphenyl)-2,6-dimethyl-4-oxo-1-(phenylmethyl)-3-pyridinecarboxamide and N-(4-chlorophenyl)-1,4-dihydro-2,6-dimethyl-4-oxo-1-(phenylmethyl)-3-pyridinecarboxamide, as one of the studies on reactivity of ketene derivatives but they did not refer to utility thereof. Canadian Pat. No. 1,115,278 [and also J. B. Pierce et al, J. Med. Chem. 25, 131 (1982)], there are disclosed 4-pyridone compounds possessing antiinflammatory activity, i.e., 1,4-dihydro-2,6-dimethyl-4-oxo-N,1-diphenyl-3-pyridinecarboxamide, N,1-dibutyl-1,4-dihydro-2,6-dimethyl-4-oxo-3-pyridinecarboxamide, N,1-didodecyl-1,4-dihydro-2,6-dimethyl-4-oxo-3-pyridinecarboxamide, N-(4-chlorophenyl)-1-ethyl-1,4-dihydro-2,6-dimethyl-4-oxo-3-pyridinecarboxamide, etc.

Cephalosporins which contain a partial structure of 1,4-dihydro-4-oxo-3-pyridinecarboxamide are known as medicine in Japanese Patent Unexamined Publication Nos. Sho 54(1979)-24892, Sho 51(1976)-43783 and Sho 51(1976)-48686.

On the other hand, 1,4-dihydro-4-oxo-3-pyridinecarboxylic acid derivatives as compounds which show plant growth regulating activity, especially chemical hybridizing activity, are known in Japanese Patent Unexamined Publication Nos. Sho 52(1977)-144676 (see also U.S. Pat. No. 4,051,142) and Sho 57(1982)-114,573 (see also E. P. 40,082). However, plant growth inhibitory agents whose active ingredients are 1,4-dihydro-4-oxo-3-pyridinecarboxamide as in the formula (I) shown below are not known.

SUMMARY OF THE INVENTION

This invention provides compounds of the formula (I) and salts thereof.

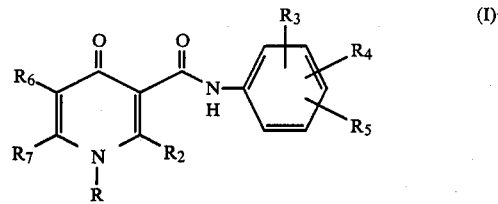

or a salt thereof wherein R is hydrogen atom, phenyl group which may be substituted freely or a group of —$(CH_2)_n$—$R_1$ wherein n is an integer from 1 to 3 and $R_1$ is hydrogen atom, hydroxy group, lower alkoxy group, mercapto group, lower alkylthio group, amino group, di-lower alkylamino group, $C_{3-11}$ alkyl group, lower alkenyl group, lower alkynyl group, cycloalkyl group, 5- or 6-membered heterocyclic group, or phenyl group which may be substituted by one or two substituents of halogen, lower alkyl or lower alkoxy;

$R_2$ and $R_7$ are different, hydrogen atom, $C_{1-11}$ alkyl group, lower alkenyl group, lower alkynyl group, cycloalkyl group, lower alkoxyalkyl group, lower alkylthioalkyl group, phenyl group which may be substituted freely, aralkyl group whose nucleus may be substituted by one or two substituents of halogen, lower alkyl or lower alkoxy or haloalkyl group or 5- or 6-membered heterocyclic group;

$R_3$, $R_4$ and $R_5$ are, the same of different, hydrogen atom, halogen atom, cyano group, nitro group, amino group, lower alkyl group, lower haloalkyl group, hydroxy group, lower alkoxy group, aryloxy group, carboxy group or lower alkoxycarbonyl group;

$R_6$ is hydrogen atom, halogen atom, lower alkyl group, phenyl group which may be substituted freely or aralkyl group which may be substituted freely; or $R_6$ and $R_7$ may be combined to form a group of —$(CH_2)_m$— (m is 3 or 4).

This invention also provides plant growth inhibitors which contain at least one kind of compounds of the formula (I) and salts thereof as active ingredient.

DESCRIPTION OF PREFERRED EMBODIMENTS

The term of "lower" used for lower alkyl, lower alkoxy or like group in this invention means a group containing 1–5 carbon atoms. Specifically, there may be mentioned as lower alkyl group methyl, ethyl propyl, isopropyl, butyl, isobutyl, pentyl or isopentyl; as lower alkoxy group methoxy, ethoxy, propoxy, isopropoxy or butoxy; as lower alkoxycarbonyl group methoxycarbonyl, ethoxycarbonyl, propoxycarbonyl or butoxycarbonyl; or as lower alkylthio group methylthio, ethylthio, propylthio, isopropylthio, butylthio or pentylthio. As lower alkenyl or lower alkynyl group may be mentioned vinyl, allyl, isopropenyl 2-butenyl, 1,3-butadienyl, 2-pentenyl, 1,4-pentadienyl, 1,6-heptadienyl, 1-hexenyl, ethynyl or 2-propynyl.

Examples of cycloalkyl group include cyclopropyl, cyclopentyl and cyclohexyl.

Examples of haloalkyl group include trifluoromethyl, chloromethyl and the like.

Examples of lower alkoxyalkyl group include methoxymethyl, ethoxymethyl, propoxymethyl, butoxymethyl and the like.

Examples of lower alkylthioalkyl group include methylthiomethyl, ethylthiomethyl, methylthioethyl, ethylthioethyl and the like.

Halogen atom includes chlorine, bromine, fluorine and iodine atom.

Examples of aralkyl group include benzyl, 3-phenylpropyl, 4-phenylbutyl and the like.

Examples of aryloxy group include phenyloxy, naphtyloxy and the like.

5- or 6-Membered heterocyclic group includes 5- or 6-membered one containing one to three hetero atoms selected from nitrogen atom, oxygen atom and sulfur atom. The examples of the 5-membered heterocyclic group are furyl, tetrahydrofuryl, thienyl, thiazolyl, isothiazolyl, oxazolyl, isooxazolyl or pyrazolyl and the 6-membered heterocyclic group are pyridyl, pyrimidinyl, pyrazinyl or pyridazinyl. These heterocyclic groups may be substituted by alkyl as methyl or ethyl, halogen atom or phenyl. When the heterocyclic group is substituted by phenyl, it may form a condensed ring combining the two adjacent carbon atoms in the heterocyclic group with phenyl group. Examples of the condensed ring are benzothiazolyl, benzofuryl, quinazolinyl or quinoxalinyl group.

Examples of substituent of phenyl group and aralkyl group which may be substituted freely include halogen atom, lower alkyl, lower alkoxy, trihaloalkyl, nitro, cyano and the like, and as numbers of the substituents one or two is preferable.

The compound of the formula (I) in this invention may form an addition salt with an acid such as hydrochloric acid, sulfuric acid, phosphoric acid, methanesulfonic acid, p-toluenesulfonic acid or trifluoroacetic acid when sufficiently basic, and also form a salt with an inorganic base when it contains a carboxylic group. Such salts are also included in this invention.

The compound of the formula (I) in this invention may be prepared by any of the following methods.

(METHOD A)

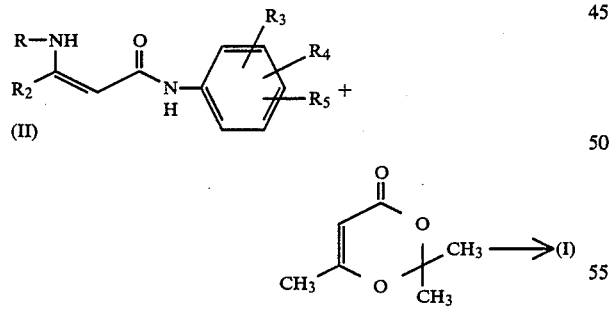

[R, $R_2$, $R_3$, $R_4$ and $R_5$ of the formula (II) are the same as those in the formula (I).]

This method comprises reacting a 3-aminoacrylic acid anilide derivative (II) or its tautomer with 2,2,6-trimethyl-4H-1,3-dioxin-4-one in an appropriate solvent (e.g., toluene or xylene) under heating at a temperature of e.g., 100° C.–140° C. 2-Ethyl-2,6-dimethyl-4H-1,3-dioxin-4-one is also useful in place of 2,2,6-trimethyl-4H-1,3-dioxin-4-one. Also, in this method, 3-aminoacrylic acid anilide derivative (II) is not necessarily required to be in its isolated form but may be in the form of the crude reaction mixture of an amine of the formula (III) with a compound of the formula (IV)

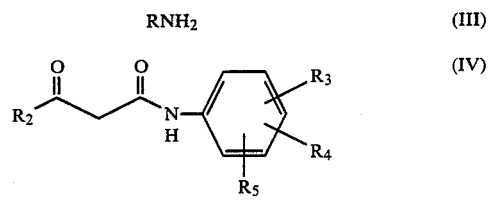

[R, $R_2$, $R_3$, $R_4$ and $R_5$ in the formula (III) and (IV) are the same as those in the formula (I).]

For the practical purpose it is convenient to use the crude reaction mixture as such (METHOD B)

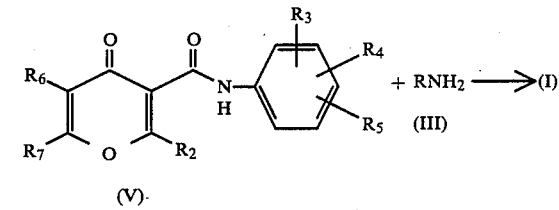

[R, $R_2$, $R_3$, $R_4$, $R_5$, $R_6$ and $R_7$ in the formula (III) and (V) are the same as those in the formula (I).]

This method comprises reacting a 4-pyrone compound (V) corresponding to the formula (I), i.e., 4-oxo-N-phenyl-4H-pyran-3-carboxamide with ammonia or an amine of the formula (III) or a salt thereof in an appropriate solvent (e.g., ethanol or water) at a temperature from room temperature to about 50° C. The amount of ammonia or the amine employed is equimolecular or more to the 4-pyrone compound or a large excess if needed. When the aine is used as its available salt, it is required to convert to its free form by addition of an organic or an inorganic base in an amount needed for neutralization or more.

(METHOD C)

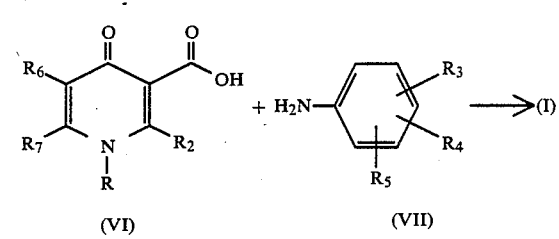

[R, $R_2$, $R_3$, $R_4$, $R_5$, $R_6$ and $R_7$ in the formula (VI) and (VII) are the same meaning as defined in the formula (I).]

This method comprises reacting a carboxylic acid corresponding to the formula (I), i.e., 1,4-dihydro-4-oxo-3-pyridinecarboxylic acid derivative (VI) with an aniline derivative (VII) in the presence of a condensing agent for dehydration. It is advantageous to use as the condensing agent for dehydration 1-substituted-2-halopyridinium salt and a tertiary amine according to the method described in e.g., Japanese Patent Unexamined Publication No. Sho 52(1977)-57102.

(METHOD C')

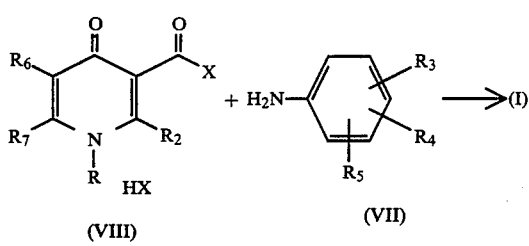

[R, R$_2$, R$_3$, R$_4$, R$_5$, R$_6$ and R$_7$ in the formula (VII) and (VII) are the same meaning as defined in the formula (I), and X is halogen atom.]

This method comprises reacting an acid halide (VIII) prepared easily by the reaction of (VI) and halogenating agent such as thionyl chloride with an aniline derivative (VII) in the presence of a base.

(METHOD D)

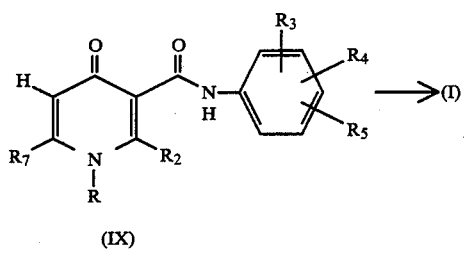

[R, R$_2$, R$_3$, R$_4$, R$_5$ and R$_7$ of the formula (IX) are the same as those in the formula (I).]

This method comprises reacting a 1,4-dihydro-4-oxo-3-pyridinecarboxamide derivative (IX) with a halogenating reagent. It is especially advantageous to use as the halogenating reagent, N-chlorosuccinimide or N-bromosuccinimide in an appropriate chlorinated hydrocarbon solvent (e.g., dichloromethane, chloroform, tetrachloromethane, trichloroethylene or tetrachloroethane) in the presence or absence of free-radical initiator.

The reaction may be also conducted by dissolving the compound (IX) in a halogenated hydrocarbon as mentioned above, and blowing or dropping into the resultant solution bromine or chlorine in gaseous or liquid state.

In the above halogenation of the compound (IX), it may additionally give the substitution at phenyl group which is bonded at the amide nitrogen atom.

(METHOD E)

This method in conducted by treating a compound of the formula (I) (R$_6$ is halogen atom) with an alkali metal halide which concerns an exchange of halogen atom (R$_6$) in the formula (I). It is useful to synthesize a compound of the formula (I) in which R$_6$ is fluorine atom and which it is difficult to produce by direct introduction.

(METHOD F)

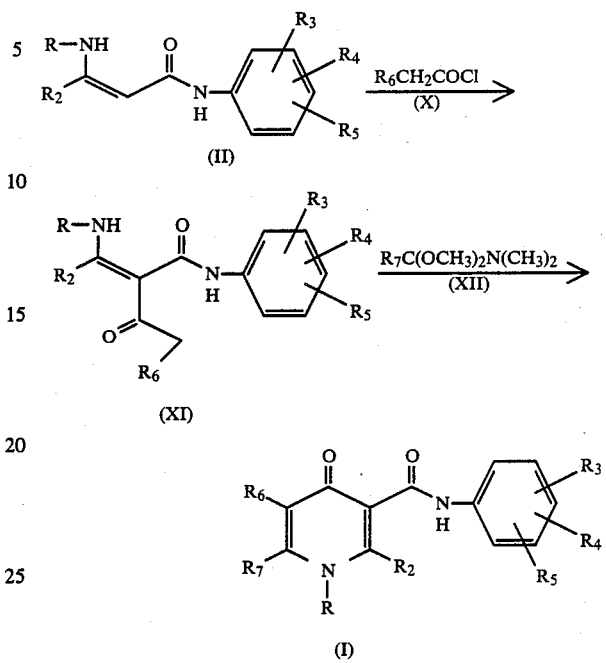

[R, R$_2$, R$_3$, R$_4$, R$_5$, R$_6$ and R$_7$ in the formula (II), (X), (XI) and (XII) are the same as those in the formula (I).]

This method comprises reacting an 3-aminoacrylic acid anilide derivative (II) with acid halide (X) in the presence of a base to yield a compound of the formula (XI), and then reacting this compound (XI) with a N,N-dimethylamide dimethylketal derivative (XII). It is possible to use an ester of formic acid instead of (XII) in the case that R$_7$ is hydrogen atom. This method is useful to synthesize a compound of the formula (I) in which R$_6$ is aryl group.

For herbicidal applications, the compounds of the present invention are generally formulated into herbicidal compositions. These compositions can be solids such as dusts, granules, or wettable powders; or they can be liquids such as solutions, aerosols, or emulsifiable concentrates.

For example, solid compositions such as dusts, wettable powders or granules can be prepared by blending the active compound with a solid inert carrier such as the kaolinites, bentonites, clays, talcs, silicas and the like. Liquids compositions such as solutions or emulsifiable concentrates can be prepared by dissolving the active compound with a liquid inert solvent such as xylene, ethanol, acetone, dimethylformamide, some vegetable oils, water and so on.

Surface active agents for wetting, dispersing or emulsifying are generally used with the herbicidal compositions as above defined. For example; polyoxyethylene-alkyl ethers, polyoxyethylene-sorbitan fatty acid esters, and other nonionic types; alkyl and alkylarlyl sulfonates and sulfates and their sodium salts and other anionic types or other types of surface active agents.

For pre-emergence applications these herbicidal compositions are usually applied either as sprays, dusts, or granules in the area in which suppression of vegetation is desied. For post-emergence applications control of established plant growth, sprays or dusts are most commonly used. These formulations may contain 10–80% for wettable powders, 1–10% for granules, or 10–50% for emulsifiable concentrates by weight of active ingredient. Dosage of these herbicidal compositions for pre-emergence or post-emergence applications is generally 0.1–2 Kg by weight of active ingredient.

This invention is illustrated further by examples hereinafter. Also, growth-inhibitory activities on plants of the compounds of the invention are shown in reference examples.

Furthermore, related specific compounds in addition to the compounds shown in the examples are as follows;

1. 1-butyl-2-ethyl-1,4-dihydro-6-methyl-4-oxo-N-phenyl-3-pyridinecarboxamide,
2. 2-ethyl-1,4-dihydro-6-methyl-4-oxo-1-pentyl-N-phenyl-3-pyridinecarboxamide,
3. 2-ethyl-1-hexyl-1,4-dihydro-6-methyl-4-oxo-N-phenyl-3-pyridinecarboxamide,
4. 1-(4-chlorophenylmethyl)-2-ethyl-1,4-dihydro-6-methyl-4-oxo-N-phenyl-3-pyridinecarboxamide,
5. 1-cyclohexylmethyl-2-ethyl-1,4-dihydro-6-methyl-4-oxo-N-phenyl-3-pyridinecarboxamide,
6. 2-ethyl-1-(2-furylmethyl)-1,4-dihydro-6-methyl-4-oxo-N-phenyl-3-pyridinecarboxamide,
7. 2-ethyl-1,4-dihydro-6-methyl-4-oxo-N-phenyl-1-(2-pyridylmethyl)-3-pyridinecarboxamide,
8. 2-ethyl-1,4-dihydro-6-methyl-4-oxo-N-phenyl-1-(3-pyridylmethyl)-3-pyridinecarboxamide,
9. 2-ethyl-1,4-dihydro-6-methyl-4-oxo-N-phenyl-1-(4-pyridylmethyl)-3-pyridinecarboxamide,
10. 1,4-dihydro-6-methyl-4-oxo-1-pentyl-N-phenyl-2-propyl-3-pyridinecarboxamide,
11. 1-hexyl-1,4-dihydro-6-methyl-4-oxo-N-phenyl-2-propyl-3-pyridinecarboxamide,
12. 1,4-dihydro-6-methyl-1-(4-methylphenylmethyl)-4-oxo-N-phenyl-2-propyl-3-pyridinecarboxamide,
13. 1-(4-chlorophenylmethyl)-1,4-dihydro-6-methyl-4-oxo-N-phenyl-2-propyl-3-pyridinecarboxamide,
14. 1-cyclohexylmethyl-1,4-dihydro-6-methyl-4-oxo-N-phenyl-2-propyl-3-pyridinecarboxamide,
15. 1-(2-furylmethyl)-1,4-dihydro-6-methyl-4-oxo-N-phenyl-2-propyl-3-pyridinecarboxamide,
16. 1,4-dihydro-6-methyl-4-oxo-N-phenyl-2-propyl-1-(2-pyridylmethyl)-3-pyridinecarboxamide,
17. 1,4-dihydro-6-methyl-4-oxo-N-phenyl-2-propyl-1-(3-pyridylmethyl)-3-pyridinecarboxamide,
18. 1,4-dihydro-6-methyl-4-oxo-N-phenyl-2-propyl-(4-pyridylmethyl)-3-pyridinecarboxamide,
19. 1,2-dibutyl-1,4-dihydro-6-methyl-4-oxo-N-phenyl-3-pyridinecarboxamide,
20. 2-butyl-1,4-dihydro-6-methyl-4-oxo-1-pentyl-N-phenyl-3-pyridinecarboxamide,
21. 2-butyl-1-hexyl-1,4-dihydro-6-methyl-4-oxo-N-phenyl-3-pyridinecarboxamide,
22. 2-butyl-1-(4-chlorophenylmethyl)-1,4-dihydro-6-methyl-4-oxo-N-phenyl-3-pyridinecarboxamide,
23. 2-butyl-cyclohexylmethyl-1,4-dihydro-6-methyl-4-oxo-N-phenyl-3-pyridinecarboxamide,
24. 2-butyl-1-(2-furylmethyl)-1,4-dihydro-6-methyl-4-oxo-N-phenyl-3-pyridinecarboxamide,
25. 2-butyl-1,4-dihydro-6-methyl-4-oxo-N-phenyl-1-(2-pyridylmethyl)-3-pyridinecarboxamide,
26. 2-butyl-1,4-dihydro-6-methyl-4-oxo-N-phenyl-1-(3-pyridylmethyl)-3-pyridinecarboxamide,
27. 2-butyl-1,4-dihydro-6-methyl-4-oxo-N-phenyl-1-(4-pyridylmethyl)-3-pyridinecarboxamide,
28. 1,4-dihydro-6-methyl-2-(2-methylpropyl)-4-oxo-N-phenyl-1-pentyl-3-pyridinecarboxamide,
29. 1-butyl-1,4-dihydro-6-methyl-2-(2-methylpropyl)-4-oxo-N-phenyl)-3-pyridinecarboxamide,
30. 1-hexyl-1,4-dihydro-6-methyl-2-(2-methylpropyl)-4-oxo-N-phenyl)-3-pyridinecarboxamide,
31. 1,4-dihydro-6-methyl-1-(4-methylphenylmethyl)-2-(2-methylpropyl)-4-oxo-N-phenyl-3-pyridinecarboxamide,
32. 1-(4-chlorophenylmethyl)-1,4-dihydro-6-methyl-2-(2-methylpropyl)-4-oxo-N-phenyl-3-pyridinecarboxamide,
33. 1-cyclohexylmethyl-1,4-dihydro-6-methyl-2-(2-methylpropyl)-4-oxo-N-phenyl-3-pyridinecarboxamide,
34. 1-(2-furylmethyl)-1,4-dihydro-6-methyl-2-(2-methylpropyl)-4-oxo-N-phenyl-3-pyridinecarboxamide,
35. 1,4-dihydro-6-methyl-2-(2-methylpropyl)-4-oxo-N-phenyl-1-(2-pyridylmethyl)-3-pyridinecarboxamide,
36. 1,4-dihydro-6-methyl-2-(2-methylpropyl)-4-oxo-N-phenyl-1-(3-pyridylmethyl)-3-pyridinecarboxamide,
37. 1,4-dihydro-6-metnyl-2-(2-methoxypropyl)-4-oxo-N-phenyl-1-(4-pyridylmethyl)-3-pyridinecarboxamide,
38. 1-butyl-1,4-dihydro-6-methyl-4-oxo-2-pentyl-3-pyridinecarboxamide,
39. 1,4-dihydro-6-methyl-4-oxo-1,2-dipentyl-N-phenyl-3-pyridinecarboxamide,
40. 1-hexyl-1,4-dihydro-6-methyl-4-oxo-2-pentyl-N-phenyl-3-pyridinecarboxamide,
41. 1,4-dihydro-6-methyl-1-(4-methylphenylmethyl)-4-oxo-2-pentyl-N-phenyl-3-pyridinecarboxamide,
42. 1-(4-chlorophenylmethyl)-1,4-dihydro-6-methyl-4-oxo-2-pentyl-N-phenyl-3-pyridinecarboxamide,
43. 1-cyclohexylmethyl-1,4-dihydro-6-methyl-4-oxo-2-pentyl-N-phenyl-3-pyridinecarboxamide,
44. 1-(2-furylmethyl)-1,4-dihydro-6-methyl-4-oxo-2-penyl-N-phenyl-3-pyridinecarboxamide,
45. 1,4-dihydro-6-methyl-4-oxo-2-pentyl-N-phenyl-1-(2-pyridylmethyl)-3-pyridinecarboxamide,
46. 1,4-dihydro-6-methyl-4-oxo-2-pentyl-N-phenyl-1-(3-pyridylmethyl)-3-pyridinecarboxamide,
47. 1,4-dihydro-6-methyl-4-oxo-2-pentyl-N-phentyl-1-(4-pyridylmethyl)-3-pyridinecarboxamide,
48. 1-cyclohexylmethyl-1,4-dihydro-6-methyl-4-oxo-2-pentyl-N,2-diphenyl-3-pyridinecarboxamide,
49. 1,4-dihydro-6-methyl-4-oxo-N,2-diphenyl-1-(3-pyridylmethyl)-3-pyridinecarboxamide,
50. 1,4-dihydro-6-methyl-4-oxo-N,2-diphenyl-1-(4-pyridylmethyl)-3-pyridinecarboxamide,
51. 1-butyl-2-(2-chlorophenyl)-1,4-dihydro-6-methyl-4-oxo-N-phenyl-3-pyridinecarboxamide,
52. 2-(2-chlorophenyl)-1,4-dihydro-6-methyl-4-oxo-1-pentyl-N-phenyl-3-pyridinecarboxamide,
53. 2-(2-chlorophenyl)-1-hexyl-1,4-dihydro-6-methyl-4-oxo-N-phenyl-3-pyridinecarboxamide,
54. 2-(2-chlorophenyl)-1,4-dihydro-6-methyl-4-oxo-N-phenyl-1-phenylmethyl-3-pyridinecarboxamide,
55. 2-(2-chlorophenyl)-1,4-dihydro-6-methyl-1-(4-methylphenylmethyl)-4-oxo-N-phenyl-3-pyridinecarboxamide,
56. 2-(2-chlorophenyl)-1-(4-chlorophenylmethyl)-1,4-dihydro-6-methyl-4-oxo-N-phenyl-3-pyridinecarboxamide,
57. 2-(2-chlorophenyl)-1-cyclohexylmethyl-1,4-dihydro-6-methyl-4-oxo-N-phenyl-3-pyridinecarboxamide,
58. 2-(2-chlorophenyl)-1-(2-furylmethyl)-1,4-dihydro-6-methyl-4-oxo-N-phenyl-3-pyridinecarboxamide, 59. 2-(2-chlorophenyl)-1,4-dihydro-6-methyl-4-oxo-N-phenyl-1-(2-pyridylmethyl)-3-pyridinecarboxamide,
60. 2-(2-chlorophenyl)-1,4-dihydro-6-methyl-4-oxo-N-phenyl-1-(3-pyridylmethyl)-3-pyridinecarboxamide,
61. 2-(2-chlorophenyl)-1,4-dihydro-6-methyl-4-oxo-N-phenyl-1-(4-pyridylmethyl)-3-pyridinecarboxamide,
62. 2-(3-chlorophenyl)-1-butyl-1,4-dihydro-6-methyl-4-oxo-N-phenyl-3-pyridinecarboxamide,
63. 2-(3-chlorophenyl)-1,4-dihydro-6-methyl-4-oxo-1-pentyl-N-phenyl-3-pyridinecarboxamide,
64. 2-(3-chlorophenyl)-1-hexyl-1,4-dihydro-6-methyl-4-oxo-N-phenyl-3-pyridinecarboxamide,
65. 2-(3-chlorophenyl)-1,4-dihydro-6-methyl-1-(4-methylphenylmethyl)-4-oxo-N-phenyl-3-pyridinecarboxamide,
66. 2-(3-chlorophenyl)-1-(4-chlorophenylmethyl)-1,4-dihydro-6-methyl-4-oxo-N-phenyl-3-pyridinecarboxamide,
67. 2-(3-chlorophenyl)-1-cyclohexylmethyl-1,4-dihydro-6-methyl-4-oxo-N-phenyl-3-pyridinecarbamoxide,
68. 2-(3-chlorophenyl)-1-(2-furylmethyl)-1,4-dihydro-6-methyl-4-oxo-N-phenyl-3-pyridinecarboxamide,
69. 2-(3-chlorophenyl)-1,4-dihydro-6-methyl-4-oxo-N-phenyl-1-(2-pyridylmethyl)-3-pyridinecarboxamide,
70. 2-(3-chlorophenyl)-1,4-dihydro-6-methyl-4-oxo-N-phenyl-1-(3-pyridylmethyl)-3-pyridinecarboxamide,
71. 2-(3-chlorophenyl)-1,4-dihydro-6-methyl-4-oxo-N-phenyl-1-(4-pyridylmethyl)-3-pyridinecarboxamide,
72. 1-butyl-1,4-dihydro-6-methyl-2-(2-methylphenyl)-4-oxo-N-phenyl-3-pyridinecarboxamide,
73. 1,4-dihydro-6-methyl-2-(2-methylphenyl)-4-oxo-1-pentyl-N-phenyl-3-pyridinecarboxamide,
74. 1-hexyl-1,4-dihydro-6-methyl-2-(2-methylphenyl)-4-oxo-N-phenyl-3-pyridinecarboxamide,
75. 1,4-dihydro-6-methyl-2-(2-methylphenyl)-4-oxo-N-phenyl-1-furylmethyl-3-pyridinecarboxamide,
76. 1,4-dihydro-6-methyl-2-(2-methylphenyl)-1-(4-methylphenylmethyl)-4-oxo-N-phenyl-3-pyridinecarboxamide,
77. 1-(4-chlorophenylmethyl)-1,4-dihydro-6-methyl-2-(2-methylphenyl)-4-oxo-N-phenyl-3-pyridinecarboxamide,
78. 1-cyclohexylmethyl-1,4-dihydro-6-methyl-2-(2-methylphenyl)-4-oxo-N-phenyl-3-pyridinecarboxamide,
79. 1-(2-furylmethyl)-1,4-dihydro-6-methyl-2-(2-methylphenyl)-4-oxo-N-phenyl-3-pyridinecarboxamide,
80. 1,4-dihydro-6-methyl-2-(2-methylphenyl)-4-oxo-N-phenyl-1-(2-pyridylmethyl)-3-pyridinecarboxamide,
81. 1,4-dihydro-6-methyl-2-(2-methylphenyl)-4-oxo-N-phenyl-1-(3-pyridylmethyl)-3-pyridinecarboxamide,
82. 1,4-dihydro-6-methyl-2-(2-methylphenyl)-4-oxo-N-phenyl-1-(4-pyridylmethyl)-3-pyridinecarboxamide,
83. 1-butyl-1,4-dihydro-6-methyl-2-(3-methylphenyl)-4-oxo-N-phenyl-3-pyridinecarboxamide,
84. 1,4-dihydro-6-methyl-2-(3-methylphenyl)-4-oxo-1-pentyl-N-phenyl-3-pyridinecarboxamide,
85. 1-hexyl-1,4-dihydro-6-methyl-2-(3-methylphenyl)-4-oxo-N-phenyl-3-pyridinecarboxamide,
86. 1,4-dihydro-6-methyl-2-(3-methylphenyl)-4-oxo-N-phenyl-1-phenylmethyl-3-pyridinecarboxamide,
87. 1,4-dihydro-6-methyl-2-(3-methylphenyl)-1-(4-methylphenylmethyl)-4-oxo-3-pyridinecarboxamide,
88. 1-(4-chlorophenylmethyl)-1,4-dihydro-6-methyl-2-(3-methylphenyl)-4-oxo-N-3-pyridinecarboxamide,
89. 1-cyclohexylmethyl-1,4-dihydro-6-methyl-2-(3-methylphenyl)-4-oxo-N-phenyl-3-pyridinecarboxamide,
90. 1-(2-furylmethyl)-1,4-dihydro-6-methyl-2-(3-methylphenyl)-4-oxo-N-phenyl-3-pyridinecarboxamide,
91. 1,4-dihydro-6-methyl-2-(3-methylphenyl)-4-oxo-N-phenyl-1-(2-pyridylmethyl)-3-pyridinecarboxamide,
92. 1,4-dihydro-6-methyl-2-(3-methylphenyl)-4-oxo-N-phenyl-1-(3-pyridylmethyl)-3-pyridinecarboxamide,
93. 1,4-dihydro-6-methyl-2-(3-methylphenyl)-4-ox-N-phenyl-1-(4-pyridylmethyl)-3-pyridinecarboxamide,
95. 2-(2-furyl)-1,4-dihydro-6-methyl-4-oxo-1-pentyl-N-phenyl-3-pyridinecarboxamide,
96. 1-hexyl-2-(2-furyl)-1,4-dihydro-6-methyl-4-ox-N-phenyl-3-pyridinecarboxamide,
97. 2-(2-furyl)-1,4-dihydro-6-methyl-1-(4-methylphenylmethyl)-4-oxo-N-phenyl-3-pyridinecarboxamide,
98. 1-(4-chlorophenylmethyl)-2-(2-furyl)-1,4-dihydro-6-methyl-4-oxo-N-phenyl-3-pyridinecarboxamide,
99. 1-cyclohexylmethyl-2-(2-furyl)-1,4-dihydro-6-methyl-4-oxo-N-phenyl-3-pyridinecarboxamide,
100. 2-(2-furyl)-1-(2-furylmethyl)-1,4-dihydro-6-methyl-4-oxo-N-phenyl-3-pyridinecarboxamide,
101. 2-(2-furyl)-1,4-dihydro-6-methyl-4-oxo-N-phenyl-1-(2-pyridylmethyl)-3-pyridinecarboxamide,
102. 2-(2-furyl)-1,4-dihydro-6-methyl-4-oxo-N-phenyl-1-(3-pyridylmethyl)-3-pyridinecarboxamide,
103. 2-(2-furyl)-1,4-dihydro-6-methyl-4-oxo-N-phenyl-1-(4-pyridylmethyl)-3-pyridinecarboxamide,
104. 1-butyl-1,4-dihydro-6-methyl-4-oxo-N-phenyl-2-(2-pyridyl)-3-pyridinecarboxamide,
105. 1,4-dihydro-6-methyl-4-oxo-1-pentyl-N-phenyl-2-(2-pyridyl)-3-pyridinecarboxamide,
106. 1-hexyl-1,4-dihydro-6-methyl-4-oxo-N-phenyl-2-(2-pyridyl)-3-pyridinecarboxamide,
107. 1,4-dihydro-6-methyl-4-oxo-N-phenyl-1-phenylmethyl-2-(2-pyridyl)-3-pyridinecarboxamide,
108. 1,4-dihydro-6-methyl-1-(4-methylphenylmethyl)-4-oxo-N-phenyl-2-(2-pyridyl)-3-pyridinecarboxamide,
109. 1-(4-chlorophenylmethyl)-1,4-dihydro-6-methyl-4-oxo-N-phenyl-2-(2-pyridyl)-3-pyridinecarboxamide,
110. 1-cyclohexylmethyl-1,4-dihydro-6-methyl-4-oxo-N-phenyl-2-(2-pyridyl)-3-pyridinecarboxamide,
111. 1-(2-furylmethyl)-1,4-dihydro-6-methyl-4-oxo-N-phenyl-2-(2-pyridyl)-3-pyridinecarboxamide,
112. 1,4-dihydro-6-methyl-4-oxo-N-phenyl-2-(2-pyridyl)-1-(2-pyridylmethyl)-3-pyridinecarboxamide,
113. 1,4-dihydro-6-methyl-4-oxo-N-phenyl-2-(2-pyridyl)-1-(3-pyridylmethyl)-3-pyridinecarboxamide,
114. 1,4-dihydro-6-methyl-4-oxo-N-phenyl-2-(2-pyridyl)-1-(4-pyridylmethyl)-3-pyridinecarboxamide,
115. 1-butyl-1,4-dihydro-6-methyl-4-oxo-N-phenyl-2-(3-pyridyl)-3-pyridinecarboxamide,
116. 1,4-dihydro-6-methyl-4-oxo-1-pentyl-N-phenyl-2-(3-pyridyl)-3-pyridinecarboxamide,
117. 1-hexyl-1,4-dihydro-6-methyl-4-oxo-N-phenyl-2-(3-pyridyl)-3-pyridine-carboxamide,
118. 1,4-dihydro-6-methyl-4-oxo-N-phenyl-1-(phenylmethyl)-2-(3-pyridyl)-3-pyridinecarboxamide,
119. 1,4-dihydro-6-methyl-1-(4-methylphenylmethyl)-4-oxo-N-phenyl-2-(3-pyridyl)-3-pyridinecarboxamide,
120. 1-(4-chlorophenylmethyl)-1,4-dihydro-6-methyl-4-oxo-N-phenyl-2-(3-pyridyl)-3-pyridinecarboxamide,
121. 1-cyclohexylmethyl-1,4-dihydro-6-methyl-4-oxo-N-phenyl-2-(3-pyridyl)-3-pyridinecarboxamide, 122. 1-(2-furylmethyl)-1,4-dihydro-6-methyl-4-oxo-N-phenyl-2-(3-pyridyl)-3-pyridinecarboxamide,
123. 1,4-dihydro-6-methyl-4-oxo-N-phenyl-2-(3-pyridyl)-1-(2-pyridylmethyl)-3-pyridinecarboxamide,
124. 1,4-dihydro-6-methyl-4-oxo-N-phenyl-2-(3-pyridyl)-1-(3-pyridylmethyl)-3-pyridinecarboxamide,
125. 1,4-dihydro-6-methyl-4-oxo-N-phenyl-2-(3-pyridyl)-1-(4-pyridylmethyl)-3-pyridinecarboxamide,
126. 1-butyl-1,4-dihydro-6-methyl-4-oxo-N-phenyl-2-(4-pyridyl)-3-pyridinecarboxamide,
127. 1,4-dihydro-6-methyl-4-oxo-1-pentyl-N-phenyl-2-(4-pyridyl)-3-pyridinecarboxamide,
128. 1-hexyl-1,4-dihydro-6-methyl-4-oxo-N-phenyl-2-(4-pyridyl)-3-pyridinecarboxamide,
129. 1,4-dihydro-6-methyl-4-oxo-N-phenyl-1-phenylmethyl-2-(4-pyridyl)-3-pyridinecarboxamide,
130. 1,4-dihydro-6-methyl-1-(4-methylphenylmethyl)-4-oxo-N-phenyl-2-(4-pyridyl)-3-pyridinecarboxamide,
131. 1-(4-chlorophenylmethyl)-1,4-dihydro-6-methyl-4-oxo-N-phenyl-2-(4-pyridyl)-3-pyridinecarboxamide,
132. 1-cyclohexylmethyl-1,4-dihydro-6-methyl-4-oxo-N-phenyl-2-(4-pyridyl)-3-pyridinecarboxamide, 3-pyridinecarboxamide,
133. 1-(2-furylmethyl)-1,4-dihydro-6-methyl-4-oxo-N-phenyl-2-(4-pyridyl)-3-pyridinecarboxamide,
134. 1,4-dihydro-6-methyl-4-oxo-N-phenyl-2-(4-pyridyl)-1-(2-pyridylmethyl)-3-pyridinecarboxamide,
135. 1,4-dihydro-6-methyl-4-oxo-N-phenyl-2-(4-pyridyl)-1-(3-pyridylmethyl)-3-pyridinecarboxamide,
136. 1,4-dihydro-6-methyl-4-oxo-N-phenyl-2-(4-pyridyl)-1-(4-pyridylmethyl)-3-pyridinecarboxamide,
137. 1-butyl-2-ethyl-1,4-dihydro-6-methyl-N-(2-methylphenyl)-4-oxo-3-pyridinecarboxamide,
138. 2-ethyl-1,4-dihydro-6-methyl-N-(2-methylphenyl)-4-oxo-1-pentyl-3-pyridinecarboxamide,
139. 2-ethyl-1-hexyl-1,4-dihydro-6-methyl-N-(2-methylphenyl)-4-oxo-3-pyridinecarboxamide,
140. 2-ethyl-1,4-dihydro-6-methyl-N-(2-methylphenyl)-4-oxo-1-phenylmethyl-3-pyridinecarboxamide,
141. 2-ethyl-1,4-dihydro-6-methyl-N-(2-methylphenyl)-1-(4-methylphenylmethyl)-4-oxo-3-pyridinecarboxamide,
142. 1-(4-chlorophenylmethyl)-2-ethyl-1,4-dihydro-6-methyl-N-(2-methylphenyl)-4-oxo-3-pyridinecarboxamide,
143. 1-cyclohexylmethyl-2-ethyl-1,4-dihydro-6-methyl-N-(2-methylphenyl)-4-oxo-3-pyridinecarboxamide,
144. 2-ethyl-1-(2-furylmethyl)-1,4-dihydro-6-methyl-N-(2-methylphenyl)-4-oxo-3-pyridinecarboxamide,
145. 2-ethyl-1,4-dihydro-6-methyl-N-(2-methylphenyl)-4-oxo-1-(2-pyridylmethyl)-3-pyridinecarboxamide,
146. 2-ethyl-1,4-dihydro-6-methyl-N-(2-methylphenyl)-4-oxo-1-(3-pyridylmethyl)-3-pyridinecarboxamide,
147. 2-ethyl-1,4-dihdro-6-methyl-N-(2-methylphenyl)-4-oxo-1-(4-pyridylmethyl)-3-pyridinecarboxamide,
148. 1-butyl-1,4-dihydro-6-methyl-N-(2-methylphenyl)-4-oxo-2-propyl-3-pyridinecarboxamide,
149. 1,4-dihydro-6-methyl-N-(2-methylphenyl)-4-oxo-1-pentyl-2-propyl-3-pyridinecarboxamide,
150. 1-hexyl-1,4-dihydro-6-methyl-N-(2-methylphenyl)-4-oxo-2-propyl-3-pyridinecarboxamide,
151. 1,4-dihydro-6-methyl-N-(2-methylphenyl)-1-(4-methylphenylmethyl)-4-oxo-2-propyl-3-pyridinecarboxamide,
152. 1-cyclohexylmethyl-1,4-dihydro-6-methyl-N-(2-methylphenyl)-4-oxo-2-propyl-3-pyridinecarboxamide,
153. 1-(2-furylmethyl)-1,4-dihydro-6-methyl-N-(2-methylphenyl)-4-oxo-2-propyl-3-pyridinecarboxamide,
154. 1,4-dihydro-6-methyl-N-(2-methylphenyl)-4-oxo-2-propyl-1-(2-pyridylmethyl)-3-pyridinecarboxamide,
155. 1,4-dihydro-6-methyl-N-(2-methylphenyl)-4-oxo-2-propyl-1-(3-pyridylmethyl)-3-pyridinecarboxamide,
156. 1,4-dihydro-6-methyl-N-(2-methylphenyl)-4-oxo-2-propyl-1-(4-pyridylmethyl)-3-pyridinecarboxamide,
157. 1,2-dibutyl-1,4-dihydro-6-methyl-N-(2-methylphenyl)-4-oxo-3-pyridinecarboxamide,
158. 2-butyl-1,4-dihydro-6-methyl-N-(2-methylphenyl)-4-oxo-1-propyl-3-pyridinecarboxamide,
159. 2-butyl-1-hexyl-1,4-dihydro-6-methyl-N-(2-methylphenyl)-4-oxo-3-pyridinecarboxamide,
160. 2-butyl-1,4-dihydro-6-methyl-N-(2-methylphenyl)-4-oxo-1-phenylmethyl-3-pyridinecarboxamide,
161. 2-butyl-1,4-dihydro-6-methyl-N-(2-methylphenyl)-1-(4-methylphenylmethyl)-4-oxo-3-pyridinecarboxamide,
162. 2-butyl-1-(4-chlorophenylmethyl)-1,4-dihydro-6-methyl-N-(2-methylphenyl)-4-oxo-3-pyridinecarboxamide,
163. 2-butyl-1-cyclohexylmethyl-1,4-dihydro-6-methyl-N-(2-methylphenyl)-4-oxo-3-pyridinecarboxamide,
164. 2-butyl-1-(2-furylmethyl)-1,4-dihydro-6-methyl-N-(2-methylphenyl)-4-oxo-3-pyridinecarboxamide,
165. 2-butyl-1,4-dihydro-6-methyl-N-(2-methylphenyl)-4-oxo-1-(2-pyridylmethyl)-3-pyridinecarboxamide,
166. 2-butyl-1,4-dihydro-6-methyl-N-(2-methylphenyl)-4-oxo-1-(3-pyridylmethyl)-3-pyridinecarboxamide,
167. 2-butyl-1,4-dihydro-6-methyl-N-(2-methylphenyl)-4-oxo-1-(4-pyridylmethyl)-3-pyridinecarboxamide,
168. 1-butyl-1,4-dihydro-6-methyl-N-(2-methylphenyl)-2-(2-methylpropyl)-4-oxo-3-pyridinecarboxamide,
169. 1,4-dihydro-6-methyl-N-(2-methylphenyl)-2-(2-methylpropyl)-1-pentyl-4-oxo-3-pyridinecarboxamide,
170. 1-hexyl-1,4-dihydro-6-methyl-N-(2-methylphenyl)-2-(2-methylpropyl)-4-oxo-3-pyridinecarboxamide,
171. 1,4-dihydro-6-methyl-N-(2-methylphenyl)-2-(2-methylpropyl)-4-oxo-1-phenylmethyl-3-pyridinecarboxamide,
172. 1,4-dihydro-6-methyl-N-(2-methylphenyl)-1-(4-methylphenylmethyl)-2-(2-methylpropyl)-4-oxo-3-pyridinecarboxamide,
173. 1-(4-chlorophenylmethyl)-1,4-dihydro-6-methyl-N-(2-methylphenyl)-2-(2-methylpropyl)-4-oxo-3-pyridinecarboxamide,
174. 1-cyclohexylmethyl-1,4-dihydro-6-methyl-N-(2-methylphenyl)-2-(2-methylpropyl)-4-oxo-3-pyridinecarboxamide,
175. 1-(2-furylmethyl)-1,4-dihydro-6-methyl-N-(2-methylphenyl)-2-(2-methylpropyl)-4-oxo-3-pyridinecarboxamide,
176. 1,4-dihydro-6-methyl-N-(2-methylphenyl)-2-(2-methylpropyl)-4-oxo-1-(2-pyridylmethyl)-3-pyridinecarboxamide,
177. 1,4-dihydro-6-methyl-N-(2-methylphenyl)-2-(2-methylpropyl)-4-oxo-1-(3-pyridylmethyl)-3-pyridinecarboxamide,
178. 1,4-dihydro-6-methyl-N-(2-methylphenyl)-2-(2-methylpropyl)-4-oxo-1-(4-pyridylmethyl)-3-pyridinecarboxamide, 179. 1-butyl-1,4-dihydro-6-methyl-N-(2-methylphenyl)-4-oxo-2-pentyl-3-pyridinecarboxamide,
180. 1,4-dihydro-6-methyl-N-(2-methylphenyl)-4-oxo-1,2-dipentyl-3-pyridinecarboxamide,
181. 1-hexyl-1,4-dihydro-6-methyl-N-(2-methylphenyl)-4-oxo-2-pentyl-3-pyridinecarboxamide,
182. 1,4-dihydro-6-methyl-N-(2-methylphenyl)-4-oxo-2-pentyl-1-phenylmethyl-3-pyridinecarboxamide,
183. 1,4-dihydro-6-methyl-N-(2-methylphenyl)-1-(4-methylphenylmethyl-4-oxo-2-pentyl-3-pyridinecarboxamide,
184. 1-(4-chlorophenylmethyl)-1,4-dihydro-6-methyl-N-(2-methylphenyl)-4-oxo-2-pentyl-3-pyridinecarboxamide,
185. 1-cyclohexylmethyl-1,4-dihydro-6-methyl-N-(2-methylphenyl)-4-oxo-2-pentyl-3-pyridinecarboxamide,
186. 1-(2-furylmethyl)-1,4-dihydro-6-methyl-N-(2-methylphenyl)-4-oxo-2-pentyl-3-pyridinecarboxamide,
187. 1,4-dihydro-6-methyl-N-(2-methylphenyl)-4-oxo-2-pentyl-1-(2-pyridylmethyl)-3-pyridinecarboxamide,
188. 1,4-dihydro-6-methyl-N-(2-methylphenyl)-4-oxo-2-pentyl-1-(3-pyridylmethyl)-3-pyridinecarboxamide,
189. 1,4-dihydro-6-methyl-N-(2-methylphenyl)-4-oxo-2-pentyl-1-(4-pyridylmethyl)-3-pyridinecarboxamide,
190. 1,4-dihydro-6-methyl-N-(2-methylphenyl)-4-oxo-1-pentyl-2-phenyl-3-pyridinecarboxamide,
191. 1-hexyl-1,4-dihydro-6-methyl-N-(2-methylphenyl)-4-oxo-2-phenyl-3-pyridinecarboxamide,
192. 1,4-dihydro-6-methyl-N-(2-methylphenyl)-1-(4-methylphenylmethyl)-4-oxo-2-phenyl-3-pyridinecarboxamide,
193. 1-cyclohexylmethy-1,4-dihydro-6-methyl-N-(2-methylphenyl)-4-oxo-2-phenyl-3-pyridinecarboxamide,
194. 1-(2-furylmethyl)-1,4-dihydro-6-methyl-N-(2-methylphenyl)-4-oxo-2-phenyl-3-pyridinecarboxamide,
195. 1,4-dihydro-6-methyl-N-(2-methylphenyl)-4-oxo-2-phenyl-1-(2-pyridylmethyl)-3-pyridinecarboxamide,
196. 1,4-dihydro-6-methyl-N-(2-methylphenyl)-4-oxo-2-phenyl-1-(3pyridylmethyl)-3-pyridinecarboxamide,
197. 1,4-dihydro-6-methyl-N-(2-methylphenyl)-4-oxo-2-phenyl-1-(4-pyridylmethyl)-3-pyridinecarboxamide,
198. 1-butyl-2-(2-chlorophenyl)-1,4-dihydro-6-methyl-N-(2-methylphenyl)-4-oxo-3-pyridinecarboxamide,
199. 2-(2-chlorophenyl)-1,4-dihydro-6-methyl-N-(2-methylphenyl)-4-oxo-1-pentyl-3pyridinecarboxamide,
200. 2-(2-chlorophenyl)-1-hexyl-1,4-dihydro-6-methyl-N-(2-methylphenyl)-4-oxo-3-pyridinecarboxamide,
201. 2-(2-chlorophenyl)-1,4-dihydro-6-methyl-N-(2-methylphenyl)-4-oxo-1-phenylmethyl-3-pyridinecarboxamide,
202. 2-(2-chlorophenyl)-1,4-dihydro-6-methyl-N-(2-methylphenyl)-1-(4-methylphenylmethyl)-4-oxo-3-pyridinecarboxamide,
203. 2-(2-chlorophenyl)-1-(4-chlorophenylmethyl)-1,4-dihydro-6-methyl-N-(2-methylphenyl)-4-oxo-3-pyridinecarboxamide,
204. 2-(2-chlorophenyl)-1-cyclohexylmethyl-1,4-dihydro-6-methyl-N-(2-methylphenyl)-4-oxo-3-pyridinecarboxamide,
205. 2-(2-chlorophenyl)-1-(2-furylmethyl)-1,4-dihydro-6-methyl-N-(2-methylphenyl)-4-oxo-3-pyridinecarboxamide,
206. 2-(2-chlorophenyl)-1,4-dihydro-6-methyl-N-(2-methylphenyl)-4-oxo-1-(2-pyridylmethyl)-3-pyridinecarboxamide,
207. 2-(2-chlorophenyl)-1,4-dihydro-6-methyl-N-(2-methylphenyl)-4-oxo-1-(3-pyridylmethyl)-3-pyridinecarboxmide,
208. 2-(2-chlorophenyl)-1,4-dihydro-6-methyl-N-(2-methylphenyl)-4-oxo-1-(4-pyridylmethyl)-3-pyridinecarboxamide,
209. 1-butyl-2-(3-chlorophenyl)-1,4-dihydro-6-methyl-N-(2-methylphenyl)-4-oxo-3-pyridinecarboxamide,
210. 2-(3-chlorophenyl)-1,4-dihydro-6-methyl-N-(2-methylphenyl)-4-oxo-1-pentyl-3-pyridinecarboxamide,
211. 2-(3-chlorophenyl)-1-hexyl-1,4-dihydro-6-methyl-N-(2-methylphenyl)-4-oxo-3-pyridinecarboxamide,
212. 2-(3-chlorophenyl)-1,4-dihydro-6-methyl-N-(2-methylphenyl)-4-oxo-1-phenylmethyl-3-pyridinecarboxamide,
213. 2-(3-chlorophenyl)-1,4-dihydro-6-methyl-N-(2-methylphenyl)-1-(4-methylphenylmethyl)-4-oxo-3-pyridinecarboxamide,
214. 2-(3-chlorophenyl)-1-(4-chlorophenylmethyl)-1,4-dihydro-6-methyl-N-(2-methylphenyl)-4-oxo-3-pyridinecarboxamide,
215. 2-(3-chlorophenyl)-1-cyclohexylmethyl-1,4-dihydro-6-methyl-N-(2-methylphenyl)-4-oxo-3-pyridinecarboxamide,
216. 2-(3-chlorophenyl)-1-(2-furylmethyl)-1,4-dihydro-6-methyl-N-(2-methylphenyl)-4-oxo-3-pyridinecarboxamide,
217. 2-(3-chlorophenyl)-1,4-dihydro-6-methyl-N-(2-methylphenyl)-4-oxo-1-(2-pyridylmethyl)-3-pyridinecarboxamide,
218. 2-(3-chlorophenyl)-1,4-dihydro-6-methyl-N-(2-methylphenyl)-4-oxo-1-(3-pyridylmethyl)-3-pyridinecarboxamide,
219. 2-(3-chlorophenyl)-1,4-dihydro-6-methyl-N-(2-methylphenyl)-4-oxo-1-(4-pyridylmethyl)-3-pyridinecarboxamide,
220. 1-butyl-1,4-dihydro-6-methyl-N,2-bis(2-methylphenyl)-4-oxo-3-pyridinecarboxamide,
221. 1,4-dihydro-6-methyl-N,2-bis(2-methylphenyl)-4-oxo-1-pentyl-3-pyridinecarboxamide,
222. 1-hexyl-1,4-dihydro-6-methyl-N,2-bis(2-methylphenyl)-4-oxo-3-pyridinecarboxamide,
223. 1,4-dihydro-6-methyl-N,2-bis(2-methylphenyl)-4-oxo-1-phenylmethyl-3-pyridinecarboxamide,
224. 1,4-dihydro-6-methyl-N,2-bis(2-methylphenyl)-1-(4-methylphenylmethyl)-4-oxo-3-pyridinecarboxamide,
225. 1-(4-chlorophenymethyl)-1,4-dihydro-6-methyl-N,2-bis(2-methylphenyl)-4-oxo-3-pyridinecarboxamide,
226. 1-cyclohexylmethyl-1,4-dihydro-6-methyl-N,2-bis(2-methylphenyl)-4-oxo-3-pyridinecarboxamide,
227. 1-(2-furylmethyl)-1,4-dihydro-6-methyl-N,2-bis(2-methylphenyl)-4-oxo-3-pyridinecarboxamide,
228. 1,4-dihydro-6-methyl-N,2-bis(2-methylphenyl)-4-oxo-1-(2-pyridylmethyl)-3-pyridinecarboxamide,
229. 1,4-dihydro-6-methyl-N,2-bis(2-methylphenyl)-4-oxo-1-(3-pyridylmethyl)-3-pyridinecarboxamide,
230. 1,4-dihydro-6-methyl-N,2-bis(2-methylphenyl)-4-oxo-1-(4-pyridylmethyl)-3-pyridinecarboxamide, 231. 1-butyl-1,4-dihydro-6-methyl-N-(2-methylphenyl)-2-(3-methylphenyl)-4-oxo-3-pyridinecarboxamide,
232. 1,4-dihydro-6-methyl-N-(2-methylphenyl)-2-(3-methylphenyl)-4-oxo-1-pentyl-3-pyridinecarboxamide,
233. 1-hexyl-1,4-dihydro-6-methyl-N-(2-methylphenyl)-2-(3-methylphenyl)-4-oxo-3-pyridinecarboxamide,
234. 1,4-dihydro-6-methyl-N-(2-methylphenyl)-2-(3-methylphenyl)-4-oxo-1-phenylmethyl-3-pyridinecarboxamide,
235. 1,4-dihydro-6-methyl-N-(2-methylphenyl)-2-(3-methylphenyl)-1-(4-methylphenylmethyl)-4-oxo-3-pyridinecarboxamide,
236. 1-(4-chlorophenylmethyl)-1,4-dihydro-6-methyl-N-(2-methylphenyl)-2-(3-methylphenyl)-4-oxo-3-pyridinecarboxamide,
237. 1-cyclohexylmethyl-1,4-dihydro-6-methyl-N-(2-methylphenyl)-2-(3-methylphenyl)-4-oxo-3-pyridinecarboxamide,
238. 1-(2-furylmethyl)-1,4-dihydro-6-methyl-N-(2-methylphenyl)-2-(3-methylphenyl)-4-oxo-3-pyridinecarboxamide,
239. 1,4-dihydro-6-methyl-N-(2-methylphenyl)-2-(3-methylphenyl)-4-oxo-1-(2-pyridylmethyl)-3-pyridinecarboxamide,
240. 1,4-dihydro-6-methyl-N-(2-methylphenyl)-2-(3-methylphenyl)-4-oxo-1-(3-pyridylmethyl)-3-pyridinecarboxamide,
241. 1,4-dihydro-6-methyl-N-(2-methylphenyl)-2-(3-methylphenyl)-4-oxo-1-(4-pyridylmethyl)-3-pyridinecarboxamide,
242. 1-butyl-2-(2-furyl)-1,4-dihydro-6-methyl-N-(2-methylphenyl)-4-oxo-b 3-pyridinecarboxamide,
243. 2-(2-furyl)-1,4-dihydro-6-methyl-N-(2-methylphenyl)-4-oxo-1-pentyl-3-pyridinecarboxamide,
244. 2-(2-furyl)-1-hexyl-1,4-dihydro-6-methyl-N-(2-methylphenyl)-4-oxo-3-pyridinecarboxamide,
245. 2-(2-furyl)-1,4-dihydro-6-methyl-N-(2-methylphenyl)-4-oxo-1-phenylmethyl-3-pyridinecarboxamide,
246. 2-(2-furyl)-1,4-dihydro-6-methyl-N-(2-methylphenyl)-1-(4-methylphenylmethyl)-4-oxo-3-pyridinecarboxamide,
247. 1-(4-chlorophenylmethyl)-2-(2-furyl)-1,4-dihydro-6-methyl-N-(2-methylphenyl)-4-oxo-3-pyridinecarboxamide,
248. 1-cyclohexylmethyl-2-(2-furyl)-1,4-dihydro-6-methyl-N-(2-methylphenyl)-4-oxo-3-pyridinecarboxamide,
249. 2-(2-furyl)-1-(2-furylmethyl)-1,4-dihydro-6-methyl-N-(2-methylphenyl)-4-oxo-3-pyridinecarboxamide,
250. 2-(2-furyl)-1,4-dihydro-6-methyl-N-(2-methylphenyl)-4-oxo-1-(2-pyridylmethyl)-3-pyridinecarboxamide,
251. 2-(2-furyl)-1,4-dihydro-6-methyl-N-(2-methylphenyl)-4-oxo-1-(3-pyridylmethyl)-3-pyridinecarboxamide,
252. 2-(2-furyl)-1,4-dihydro-6-methyl-N-(2-methylphenyl)-4-oxo-1-(4-pyridylmethyl)-3-pyridinecarboxamide,
253. 1-butyl-1,4-dihydro-6-methyl-N-(2-methylphenyl)-4-oxo-2-(2-pyridyl)-3-pyridinecarboxamide,
254. 1,4-dihydro-6-methyl-N-(2-methylphenyl)-4-oxo-1-pentyl-2-(2-pyridyl)-3-pyridinecarboxamide,
255. 1-hexyl-1,4-dihydro-6-methyl-N-(2-methylphenyl)-4-oxo-2-(2-pyridyl)-3-pyridinecarboxamide,
256. 1,4-dihydro-6-methyl-N-(2-methylphenyl)-4-oxo-1-phenylmethyl-2-(2-pyridyl)-3-pyridinecarboxamide,
257. 1,4-dihydro-6-methyl-N-(2-methylphenyl)-1-(4-methylphenylmethyl)-4-oxo-2-(2-pyridyl)-3-pyridinecarboxamide,
258. 1-(4-chlorophenylmethyl)-1,4-dihydro-6-methyl-N-(2-methylphenyl)-4-oxo-2-(2-pyridyl)-3-pyridinecarboxamide,
259. 1-cyclohexylmethyl-1,4-dihydro-6-methyl-N-(2-methylphenyl)-4-oxo-2-(2-pyridyl)-3-pyridinecarboxamide,
260. 1-(2-furylmethyl)-1,4-dihydro-6-methyl-N-(2-methylphenyl)-4-oxo-2-(2-pyridyl)-3-pyridinecarboxamide,
261. 1,4-dihydro-6-methyl-N-(2-methylphenyl)-4-oxo-2-(2-pyridyl)-1-(2-pyridylmethyl)-3-pyridinecarboxamide,
262. 1,4-dihydro-6-methyl-N-(2-methylphenyl)-4-oxo-2-(2-pyridyl)-1-(3-pyridylmethyl)-3-pyridinecarboxamide,
263. 1,4-dihydro-6-methyl-N-(2-methylphenyl)-4-oxo-2-(2-pyridyl)-1-(4-pyridylmethyl)-3-pyridinecarboxamide,
264. 1-butyl-1,4-dihydro-6-methyl-N-(2-methylphenyl)-4-oxo-2-(3-pyridyl)-3-pyridinecarboxamide,
265. 1,4-dihydro-6-methyl-N-(2-methylphenyl)-4-oxo-1-pentyl-2-(3-pyridyl)-3-pyridinecarboxamide,
266. 1-hexyl-1,4-dihydro-6-methyl-N-(2-methylphenyl)-4-oxo-2-(3-pyridyl)-3-pyridinecarboxamide,
267. 1,4-dihydro-6-methyl-N-(2-methylphenyl)-4-oxo-1-phenylmethyl-2-(3-pyridyl)-3-pyridinecarboxamide,
268. 1,4-dihydro-6-methyl-N-(2-methylphenyl)-1-4-methylphenylmethyl)-4-oxo-2-(3-pyridyl)-3-pyridinecarboxamide,
269. 1-(4-chlorophenylmethyl)-1,4-dihydro-6-methyl-N-(2-methylphenyl)-4-oxo-2-(3-pyridyl)-3-pyridinecarboxamide,
270. 1-cyclohexylmethyl-1,4-dihydro-6-methyl-N-(2-methylphenyl)-4-oxo-2-(3-pyridyl)-3-pyridinecarboxamide,
271. 1-(2-furylmethyl)-1,4-dihydro-6-methyl-N-(2-mthylphenyl)-4-oxo-2-(3-pyridyl)-3-pyridinecarboxamide,
272. 1,4-dihydro-6-methyl-N-(2-methylphenyl)-4-oxo-2-(3pyridyl)-1-(2-pyridylmethyl)-3-pyridinecarboxamide,
273. 1,4-dihydro-6-methyl-N-(2-methylphenyl)-4-oxo-2-(3-pyridyl)-1-(3-pyridylmethyl)-3-pyridinecarboxamide,
274. 1,4-dihydro-6-methyl-N-(2-methylphenyl)-4-oxo-2-(3-pyridyl)-1-(4-pyridylmethyl)-3-pyridinecarboxamide,
275. 1-butyl-1,4-dihydro-6-methyl-N-(2-methylphenyl)-4-oxo-2-(4-pyridyl)-3-pyridinecarboxamide,
276. 1,4-dihydro-6-methyl-N-(2-methylphenyl)-4-oxo-1-pentyl-2-(4-pyridyl)-3-pyridinecarboxamide,
277. 1-hexyl-1,4-dihydro-6-methyl-N-(2-methylphenyl)-4-oxo-2-(4-pyridyl)-3-pyridinecarboxamide,
278. 1,4-dihydro-6-methyl-N-(2-methylphenyl)-4-oxo-1-phenylmethyl-2-(4-pyridyl)-3-pyridinecarboxamide,
279. 1,4-dihydro-6-methyl-N-(2-methylphenyl)-1-(4-methylphenylmethyl)-4-oxo-2-(4-pyridyl)-3-pyridinecarboxamide, 280. 1-(4-chlorophenylmethyl)-1,4-dihydro-6-methyl-N-(2-methylphenyl)-4-oxo-2-(4-pyridyl)-3-pyridinecarboxamide,
281. 1-cyclohexylmethyl-1,4-dihydro-6-methyl-N-(2-methylphenyl)-4-oxo-2-(4-pyridyl)-3-pyridinecarboxamide,
282. 1-(2-furylmethyl)-1,4-dihydro-6-methyl-N-(2-methylphenyl)-4-oxo-2-(4-pyridyl)-3-pyridinecarboxamide,
283. 1,4-dihydro-6-methyl-N-(2-methylphenyl)-4-oxo-2-(4-pyridyl)-1-(2-pyridylmethyl)-3-pyridinecarboxamide,
284. 1,4-dihydro-6-methyl-N-(2-methylphenyl)-4-oxo-2-(4-pyridyl)-1-(3-pyridylmethyl)-3-pyridinecarboxamide,
285. 1,4-dihydro-6-methyl-N-(2-methylphenyl)-4-oxo-2-(4-pyridyl)-1-(4-pyridylmethyl)-3-pyridinecarboxamide,
286. 1-butyl-N-(2-chlorophenyl)-2-ethyl-1,4-dihydro-6-methyl-4-oxo-3-pyridinecarboxamide,
287. N-(2-chlorophenyl)-2-ethyl-1,4-dihydro-6-methyl-4-oxo-1-pentyl-3-pyridinecarboxamide,
288. N-(2-chlorophenyl)-2-ethyl-1-hexyl-1,4-dihydro-6-methyl-4-oxo-3-pyridinecarboxamide,
289. N-(2-chlorophenyl)-2-ethyl-1,4-dihydro-6-methyl-4-oxo-1-phenylmethyl-3-pyridinecarboxamide,
290. N-(2-chlorophenyl)-2-ethyl-1,4-dihydro-6-methyl-1-(4-methylphenylmethyl)-4-oxo-3-pyridinecarboxamide,
291. N-(2-chlorophenyl)-1-(4-chlorophenylmethyl)-2-ethyl-1,4-dihydro-6-methyl-4-oxo-3-pyridinecarboxamide,
292. N-(2-chlorophenyl)-1-cyclohexylmethyl-2-ethyl-1,4-dihydro-6-methyl-4-oxo-3-pyridinecarboxamide,
293. N-(2-chlorophenyl)-2-ethyl-1-(2-furylmethyl)-1,4-dihydro-6-methyl-4-oxo-3-pyridinecarboxamide,
294. N-(2-chlorophenyl)-2-ethyl-1,4-dihydro-6-methyl-4-oxo-1-(2-pyridylmethyl)-3-pyridinecarboxamide,
295. N-(2-chlorophenyl)-2-ethyl-1,4-dihydro-6-methyl-4-oxo-1-(3-pyridylmethyl)-3-pyridinecarboxamide,
296. N-(2-chlorophenyl)-2-ethyl-1,4-dihydro-6-methyl-4-oxo-1-(4-pyridylmethyl)-3-pyridinecarboxamide,
297. 1-butyl-N-(2-chlorophenyl)-1,4-dihydro-6-methyl-4-oxo-2-propyl-3-pyridinecarboxamide,
298. N-(2-chlorophenyl)-1,4-dihydro-6-methyl-4-oxo-1-pentyl-2-propyl-3-pyridinecarboxamide,
299. N-(2-chlorophenyl)-1-hexyl-1,4-dihydro-6-methyl-4-oxo-2-propyl-3-pyridinecarboxamide,
300. N-(2-chlorophenyl)-1,4-dihydro-6-methyl-4-oxo-1-phenylmethyl-2-propyl-3-pyridinecarboxamide,
301. N-(2-chlorophenyl)-1,4-dihydro-6-methyl-1-(4-methylphenylmethyl)-4-oxo-2-propyl-3-pyridinecarboxamide,
302. N-(2-chlorophenyl)-1-(4-chlorophenylmethyl)-1,4-dihydro-6-methyl-4-oxo-2-propyl-3-pyridinecarboxamide,
303. N-(2-chlorophenyl)-1-cyclohexylmethyl-1,4-dihydro-6-methyl-4-oxo-2-propyl-3-pyridinecarboxamide,
304. N-(2-chlorophenyl)-1-(2-furylmethyl)-1,4-dihydro-6-methyl-4-oxo-2-propyl-3-pyridinecarboxamide,
305. N-(2-chlorophenyl)-1,4-dihydro-6-methyl-4-oxo-2-propyl-1-(2-pyridylmethyl)-3-pyridinecarboxamide,
306. N-(2-chlorophenyl)-1,4-dihydro-6-methyl-4-oxo-2-propyl-1-(3-pyridylmethyl)-3-pyridinecarboxamide,
307. N-(2-chlorophenyl)-1,4-dihydro-6-methyl-4-oxo-2-propyl-1-(4-pyridylmethyl)-3-pyridinecarboxamide,
308. 1,2-dibutyl-N-(2-chlorophenyl)-1,4-dihydro-6-methyl-4-oxo-3-pyridinecarboxamide,
309. 2-butyl-N-(2-chlorophenyl)-1,4-dihydro-6-methyl-4-oxo-1-pentyl-3-pyridinecarboxamide,
310. 2-butyl-N-(2-chlorobenzyl)-1-hexyl-1,4-dihydro-6-methyl-4-oxo-3-pyridinecarboxamide,
311. 2-butyl-N-(2-chlorobenzyl)-1,4-dihydro-6-methyl-4-oxo-1-phenylmethyl-3-pyridinecarboxamide,
312. 2-butyl-N-(2-chlorobenzyl)-1,4-dihydro-6-methyl-1-(4-methylphenylmethyl)-4-oxo-3-pyridinecarboxamide,
313. 2-butyl-N-(2-chlorophenyl)-1-(4-chlorophenylmethyl)-1,4-dihydro-6-methyl-4-oxo-3-pyridinecarboxamide,
314. 2-butyl-N-(2-chlorophenyl)-1-cyclohexylmethyl-1,4-dihydro-6-methyl-4-oxo-3-pyridinecarboxamide,
315. 2-butyl-N-(2-chlorophenyl)-1-(2-furylmethyl)-1,4-dihydro-6-methyl-4-oxo-3-pyridinecarboxamide,
316. 2-butyl-N-(2-chlorophenyl)-1,4-dihydro-6-methyl-4-oxo-1-(2-pyridylmethyl)-3-pyridinecarboxamide,
317. 2-butyl-N-(2-chlorophenyl)-1,4-dihydro-6-methyl-4-oxo-1-(3-pyridylmethyl)-3-pyridinecarboxamide,
318. 2-butyl-N-(2-chlorophenyl)-1,4-dihydro-6-methyl-4-oxo-1-(4-pyridylmethyl)-3-pyridinecarboxamide,
319. 1-butyl-N-(2-chlorophenyl)-1,4-dihydro-6-methyl-2-(2-methylpropyl)-4-oxo-3-pyridinecarboxamide,
320. N-(2-chlorophenyl)-1,4-dihydro-6-methyl-2-(2-methylpropyl)-4-oxo-1-pentyl-3-pyridinecarboxamide,
321. N-(2-chlorophenyl)-1-hexyl-1,4-dihydro-6-methyl-2-(2-methylpropyl)-4-oxo-3-pyridinecarboxamide,
322. N-(2-chlorophenyl)-1,4-dihydro-6-methyl-2-(2-methylpropyl)-4-oxo-1-phenylmethyl-3-pyridinecarboxamide,
323. N-(2-chlorophenyl)-1,4-dihydro-6-methyl-1-(4-methylphenylmethyl)-2-(2methylpropyl)-4-oxo-3-pyridinecarboxamide,
324. N-(2-chlorophenyl)-1-(4-chlorophenylmethy)-1,4-dihydro-6-methyl-2-(2-methylpropyl)-4-oxo-3-pyridinecarboxamide,
325. N-(2-chlorophenyl)-1-cyclohexylmethyl-1,4-dihydro-6-methyl-2-(2-methylpropyl)-4-oxo-3-pyridinecarboxamide,
326. N-(2-chlorophenyl)-1-(2-furylmethyl)-1,4-dihydro-6-methyl-2-(2-methylpropyl)-4-oxo-3-pyridinecarboxamide,
327. N-(2-chlorophenyl)-1,4-dihydro-6-methyl-2-(2-methylpropyl)-4-oxo-1-(2-pyridylmethyl)-3-pyridinecarboxamide,
328. N-(2-chlorophenyl)-1,4-dihydro-6-methyl-2-(2-methylpropyl)-4-oxo-1-(3-pyridylmethyl)-3-pyridinecarboxamide,
329. N-(2-chlorophenyl)-1,4-dihydro-6-methyl-2-(2-methylpropyl)-4-oxo-1-(4-pyridylmethyl)-3-pyridinecarboxamide,
330. 1-butyl-4-N-(2-chlorophenyl)-1,4-dihydro-6-methyl-4-oxo-2-pentyl-3-pyridinecarboxamide,
331. N-(2-chlorophenyl)-1,4-dihydro-6-methyl-4-oxo-1,2-dipentyl-3-pyridinecarboxamide,
332. N-(2-chlorophenyl)-1-hexyl-1,4-dihydro-6-methyl-4-oxo-2-pentyl-3-pyridinecarboxamide,
333. N-(2-chlorophenyl)-1,4-dihydro-6-methyl-4-oxo-2-pentyl-1-phenylmethyl-3-pyridinecarboxamide,
334. N-(2-chlorophenyl)-1,4-dihydro-6-methyl-1-(4-methylphenylmethyl)-4-oxo-2-pentyl-3-pyridinecarboxamide, 335. N-(2-chlorophenyl)-1-(4-chlorophenylmethyl)-1,4-dihydro-6-methyl-4-oxo-2-pentyl-3-pyridinecarboxamide,
336. N-(2-chlorophenyl)-1-cyclohexylmethyl-1,4-dihydro-6-methyl-4-oxo-2-pentyl-3-pyridinecarboxamide,
337. N-(2-chlorophenyl)-1-(2-furylmethyl)-1,4-dihydro-6-methyl-4-oxo-2-pentyl-3-pyridinecarboxamide,
338. N-(2-chlorophenyl)-1,4-dihydro-6-methyl-4-oxo-2-pentyl-1-(2-pyridylmethyl)-3-pyridinecarboxamide,
339. N-(2-chlorophenyl)-1,4-dihydro-6-methyl-4-oxo-2-pentyl-1-(3-pyridylmethyl)-3-pyridinecarboxamide,
340. N-(2-chlorophenyl)-1,4-dihydro-6-methyl-4-oxo-2-pentyl-1-(4-pyridylmethyl)-3-pyridinecarboxamide,
341. N-(2-chlorophenyl)-1,4-dihydro-6-methyl-4-oxo-1-pentyl-2-phenyl-3-pyridinecarboxamide,
342. N-(2-chlorophenyl)-1-hexyl-1,4-dihydro-6-methyl-4-oxo-2-phenyl-3-pyridinecarboxamide,
343. N-(2-chlorophenyl)-1,4-dihydro-6-methyl-4-oxo-2-phenyl-1-phenylmethyl-3-pyridinecarboxamide,
344. N-(2-chlorophenyl)-1,4-dihydro-6-methyl-1-(4-methylphenyl)-4-oxo-2-phenyl-3-pyridinecarboxamide,
345. N-(2-chlorophenyl)-1-(4-chlorophenylmethyl)-1,4-dihydro-6-methyl-4-oxo-2-phenyl-3-pyridinecarboxamide,
346. N-(2-chlorophenyl)-1-cyclohexylmethyl-1,4-dihydro-6-methyl-4-oxo-2-phenyl-3-pyridinecarboxamide,
347. N-(2-chlorophenyl)-1-(2-furylmethyl)-1,4-dihydro-6-methyl-4-oxo-2-phenyl-3-pyridinecarboxamide,
348. N-(2-chlorophenyl)-1,4-dihydro-6-methyl-4-oxo-2-phenyl-1-(2-pyridylmethyl)-3-pyridinecarboxamide,
346. N-(2-chlorophenyl)-1,4-dihydro-6-methyl-4-oxo-2-phenyl-1-(3-pyridylmethyl)-3-pyridinecarboxamide,
350. N-(2-chlorophenyl)-1,4-dihydro-6-methyl-4-oxo-2-phenyl-1-(4-pyridylmethyl)-3-pyridinecarboxamide,
351. 1-butyl-N,2-bis(2-chlorophenyl)-1,4-dihydro-6-methyl-4-oxo-3-pyridinecarboxamide,
352. N,2-bis(2-chlorophenyl)-1,4-dihydro-6-methyl-4-oxo-1-pentyl-3-pyridinecarboxamide,
353. N,2-bis(2-chlorophenyl)-1-hexyl-1,4-dihydro-6-methyl-4-oxo-3-pyridinecarboxamide,
354. N,2-bis(2-chlorophenyl)-1,4-dihydro-6-methyl-4-oxo-1-phenylmethyl-3-pyridinecarboxamide,
355. N,2-bis(2-chlorophenyl)-1,4-dihydro-6-methyl-1-(4-methylphenylmethyl)-4-oxo-3-pyridinecarboxamide,
356. N,2-bis(2-chlorophenyl)-1-(4-chlorophenylmethyl)-1,4-dihydro-6-methyl-4-oxo-3-pyridinecarboxamide,
357. N,2-bis(2-chlorophenyl)-1-cyclohexylmethyl-1,4-dihydro-6-methyl-4-oxo-3-pyridinecarboxamide,
358. N,2-bis(2-chlorophenyl)-1-(2-furylmethyl)-1,4-dihydro-6-methyl-4-oxo-3-pyridinecarboxamide,
359. N,2-bis(2-chlorophenyl)-1,4-dihydro-6-methyl-4-oxo-1-(2-pyridylmethyl)-3-pyridinecarboxamide,
360. N,2-bis(2-chlorophenyl)-1,4-dihydro-6-methyl-4-oxo-1-(3-pyridylmethyl)-3-pyridinecarboxamide,
361. N,2-bis(2-chlorophenyl)-1,4-dihydro-6-methyl-4-oxo-1-(4-pyridylmethyl)-3-pyridinecarboxamide,
362. 1-butyl-N-(2-chlorophenyl)-2-(3-chlorophenyl)-1,4-dihydro-6-methyl-4-oxo-3-pyridinecarboxamide,
363. N-(2-chlorophenyl)-2-(3-chlorophenyl)-1,4-dihydro-6-methyl-4-oxo-1-pentyl-3-pyridinecarboxamide,
364. N-(2-chlorophenyl)-2-(3-chlorophenyl)-1-hexyl-1,4-dihydro-6-methyl-4-oxo-3-pyridinecarboxamide,
365. N-(2-chlorophenyl)-2-(3-chlorophenyl)-1,4-dihydro-6-methyl-4-oxo-1-phenylmethyl-3-pyridinecarboxamide,
366. N-(2-chlorophenyl)-2-(3-chlorophenyl)-1,4-dihydro-6-methyl-1-(4-methylphenylmethyl)-4-oxo-3-pyridinecarboxamide,
367. N-(2-chlorophenyl)-2-(3-chlorophenyl)-1-1-(4-chlorophenylmethyl)-1,4-dihydro-6-methyl-4-oxo-3-pyridinecarboxamide,
368. N-(2-chlorophenyl)-2-(3-chlorophenyl)-1-cyclohexylmethyl-1,4-dihydro-6-methyl-4-oxo-3-pyridinecarboxamide,
369. N-(2-chlorophenyl)-2-(3-chlorophenyl)-1-(2-furylmethyl)-1,4-dihydro-6-methyl-4-oxo-3-pyridinecarboxamide,
370. N-(2-chlorophenyl)-2-(3-chlorophenyl)-1,4-dihydro-6-methyl-4-oxo-1-(2-pyridylmethyl)-3-pyridinecarboxamide,
371. N-(2-chlorophenyl)-2-(3-chlorophenyl)-1,4-dihydro-6-methyl-4-oxo-1-(3-pyridylmethyl)-3-pyridinecarboxamide,
372. N-(2-chlorophenyl)-2-(3-chlorophenyl)-1,4-dihydro-6-methyl-4-oxo-1-(4-pyridylmethyl)-3-pyridinecarboxamide,
373. 1-butyl-N-(2-chlorophenyl)-1,4-dihydro-6-methyl-2-(2-methylphenyl)-4-oxo-3-pyridinecarboxamide,
374. N-(2-chlorophenyl)-1,4-dihydro-6-methyl-2-(2-methylphenyl)-4-oxo-1-pentyl-3-pyridinecarboxamide,
375. N-(2-chlorophenyl)-1-hexyl-1,4-dihydro-6-methyl-2-(2-methylphenyl)-4-oxo-3-pyridinecarboxamide,
376. N-(2-chlorophenyl)-1,4-dihydro-6-methyl-2-(2-methylphenyl)-4-oxo-1-phenylmethyl-3-pyridinecarboxamide,
377. N-(2-chlorophenyl)-1,4-dihydro-6-methyl-2-(2-methylphenyl)-1-(4-methylphenylmethyl)-4-oxo-3-pyridinecarboxamide,
378. N-(2-chlorophenyl)-1-(4-chlorophenylmethyl)-1,4-dihydro-6-methyl-2-(2-methylphenyl)-4-oxo-3-pyridinecarboxamide,
379. N-(2-chlorophenyl)-1-cyclohexylmethyl-1,4-dihydro-6-methyl-2-(2-methylphenyl)-4-oxo-3-pyridinecarboxamide,
380. N-(2-chlorophenyl)-1-(2-furylmethyl)-1,4-dihydro-6-methyl-2-(2-methylphenyl)-4-oxo-3-pyridinecarboxamide,
381. N-(2-chlorophenyl)-1,4-dihydro-6-methyl-2-(2-methylphenyl)-4-oxo-1-(2-pyridylmethyl)-3-pyridinecarboxamide,
382. N-(2-chlorophenyl)-1,4-dihydro-6-methyl-2-(2-methylphenyl)-4-oxo-1-(3-pyridylmethyl)-3-pyridinecarboxamide,
383. N-(2-chlorophenyl)-1,4-dihydro-6-methyl-2-(2-methylphenyl)-4-oxo-1-(4-pyridylmethyl)-3-pyridinecarboxamide,
384. 1-butyl-N-(2-chlorophenyl)-1,4-dihydro-6-methyl-2-(3-methylphenyl)-4-oxo-3-pyridinecarboxamide,
385. N-(2-chlorophenyl)-1,4-dihydro-6-methyl-2-(3-methylphenyl)-4-oxo-1-pentyl-3-pyridinecarboxamide,
386. N-(2-chlorophenyl)-1-hexyl-1,4-dihydro-6-methyl-2-(3-methylphenyl)-4-oxo-3-pyridinecarboxamide,
387. N-(2-chlorophenyl)-1,4-dihydro-6-methyl-2-(3-methylphenyl)-4-oxo-1-phenylmethyl-3-pyridinecarboxamide,
388. N-(2-chlorophenyl)-1,4-dihydro-6-methyl-2-(3-methylphenyl)-1-(4-methylphenylmethyl)-4-oxo-3-pyridinecarboxamide, 389. N-(2-chlorophenyl)-1-(4-chlorophenylmethyl)-1,4-dihydro-6-methyl-2-(3-methylphenyl)-4-oxo-3-pyridinecarboxamide,
390. N-(2-chlorophenyl)-1-cyclohexylmethyl-1,4-dihydro-6-methyl-2-(3-methylphenyl)-4-oxo-3-pyridinecarboxamide,
391. N-(2-chlorophenyl)-1-(2-furylmethyl)-1,4-dihydro-6-methyl-2-(3-methylphenyl)-4-oxo-3-pyridinecarboxamide,
392. N-(2-chlorophenyl)-1,4-dihydro-6-methyl-2-(3-methylphenyl)-4-oxo-1-(2-pyridylmethyl)-3-pyridinecarboxamide,
393. N-(2-chlorophenyl)-1,4-dihydro-6-methyl-2-(3-methylphenyl)-4-oxo-1-(3-pyridylmethyl)-3-pyridinecarboxamide,
394. N-(2-chlorophenyl)-1,4-dihydro-6-methyl-2-(3-methylphenyl)-4-oxo-1-(4-pyridylmethyl)-3-pyridinecarboxamide,
395. 1-butyl-N-(2-chlorophenyl)-2-(2-furyl)-1,4-dihydro-6-methyl-4-oxo-3-pyridinecarboxamide,
396. N-(2-chlorophenyl)-2-(2-furyl)-1,4-dihydro-6-methyl-4-oxo-1-pentyl-3-pyridinecarboxamide,
397. N-(2-chlorophenyl)-2-(2-furyl)-1-hexyl-1,4-dihydro-6-methyl-4-oxo-3-pyridinecarboxamide,
398. N-(2-chlorophenyl)-2-(2-furyl)-1,4-dihydro-6-methyl-4-oxo-1-phenylmethyl-3-pyridinecarboxamide,
399. N-(2-chlorophenyl)-2-(2-furyl)-1,4-dihydro-6-methyl-1-(4-methylphenylmethyl)-4-oxo-3-pyridinecarboxamide,
400. N-(2-chlorophenyl)-1-(4-chlorophenylmethyl)-2-(2-furyl)-1,4-dihydro-6-methyl-4-oxo-3-pyridinecarboxamide,
401. N-(2-chlorophenyl)-1-cyclohexylmethl-2-(2-furyl)-1,4-dihydro-6-methyl-4-oxo-3-pyridinecarboxamide,
402. N-(2-chlorophenyl)-2-(2-furyl)-1-(2-furylmethyl)-1,4-dihydro-6-methyl-4-oxo-3-pyridinecarboxamide,
403. N-(2-chlorophenyl)-2-(2-furyl)-1,4-dihydro-6-methyl-4-oxo-1-(2-pyridylmethyl)-3-pyridinecarboxamide,
404. N-(2-chlorophenyl)-2-(2-furyl)-1,4-dihydro-6-methyl-4-oxo-1-(3-pyridylmethyl)-3-pyridinecarboxamide,
405. N-(2-chlorophenyl)-2-(2-furyl)-1,4-dihydro-6-methyl-4-oxo-1-(4-pyridylmethyl)-3-pyridinecarboxamide,
406. 1-butyl-N-(2-chlorophenyl)-1,4-dihydro-6-methyl-4-oxo-2-(2-pyridyl)-3-pyridinecarboxamide,
407. N-(2-chlorophenyl)-1,4-dihydro-6-methyl-4-oxo-1-pentyl-2-(2-pyridyl)-3-pyridinecarboxamide,
408. N-(2-chlorophenyl)-1-hexyl-1,4-dihydro-6-methyl-4-oxo-2-(2-pyridyl)-3-pyridinecarboxamide,
409. N-(2-chlorophenyl)-1,4-dihydro-6-methyl-4-oxo-1-phenylmethyl-2-(2-pyridyl)-3-pyridinecarboxamide,
410. N-(2-chlorophenyl)-1,4-dihydro-6-methyl-1-(4-methylphenylmethyl)-4-oxo-2-(2-pyridyl)-3-pyridinecarboxamide,
411. N-(2-chlorophenyl)-1-(4-chlorophenylmethyl)-1,4-dihydro-6-methyl-4-oxo-2-(2-pyridyl)-3-pyridinecarboxamide,
412. N-(2-chlorophenyl)-1-cyclohexylmethyl-1,4-dihydro-6-methyl-4-oxo-2-(2-pyridyl)-3-pyridinecarboxamide,
413. N-(2-chlorophenyl)-1-(2-furylmethyl)-1,4-dihydro-6-methyl-4-oxo-2-(2-pyridyl)-3-pyridinecarboxamide,
414. N-(2-chlorophenyl)-1,4-dihydro-6-methyl-4-oxo-2-(2-pyridyl)-1-(2-pyridylmethyl)-3-pyridinecarboxamide,
415. N-(2-chlorophenyl)-1,4-dihydro-6-methyl-4-oxo-2-(2-pyridyl)-1-(3-pyridylmethyl)-3-pyridinecarboxamide,
416. N-(2-chlorophenyl)-1,4-dihydro-6-methyl-4-oxo-2-(2-pyridyl)-1-(4-pyridylmethyl)-3-pyridinecarboxamide,
417. 1-butyl-N-(2-chlorophenyl)-1,4-dihydro-6-methyl-4-oxo-2-(3-pyridyl)-3-pyridinecarboxamide,
418. N-(2-chlorophenyl)-1,4-dihydro-6-methyl-4-oxo-1-pentyl-2-(3-pyridyl)-3-pyridinecarboxamide,
419. N-(2-chlorophenyl)-1-hexyl-1,4-dihydro-6-methyl-4-oxo-2-(3-pyridyl)-3-pyridinecarboxamide,
420. N-(2-chlorophenyl)-1,4-dihydro-6-methyl-4-oxo-1-phenylmethyl-2-(3-pyridyl)-3-pyridinecarboxamide,
421. N-(2-chlorophenyl)-1,4-dihydro-6-methyl-1-(4-methylphenylmethyl)-4-oxo-2-(3-pyridyl)-3-pyridinecarboxamide,
422. N-(2-chlorophenyl)-1-(4-chlorophenylmethyl)-1,4-dihydro-6-methyl-4-oxo-2-(3-pyridyl)-3-pyridinecarboxamide,
423. N-(2-chlorophenyl)-1-cyclohexylmethyl-1,4-dihydro-6-methyl-4-oxo-2-(3-pyridyl)-3-pyridinecarboxamide,
424. N-(2-chlorophenyl)-1-(2-furylmethyl)-1,4-dihydro-6-methyl-4-oxo-2-(3-pyridyl)-3-pyridinecarboxamide,
425. N-(2-chlorophenyl)-1,4-dihydro-6-methyl-4-oxo-2-(3-pyridyl)-1-(2-pyridylmethyl)-3-pyridinecarboxamide,
426. N-(2-chlorophenyl)-1,4-dihydro-6-methyl-4-oxo-2-(3-pyridyl)-1-(3-pyridylmethyl)-3-pyridinecarboxamide,
427. N-(2-chlorophenyl)-1,4-dihydro-6-methyl-4-oxo-2-(3-pyridyl)-1-(4-pyridylmethyl)-3-pyridinecarboxamide,
428. 1-butyl-N-(2-chlorophenyl)-1,4-dihydro-6-methyl-4-oxo-2-(4-pyridyl)-3-pyridinecarboxamide,
429. N-(2-chlorophenyl)-1,4-dihydro-6-methyl-4-oxo-1-pentyl-2-(4-pyridyl)-3-pyridinecarboxamide,
430. N-(2-chlorophenyl)-1-hexyl-1,4-dihydro-6-methyl-4-oxo-2-(4-pyridyl)-3-pyridinecarboxamide,
431. N-(2-chlorophenyl)-1,4-dihydro-6-methyl-4-oxo-1-phenylmethyl-2-(4-pyridyl)-3-pyridinecarboxamide,
432. N-(2-chlorophenyl)-1,4-dihydro-6-methyl-1-(4-methylphenylmethyl)-4-oxo-2-(4-pyridyl)-3-pyridinecarboxamide,
433. N-(2-chlorophenyl)-1-(4-chlorophenylmethyl)-1,4-dihydro-6-methyl-4-oxo-2-(4-pyridyl)-3-pyridinecarboxamide,
434. N-(2-chlorophenyl)-1-cyclohexylmethyl-1,4-dihydro-6-methyl-4-oxo-2-(4-pyridyl)-3-pyridinecarboxamide,
435. N-(2-chlorophenyl)-1-(2-furylmethyl)-1,4-dihydro-6-methyl-4-oxo-2-(4-pyridyl)-3-pyridinecarboxamide,
436. N-(2-chlorophenyl)-1,4-dihydro-6-methyl-4-oxo-2-(4-pyridyl)-1-(2-pyridylmethyl)-3-pyridinecarboxamide,
437. N-(2-chlorophenyl)-1,4-dihydro-6-methyl-4-oxo-2-(4-pyridyl)-1-(3-pyridylmethyl)-3-pyridinecarboxamide,
438. N-(2-chlorophenyl)-1,4-dihydro-6-methyl-4-oxo-2-(4-pyridyl)-1-(4-pyridylmethyl)-3-pyridinecarboxamide,
439. 2-ethyl-1,4-dihydro-6-methyl-N-(2,3-dimethylphenyl)-4-oxo-1-phenylmethyl-3-pyridinecarboxamide,
440. 2-ethyl-1,4-dihydro-6-methyl-N-(2,3-dimethylphenyl)-4-oxo-1-(4-methylphenylmethyl)-3-pyridinecarboxamide, 441. 1-(4-chlorophenylmethyl)-2-ethyl-1,4-dihydro-6-methyl-N-(2,3-dimethylphenyl)-4-oxo-3-pyridinecarboxamide,
442. 1-cyclohexylmethyl-2-ethyl-1,4-dihydro-6-methyl-N-(2,3-dimethylphenyl)-4-oxo-3-pyridinecarboxamide,
443. 2-ethyl-1-(2-furylmethyl)-1,4-dihydro-6-methyl-N-(2,3-dimethylphenyl)-4-oxo-3-pyridinecarboxamide,
444. 2-ethyl-1,4-dihydro-6-methyl-N-(2,3-dimethylphenyl)-4-oxo-1-(2-pyridylmethyl)-3-pyridinecarboxamide,
445. 2-ethyl-1,4-dihydro-6-methyl-N-(2,3-dimethylphenyl)-4-oxo-1-(3-pyridylmethyl)-3-pyridinecarboxamide,
446. 2-ethyl-1,4-dihydro-6-methyl-N-(2,3-dimethylphenyl)-4-oxo-1-(4-pyridylmethyl)-3-pyridinecarboxamide,
447. 1,4-dihydro-6-methyl-N-(2,3-dimethylphenyl)-4-oxo-1-phenylmethyl-2-propyl-3-pyridinecarboxamide,
448. 1,4-dihydro-6-methyl-N-(2,3-dimethylphenyl)-1-(4-methylphenylmethyl)-4-oxo-2-propyl-3-pyridinecarboxamide,
449. 1-(4-chlorophenylmethyl)-1,4-dihydro-6-methyl-N-(2,3-dimethylphenyl)-4-oxo-2-propyl-3-pyridinecarboxamide,
450. 1-cyclohexylmethyl-1,4-dihydro-6-methyl-N-(2,3-dimethylphenyl)-4-oxo-2-propyl-3-pyridinecarboxamide,
451. 1-(2-furylmethyl)-1,4-dihydro-6-methyl-N-(2,3-dimethylphenyl)-4-oxo-2-propyl-3-pyridinecarboxamide,
452. 1,4-dihydro-6-methyl-N-(1,3-dimethylphenyl)-4-oxo-2-propyl-1-(2-pyridylmethyl)-3-pyridinecarboxamide,
453. 1,4-dihydro-6-methyl-N-(2,3-dimethylphenyl)-4-oxo-2-propyl-1-(3-pyridylmethyl)-3-pyridinecarboxamide,
454. 1,4-dihydro-6-methyl-N-(2,3-dimethylphenyl)-4-oxo-2-propyl-1-(4-pyridylmethyl)-3-pyridinecarboxamide,
455. 2-butyl-1,4-dihydro-6-methyl-N-(2,3-dimethylphenyl)-4-oxo-1-phenylmethyl-3-pyridinecarboxamide,
456. 2-butyl-1,4-dihydro-6-methyl-N-(2,3-dimethylphenyl)-1-(4-methylphenylmethyl)-4-oxo-3-pyridinecarboxamide,
457. 2-butyl-1-(4-chlorophenylmethyl)-1,4-dihydro-6-methyl-N-(2,3-dimethylphenyl)-4-oxo-3-pyridinecarboxamide,
458. 2-butyl-1-cyclohexylmethyl-1,4-dihydro-6-methyl-N-(2,3-dimethylphenyl)-4-oxo-3-pyridinecarboxamide,
459. 2-butyl-1-(2-furylmethyl)-1,4-dihydro-6-methyl-N-(2,3-dimethylphenyl)-4-oxo-3-pyridinecarboxamide,
460. 2-butyl-1,4-dihydro-6-methyl-N-(2,3-dimethylphenyl)-4-oxo-1-(2-pyridylmethyl)-3-pyridinecarboxamide,
461. 2-butyl-1,4-dihydro-6-methyl-N-(2,3-dimethylphenyl)-4-oxo-1-(3-pyridylmethyl)-3-pyridinecarboxamide,
462. 2-butyl-1,4-dihydro-6-methyl-N-(2,3-dimethylphenyl)-4-oxo-1-(4-pyridylmethyl)-3-pyridinecarboxamide,
463. 1,4-dihydro-6-methyl-N-(2,3-dimethylphenyl)-2-(2-methylpropyl)-4-oxo-3-pyridinecarboxamide,
464. 1,4-dihydro-6-methyl-N-(2,3-dimethylphenyl)-1-(4-methylphenylmethyl)-2-(2-methylpropyl)-4-oxo-3-pyridinecarboxamide,
465. 1-(4-chlorophenylmethyl)-1,4-dihydro-6-methyl-N-(2,3-dimethylphenyl)-2-(2-methylpropyl)-4-oxo-3-pyridinecarboxamide,
466. 1-cyclohexylmethyl-1,4-dihydro-6-methyl-N-(2,3-dimethylphenyl)-2-(2-methylpropyl)-4-oxo-3-pyridinecarboxamide,
467. 1-(2-furylmethyl)-1,4-dihydro-6-methyl-N-(2,3-dimethylphenyl)-2-(2-methylpropyl)-4-oxo-3-pyridinecarboxamide,
468. 1,4-dihydro-6-methyl-N-(2,3-dimethylphenyl)-2-(2-methylpropyl)-4-oxo-1-(2-pyridylmethyl)-3-pyridinecarboxamide,
469. 1,4-dihydro-6-methyl-N-(2,3-dimethylphenyl)-2-(2-methylpropyl)-4-oxo-1-(3-pyridylmethyl)-3-pyridinecarboxamide,
470. 1,4-dihydro-6-methyl-N-(2,3-dimethylphenyl)-2-(2-methylpropyl)-4-oxo-1-(4-pyridylmethyl)-3-pyridinecarboxamide,
471. 1,4-dihydro-6-methyl-N-(2,3-dimethylphenyl)-4-oxo-2-pentyl-1-phenylmethyl-3-pyridinecarboxamide,
472. 1,4-dihydro-6-methyl-N-(2,3-dimethylphenyl)-1-(4-methylphenylmethyl)-4-oxo-2-pentyl-3-pyridinecarboxamide,
473. 1-(4-chlorophenylmethyl)-1,4-dihydro-6-methyl-N-(2,3-dimethylphenyl)-4-oxo-2-pentyl-3-pyridinecarboxamide,
474. 1-cyclohexylmethyl-1,4-dihydro-6-methyl-N-(2,3-dimethylphenyl)-4-oxo-2-pentyl-3-pyridinecarboxamide,
475. 1-(2-furylmethyl)-1,4-dihydro-6-methyl-N-(2,3-dimethylphenyl)-4-oxo-2-pentyl-3-pyridinecarboxamide,
476. 1,4-dihydro-6-methyl-N-(2,3-dimethylphenyl)-4-oxo-2-pentyl-1-(2-pyridylmethyl)-3-pyridinecarboxamide,
477. 1,4-dihydro-6-methyl-N-(2,3-dimethylphenyl)-4-oxo-2-pentyl-1-(3-pyridylmethyl)-3-pyridinecarboxamide,
478. 1,4-dihydro-6-methyl-N-(2,3-dimethylphenyl)-4-oxo-2-pentyl-1-(4-pyridylmethyl)-3-pyridinecarboxamide,
479. 1,4-dihydro-6-methyl-N-(2,3-dimethylphenyl)-1-(4-methylphenylmethyl)-4-oxo-2-phenyl-3-pyridinecarboxamide,
480. 1-(4-chlorophenylmethyl)-1,4-dihydro-6-methyl-N-(2,3-dimethylphenyl)-4-oxo-2-phenyl-3-pyridinecarboxamide,
481. 1-cyclohexylmethyl-1,4-dihydro-6-methyl-N-(2,3-dimethylphenyl)-4-oxo-2-phenyl-3-pyridinecarboxamide,
482. 1-(2-furylmethyl)-1,4-dihydro-6-methyl-N-(2,3-dimethylphenyl)-4-oxo-2-phenyl-3-pyridinecarboxamide,
483. 1,4-dihydro-6-methyl-N-(2,3-dimethylphenyl)-4-oxo-2-phenyl-1-(2-pyridylmethyl)-3-pyridinecarboxamide,
484. 1,4-dihydro-6-methyl-N-(2,3-dimethylphenyl)-4-oxo-2-phenyl)-1-(3-pyridylmethyl)-3-pyridinecarboxamide,
485. 1,4-dihydro-6-methyl-N-(2,3-dimethylphenyl)-4-oxo-2-phenyl-1-(4-pyridylmethyl)-3-pyridinecarboxamide, 486. 2-(2-chlorophenyl)-1,4-dihydro-6-methyl-N-(2,3-dimethylphenyl)-4-oxo-1-phenylmethyl-3-pyridinecarboxamide,
487. 2-(2-chlorophenyl)-1,4-dihydro-6-methyl-N-(2,3-dimethylphenyl)-1-(4-methylphenylmethyl)-4-oxo-3-pyridinecarboxamide,
488. 2-(2-chlorophenyl)-1-(4-chlorophenylmethyl)-1,4-dihydro-6-methyl-N-(2,3-dimethylphenyl)-4-oxo-3-pyridinecarboxamide,
489. 2-(2-chlorophenyl)-1-cyclohexylmethyl-1,4-dihydro-6-methyl-N-(2,3-dimethylphenyl)-4-oxo-3-pyridinecarboxamide,
490. 2-(2-chlorophenyl)-1-(2-furylmethyl)-1,4-dihydro-6-methyl-N-(2,3-dimethylphenyl)-4-oxo-3-pyridinecarboxamide,
491. 2-(2-chlorophenyl)-1,4-dihydro-6-methyl-N-(2,3-dimethylphenyl)-4-oxo-1-(2-pyridylmethyl)-3-pyridinecarboxamide,
492. 2-(2-chlorophenyl)-1,4-dihydro-6-methyl-N-(2,3-dimethylphenyl)-4-oxo-1-(3-pyridylmethyl)-3-pyridinecarboxamide,
493. 2-(2-chlorophenyl)-1,4-dihydro-6-methyl-N-(2,3-dimethylphenyl)-4-oxo-1-(4-pyridylmethyl)-3-pyridinecarboxamide,
494. 2-(3-chlorophenyl)-1,4-dihydro-6-methyl-N-(2,3-dimethylphenyl)-4-oxo-1-phenylmethyl-3-pyridinecarboxamide,
495. 2-(3-chlorophenyl)-1,4-dihydro-6-methyl-N-(2,3-dimethylphenyl)-1-(4-methylphenylmethyl)-4-oxo-3-pyridinecarboxamide,
496. 2-(3-chlorophenyl)-1-(4-chlorophenylmethyl)-1,4-dihydro-6-methyl-N-(2,3-dimethylphenyl)-4-oxo-3-pyridinecarboxamide,
497. 2-(3-chlorophenyl)-1-cyclohexylmethyl-1,4-dihydro-6-methyl-N-(2,3-dimethylphenyl)-4-oxo-3-pyridinecarboxamide,
498. 2-(3-chlorophenyl)-1-(2-furylmethyl)-1,4-dihydro-6-methyl-N-(2,3-dimethylphenyl)-4-oxo-3-pyridinecarboxamide,
499. 2-(3-chlorophenyl)-1,4-dihydro-6-methyl-N-(2,3-dimethylphenyl)-4-oxo-1-(2-pyridylmethyl)-3-pyridinecarboxamide,
500. 2-(3-chlorophenyl)-1,4-dihydro-6-methyl-N-(2,3-dimethylphenyl)-4-oxo-1-(3-pyridylmethyl)-3-pyridinecarboxamide,
501. 2-(3-chlorophenyl)-1,4-dihydro-6-methyl-N-(2,3-dimethylphenyl)-4-oxo-1-(4-pyridylmethyl)-3-pyridinecarboxamide,
502. 1,4-dihydro-6-methyl-2-(2-methylphenyl)-N-(2,3-dimethylphenyl)-4-oxo-1-phenylmethyl-3-pyridinecarboxamide,
503. 1,4-dihydro-6-methyl-2-(2-methylphenyl)-N-(2,3-dimethylphenyl)-1-(4-methylphenylmethyl)-4-oxo-3-pyridinecarboxamide,
504. 1-(4-chlorophenylmethyl)-1,4-dihydro-6-methyl-2-(2-methylphenyl)-N-(2,3-dimethylphenyl)-4-oxo-3-pyridinecarboxamide,
505. 1-cyclohexylmethyl-1,4-dihydro-6-methyl-2-(2-methylphenyl)-N-(2,3-dimethylphenyl)-4-oxo-3-pyridinecarboxamide,
506. 1-(2-furylmethyl)-1,4-dihydro-6-methyl-2-(2-methylphenyl)-N-(2,3-dimethylphenyl)-4-oxo-3-pyridinecarboxamide,
507. 1,4-dihydro-6-methyl-2-(2-methylphenyl)-N-(2,3-dimethylphenyl)-4-oxo-1-(2-pyridylmethyl)-3-pyridinecarboxamide,
508. 1,4-dihydro-6-methyl-2-(2-methylphenyl)-N-(2,3-dimethylphenyl)-4-oxo-1-(3-pyridylmethyl)-3-pyridinecarboxamide,
509. 1,4-dihydro-6-methyl-2-(2-methylphenyl)-N-(2,3-dimethylphenyl)-4-oxo-1-(4-pyridylmethyl)-3-pyridinecarboxamide,
510. 1,4-dihydro-6-methyl-2-(3-methylphenyl)-N-(2,3-dimethylphenyl)-4-oxo-1-phenylmethyl-3-pyridinecarboxamide,
511. 1,4-dihydro-6-methyl-2-(3-methylphenyl)-N-(2,3-dimethylphenyl)-1-(4-methylphenylmethyl)-4-oxo-3-pyridinecarboxamide,
512. 1-(4-chlorophenylmethyl)-1,4-dihydro-6-methyl-2-(3-methylphenyl)-N-(2,3-dimethylphenyl)-4-oxo-3-pyridinecarboxamide,
513. 1-cyclohexylmethyl-1,4-dihydro-6-methyl-2-(3-methylphenyl)-N-(2,3-dimethylphenyl)-4-oxo-3-pyridinecarboxamide,
514. 1-(2-furylmethyl)-1,4-dihydro-6-methyl-2-(3-methylphenyl)-N-(2,3-dimethylphenyl)-4-oxo-3-pyridinecarboxamide,
515. 1,4-dihydro-6-methyl-2-(3-methylphenyl)-N-(2,3-dimethylphenyl)-4-oxo-1-(2-pyridylmethyl)-3-pyridinecarboxamide,
516. 1,4-dihydro-6-methyl-2-(3-methylphenyl)-N-(2,3-dimethylphenyl)-4-oxo-1-(3-pyridylmethyl)-3-pyridinecarboxamide,
517. 1,4-dihydro-6-methyl-2-(3-methylphenyl)-N-(2,3-dimethylphenyl)-4-oxo-1-(4-pyridylmethyl)-3-pyridinecarboxamide,
518. 2-(2-furyl)-1,4-dihydro-6-methyl-N-(2,3-dimethylphenyl)-4-oxo-1-phenylmethyl-3-pyridinecarboxamide,
519. 2-(2-furyl)-1,4-dihydro-6-methyl-N-(2,3-dimethylphenyl)-1-(4-methylphenylmethyl)-4-oxo-3-pyridinecarboxamide,
520. 1-(4-chlorophenylmethyl)-2-(2-furyl)-1,4-dihydro-6-methyl-N-(2,3-dimethylphenyl)-4-oxo-4-oxo-3-pyridinecarboxamide,
521. 1-cyclohexylmethyl-2-(2-furyl)-1,4-dihydro-6-methyl-N-(2,3-dimethylphenyl)-4-oxo-3-pyridinecarboxamide,
522. 2-(2-furyl)-1-(2-furylmethyl)-1,4-dihydro-6-methyl-N-(2,3-dimethylphenyl)-4-oxo-3-pyridinecarboxamide,
523. 2-(2-furyl)-1,4-dihydro-6-methyl-N-(2,3-dimethylphenyl)-4-oxo-1-(2-pyridylmethyl)-3-pyridinecarboxamide,
524. 2-(2-furyl)-1,4-dihydro-6-methyl-N-(2,3-dimethylphenyl)-4-oxo-1-(3-pyridylmethyl)-3-pyridinecarboxamide,
525. 2-(2-furyl)-1,4-dihydro-6-methyl-N-(2,3-dimethylphenyl)-4-oxo-1-(4-pyridylmethyl)-3-pyridinecarboxamide,
526. 1,4-dihydro-6-methyl-N-(2,3-dimethylphenyl)-4-oxo-1-phenylmethyl-2-(2-pyridyl)-3-pyridinecarboxamide,
527. 1,4-dihydro-6-methyl-N-(2,3-dimethylphenyl)-1-(4-methylphenylmethyl)-4-oxo-2-(2-pyridyl)-3-pyridinecarboxamide,
528. 1-(4-chlorophenylmethyl)-1,4-dihydro-6-methyl-N-(2,3-dimethylphenyl)-4-oxo-2-(2-pyridyl)-3-pyridinecarboxamide,
529. 1-cyclohexylmethyl-1,4-dihydro-6-methyl-N-(2,3-dimethylphenyl)-4-oxo-2-(2-pyridyl)-3-pyridinecarboxamide, 530. 1-(2-furylmethyl)-1,4-dihydro-6-methyl-N-(2,3-dimethylphenyl)-4-oxo-2-(2-pyridyl)-3-pyridinecarboxamide,
531. 1,4-dihydro-6-methylphenyl)-4-oxo-2-(2-pyridyl)-1-(2-pyridylmethyl)-3-pyridinecarboxamide,
532. 1,4-dihydro-6-methyl-N-(2,3-dimethylphenyl)-4-oxo-2-(2-pyridyl)-1-(3-pyridylmethyl)-3-pyridinecarboxamide,
533. 1,4-dihydro-6-methyl-N-(2,3-dimethylphenyl)-4-oxo-2-(2-pyridyl)-1-(4-pyridylmethyl)-3-pyridinecarboxamide.
534. 1,4-dihydro-6-methyl-N-(2,3-dimethylphenyl)-4-oxo-1-phenylmethyl-2-(3-pyridyl)-3-pyridinecarboxamide,
535. 1,4-dihydro-6-methyl-N-(2,3-dimethylphenyl)-1-(4-methylphenylmethyl)-4-oxo-2-(3-pyridyl)-3-pyridinecarboxamide,
536. 1-(4-chlorophenylmethyl)-1,4-dihydro-6-methyl-N-(2,3-dimethylphenyl)-4-oxo-2-(3-pyridyl)-3-pyridinecarboxamide,
537. 1-cyclohexylmethyl-1,4-dihydro-6-methyl-N-(2,3-dimethylphenyl)-4-oxo-2-(3-pyridyl)-3-pyridinecarboxamide,
538. 1-(2-furylmethyl)-1,4-dihydro-6-methyl-N-(2,3-dimethylphenyl)-4-oxo-2-(3-pyridyl)-3-pyridinecarboxamide,
539. 1,4-dihydro-6-methyl-N-(2,3-dimethylphenyl)-4-oxo-2-(3-pyridyl)-1-(2-pyridylmethyl)-3-pyridinecarboxamide,
540. 1,4-dihydro-6-methyl-N-(2,3-dimethylphenyl)-4-oxo-2-(3-pyridyl)-1-(3-pyridylmethyl)-3-pyridinecarboxamide,
541. 1,4-dihydro-6-methyl-N-(2,3-dimethylphenyl)-4-oxo-2-(3-pyridyl)-1-(4-pyridylmethyl)-3-pyridinecarboxamide,
542. 1,4-dihydro-6-methyl-N-(2,3-dimethylphenyl)-4-oxo-1-phenylmethyl-2-(4-pyridyl)-3-pyridinecarboxamide,
543. 1,4-dihydro-6-methyl-N-(2,3-dimethylphenyl)-1-(4-methylphenylmethyl)-4-oxo-2-(4-pyridyl)-3-pyridinecarboxamide,
544. 1-(4-chlorophenylmethyl)-1,4-dihydro-6-methyl-N-(2,3-dimethylphenyl)-4-oxo-2-(4-pyridyl)-3-pyridinecarboxamide,
545. 1-cyclohexylmethyl-1,4-dihydro-6-methyl-N-(2,3-dimethylphenyl)-4-oxo-2-(4-pyridyl)-3-pyridinecarboxamide,
546. 1-(2-furylmethyl)-1,4-dihydro-6-methyl-N-(2,3-dimethylphenyl)-4-oxo-2-(4-pyridyl)-3-pyridinecarboxamide,
547. 1,4-dihydro-6-methyl-N-(2,3-dimethylphenyl)-4-oxo-2-(4-pyridyl)-1,2-pyridylmethyl)-3-pyridinecarboxamide,
548. 1,4-dihydro-6-methyl-N-(2,3-dimethylphenyl)-4-oxo-2-(4-pyridyl)-1-(3-pyridylmethyl)-3-pyridinecarboxamide,
549. 1,4-dihydro-6-methyl-N-(2,3-dimethylphenyl)-4-oxo-2-(4-pyridinyl)-1-(4-pyridylmethyl)-3-pyridinecarboxamide,
550. 1-butyl-2-ethyl-1,4-dihydro-6-methyl-N-(2,6-dimethylphenyl)-4-oxo-3-pyridinecarboxamide,
551. 2-ethyl-1,4-dihydro-6-methyl-N-(2,6-dimethylphenyl)-4-oxo-1-pentyl-3-pyridinecarboxamide,
552. 2-ethyl-1-hexyl-1,4-dihydro-6-methyl-N-(2,6-dimethylphenyl)-4-oxo-3-pyridinecarboxamide,
553. 2-ethyl-1,4-dihydro-1-(3-methoxypropyl)-6-methyl-N-(2,6-dimethylphenyl)-4-oxo-3-pyridinecarboxamide
554. 2-ethyl-1,4-dihydro-1-(2-methoxyethyl)-6-methyl-N-(2,6-dimethylphenyl)-4-oxo-3-pyridinecarboxamide,
555. 1-(2-ethoxyethyl)-2-ethyl-1,4-dihydro-6-methyl-N-(2,6-dimethylphenyl)-4-oxo-3-pyridinecarboxamide,
556. 1,4-dihydro-6-methyl-N-(2,6-dimethylphenyl)-4-oxo-1,2-diphenyl-3-pyridinecarboxamide,
557. 1-(2-chlorophenyl)-1,4-dihydro-6-methyl-N-(2,6-dimethylphenyl)-4-oxo-2-phenyl-3-pyridinecarboxamide,
558. 1-(3-chlorophenyl)-1,4-dihydro-6-methyl-N-(2,6-dimethylphenyl)-4-oxo-2-phenyl-3-pyridinecarboxamide,
559. 1-(4-chlorophenyl)-1,4-dihydro-6-methyl-N-(2,6-dimethylphenyl)-4-oxo-2-phenyl-3-pyridinecarboxamide,
560. 1,4-dihydro-6-methyl-1-(2-methylphenyl)-N-(2,6-dimethylphenyl)-4-oxo-2-phenyl-3-pyridinecarboxamide,
561. 1,4-dihydro-6-methyl-1-(3-methylphenyl)-N-(2,6-dimethylphenyl)-4-oxo-2-phenyl-3-pyridinecarboxamide,
562. 1,4-dihydro-6-methyl-1-(4-methylphenyl)-N-(2,6-dimethylphenyl)-4-oxo-2-phenyl-3-pyridinecarboxamide,
563. 2-(2-chlorophenyl)-1,4-dihydro-6-methyl-N-(2,6-dimethylphenyl)-4-oxo-1-phenyl-3-pyridinecarboxamide,
564. 1,2-bis(2-chlorophenyl)-1,4-dihydro-6-methyl-N-(2,6-dimethylphenyl)-4-oxo-3-pyridinecarboxamide,
565. 2-(2-chlorophenyl)-1-(3-chlorophenyl)-1,4-dihydro-6-methyl-N-(2,6-dimethylphenyl)-4-oxo-3-pyridinecarboxamide,
566. 2-(2-chlorophenyl)-1-(4-chlorophenyl)-1,4-dihydro-6-methyl-N-(2,6-dimethylphenyl)-4-oxo-3-pyridinecarboxamide,
567. 2-(3-chlorophenyl)-1,4-dihydro-6-methyl-N-(2,6-dimethylphenyl)-4-oxo-1-phenyl-3-pyridinecarboxamide,
568. 1-(2-chlorophenyl)-2-(3-chlorophenyl)-1,4-dihydro-6-methyl-N-(2,6-dimethylphenyl)-4-oxo-3-pyridinecarboxamide,
569. 2-(2-chlorophenyl)-1-(3-chlorophenyl)-1,4-dihydro-6-methyl-N-(2,6-dimethylphenyl)-4-oxo-3-pyridinecarboxamide,
570. 2-(3-chlorophenyl)-1-(4-chlorophenyl)-1,4-dihydro-6-methyl-N-(2,6-dimethylphenyl)-4-oxo-3-pyridinecarboxamide,
571. 2-(2-chlorophenyl)-1,4-dihydro-6-methyl-1-(2-methylphenyl)-N-(2,6-dimethylphenyl)-4-oxo-3-pyridinecarboxamide,
572. 2-(2-chlorophenyl)-1,4-dihydro-6-methyl-1-(3-methylphenyl)-N-(2,6-dimethylphenyl)-4-oxo-3-pyridinecarboxamide,
573. 2-(2-chlorophenyl)-1,4-dihydro-6-methyl-1-(4-methylphenyl)-N-(2,6-dimethylphenyl)-4-oxo-3-pyridinecarboxamide,
574. 2-(3-chlorophenyl)-1,4-dihydro-6-methyl-1-(2-methylphenyl)-N-(2,6-dimethylphenyl)-4-oxo-3-pyridinecarboxamide,
575. 2-(3-chlorophenyl)-1,4-dihydro-6-methyl-1-(3-methylphenyl)-N-(2,6-dimethylphenyl)-4-oxo-3-pyridinecarboxamide,
576. 2-(3-chlorophenyl)-1,4-dihydro-6-methyl-1-(4-methylphenyl)-N-(2,6-dimethylphenyl)-4-oxo-3-pyridinecarboxamide, 577. 1,4-dihydro-6-methyl-2-(2-methylphenyl)-N-(2,6-dimethylphenyl)-4-oxo-1-phenyl-3-pyridinecarboxamide,
578. 1-(2-chlorophenyl)-1,4-dihydro-6-methyl-2-(2-methylphenyl)-N-(2,6-dimethylphenyl)-4-oxo-3-pyridinecarboxamide,
579. 1-(3-chlorophenyl)-1,4-dihydro-6-methyl-2-(2-methylphenyl)-N-(2,6-dimethylphenyl)-4-oxo-3-pyridinecarboxamide,
580. 1-(4-chlorophenyl)-1,4-dihydro-6-methyl-2-(2-methylphenyl)-N-(2,6-dimethylphenyl)-4-oxo-3-pyridinecarboxamide,
581. 1,4-dihydro-6-methyl-1,2-bis(2-methylphenyl)-N-(2,6-dimethylphenyl)-4-oxo-3-pyridinecarboxamide,
582. 1,4-dihydro-6-methyl-2-(2-methylphenyl)-1-(3-methylphenyl)-N-(2,6-dimethylphenyl)-4-oxo-3-pyridinecarboxamide,
583. 1,4-dihydro-6-methyl-2-(2-methylphenyl)-1-(4-methylphenyl)-N-(2,6-dimethylphenyl)-4-oxo-3-pyridinecarboxamide,
584. 1,4-dihydro-6-methyl-2-(3-methylphenyl)-N-(2,6-dimethylphenyl)-4-oxo-1-phenyl-3-pyridinecarboxamide,
585. 1-(2-chlorophenyl)-1,4-dihydro-6-methyl-2-(3-methylphenyl)-N-(2,6-dimethylphenyl)-4-oxo-3-pyridinecarboxamide,
586. 1-(3-chlorophenyl)-1,4-dihydro-6-methyl-2-(3-methylphenyl)-N-(2,6-dimethylphenyl)-4-oxo-3-pyridinecarboxamide,
587. 1-(4-chlorophenyl)-1,4-dihydro-6-methyl-2-(3-methylphenyl)-N-(2,6-dimethylphenyl)-4-oxo-3-pyridinecarboxamide,
588. 1,4-dihydro-6-methyl-1-(2-methylphenyl)-2-(3-methylphenyl)-N-(2,6-dimethylphenyl)-4-oxo-3-pyridinecarboxamide,
589. 1,4-dihydro-6-methyl-1,2-bis(3-methylphenyl)-N-(2,6-dimethylphenyl)-4-oxo-3-pyridinecarboxamide,
590. 1,4-dihydro-6-methyl-2-(3-methylphenyl)-1-(4-methylphenyl)-N-(2,6-dimethylphenyl)-4-oxo-3-pyridinecarboxamide,
591. 2-(2-furyl)-1,4-dihydro-6-methyl-N-(2,3-dimethylphenyl)-4-oxo-1-phenyl-3-pyridinecarboxamide,
592. 1-(2-chlorophenyl)-2-(2-furyl)-1,4-dihydro-6-methyl-N-(2,6-dimethylphenyl)-4-oxo-3-pyridinecarboxamide,
593. 1-(3-chlorophenyl)-2-(2-furyl)-1,4-dihydro-6-methyl-N-(2,6-dimethylphenyl)-4-oxo-3-pyridinecarboxamide,
594. 1-(4-chlorophenyl)-2-(2-furyl)-1,4-dihydro-6-methyl-N-(2,6-dimethylphenyl)-4-oxo-3-pyridinecarboxamide,
595. 2-(2-furyl)-1,4-dihydro-6-methyl-1-(2-methylphenyl)-N-(2,6-dimethylphenyl)-4-oxo-3-pyridinecarboxamide,
596. 2-(2-furyl)-1,4-dihydro-6-methyl-1-(3-methylphenyl)-N-(2,6-dimethylphenyl)-4-oxo-3-pyridinecarboxamide,
597. 2-(2-furyl)-1,4-dihydro-6-methyl-1-(4-methylphenyl)-N-(2,6-dimethylphenyl)-4-oxo-3-pyridinecarboxamide,
598. 1,4-dihydro-6-methyl-N-(2,6-dimethylphenyl)-4-oxo-1-phenyl-2-(2-pyridyl)-3-pyridinecarboxamide,
599. 1-(2-chlorophenyl)-1,4-dihydro-6-methyl-N-(2,6-dimethylphenyl)-4-oxo-2-(2-pyridyl)-3-pyridinecarboxamide,
600. 1-(3-chlorophenyl)-1,4-dihydro-6-methyl-N-(2,6-dimethylphenyl)-4-oxo-2-(2-pyridyl)-3-pyridinecarboxamide,
601. 1-(4-chlorophenyl)-1,4-dihydro-6-methyl-N-(2,6-dimethylphenyl)-4-oxo-2-(2-pyridyl)-3-pyridinecarboxamide,
602. 1,4-dihydro-6-methyl-1-(2-methylphenyl)-N-(2,6-dimethylphenyl)-4-oxo-2-(2-pyridyl)-3-pyridinecarboxamide,
603. 1,4-dihydro-6-methyl-1-(3-methylphenyl)-N-(2,6-dimethylphenyl)-4-oxo-2-(2-pyridyl)-3-pridinecarboxamide,
604. 1,4-dihydro-6-methyl-1-(4-methylphenyl)-N-(2,6-dimethylphenyl)-4-oxo-2-(2-pyridyl)-3-pyridinecarboxamide,
605. 1,4-dihydro-6-methyl-N-(2,6-dimethylphenyl)-4-oxo-1-phenyl-2-(3-pyridyl)-3-pyridinecarboxamide,
606. 1-(2-chlorophenyl)-1,4-dihydro-6-methyl-N-(2,6-dimethylphenyl)-4-oxo-2-(3-pyridyl)-3-pyridinecarboxamide,
607. 1-(3-chlorophenyl)-1,4-dihydro-6-methyl-N-(2,6-dimethylphenyl)-4-oxo-2-(3-pyridyl)-3-pyridinecarboxamide,
608. 1-(4-chlorophenyl)-1,4-dihydro-6-methyl-N-(2,6-dimethylphenyl)-4-oxo-2-(3-pyridyl)-3-pyridinecarboxamide,
609. 1,4-dihydro-6-methyl-1-(2-methylphenyl)-N-(2,6-dimethylphenyl)-4-oxo-2-(3-pyridyl)-3-pyridinecarboxamide,
610. 1,4-dihydro-6-methyl-1-(3-methylphenyl)-N-(2,6-dimethylphenyl)-4-oxo-2-(3-pyridyl)-3-pyridinecarboxamide,
611. 1,4-dihydro-6-methyl-1-(4-methylphenyl)-N-(2,6-dimethylphenyl)-4-oxo-2-(3-pyridyl)-3-pyridinecarboxamide,
612. 1,4-dihydro-6-methyl-N-(2,6-dimethylphenyl)-4-oxo-1-phenyl-2-(4-pyridyl)-3-pyridinecarboxamide,
613. 1-(2-chlorophenyl)-1,4-dihydro-6-methyl-N-(2,6-dimethylphenyl)-4-oxo-2-(4-pyridyl)-3-pyridinecarboxamide,
614. 1-(3-chlorophenyl)-1,4-dihydro-6-methyl-N-(2,6-dimethylphenyl)-4-oxo-2-(4-pyridyl)-3-pyridinecarboxamide,
615. 1-(4-chlorophenyl)-1,4-dihydro-6-methyl-N-(2,6-dimethylphenyl)-4-oxo-2-(4-pyridyl)-3-pyridinecarboxamide,
616. 1,4-dihydro-6-methyl-1-(2-methylphenyl)-N-(2,6-dimethylphenyl)-4-oxo-2-(4-pyridyl)-3-pyridinecarboxamide,
617. 1,4-dihydro-6-methyl-1-(3-methylphenyl)-N-(2,6-dimethylphenyl)-4-oxo-2-(4-pyridyl)-3-pyridinecarboxamide,
618. 1,4-dihydro-6-methyl-1-(4-methylphenyl)-N-(2,6-dimethylphenyl)-4-oxo-2-(4-pyridyl)-3-pyridinecarboxamide,
619. 5-bromo-1-butyl-2-ethyl-1,4-dihydro-6-methyl-N-(2,6-dimethylphenyl)-4-oxo-3-pyridinecarboxamide,
620. 5-bromo-2-ethyl-1,4-dihydro-6-methyl-N-(2,6-dimethylphenyl)-4-oxo-1-pentyl-3-pyridinecarboxamide,
621. 5-bromo-2-ethyl-1-hexyl-1,4-dihydro-6-methyl-N-(2,6-dimethylphenyl)-4-oxo-3-pyridinecarboxamide,
622. 5-bromo-2-ethyl-1,4-dihydro-1-(3-methoxypropyl)-6-methyl-N-(2,6-dimethylphenyl)-4-oxo-3-pyridinecarboxamide,
623. 5-bromo-2-ethyl-1,4-dihydro-1-(2-methoxyethyl)-6-methyl-N-(2,6-dimethylphenyl)-4-oxo-3-pyridinecarboxamide,
624. 2-ethyl-N-(2,6-diethylphenyl)-1,4-dihydro-6-methyl-4-oxo-1-pentyl-3-pyridinecarboxamide, 625. 2-ethyl-N-(2,6-diethylphenyl)-1-hexyl-1,4-dihydro-6-methyl-4-oxo-3-pyridinecarboxamide,
626. 5-bromo-2-ethyl-N-(2,6-diethylphenyl)-1,4-dihydro-1-(2-methoxyethyl)-6-methyl-4-oxo-3-pyridinecarboxamide,
627. 2-ethyl-N-(2,6-diethylphenyl)-1,4-dihydro-1-(3-methoxypropyl)-6-methyl-4-oxo-3-pyridinecarboxamide,
628. 2-ethyl-N-(2,6-diethylphenyl)-1,4-dihydro-1-(2-methoxyethyl)-6-methyl-4-oxo-3-pyridinecarboxamide,
629. 1-(2-ethoxyethyl)-2-ethyl-N-(2,6-diethylphenyl)-1,4-dihydro-6-methyl-4-oxo-3-pyridinecarboxamide,
630. 1-(2-chlorophenyl)-N-(2,6-diethylphenyl)-1,4-dihydro-6-methyl-4-oxo-2-phenyl-3-pyridinecarboxamide,
631. 1-(3-chlorophenyl)-N-(2,6-diethylphenyl)-1,4-dihydro-6-methyl-4-oxo-2-phenyl-3-pyridinecarboxamide,
632. 1-(4-chlorophenyl)-N-(2,6-diethylphenyl)-1,4-dihydro-6-methyl-4-oxo-2-phenyl-3-pyridinecarboxamide,
633. N-(2,6-diethylphenyl)-1,4-dihydro-6-methyl-1-(3-methylphenyl)-4-oxo-2-phenyl-3-pyridinecarboxamide,
634. N-(2,6-diethylphenyl)-1,4-dihydro-6-methyl-1-(4-methylphenyl)-4-oxo-2-phenyl-3-pyridinecarboxamide,
635. 2-(2-chlorophenyl)-N-(2,6-diethylphenyl)-1,4-dihydro-6-methyl-4-oxo-1-phenyl-3-pyridinecarboxamide,
636. 1,2-bis(2-chlorophenyl)-N-(2,6-diethylphenyl)-1,4-dihydro-6-methyl-4-oxo-3-pyridinecarboxamide,
637. 2-(2-chlorophenyl)-1-(3-chlorophenyl)-N-(2,6-diethylphenyl)-1,4-dihydro-6-methyl-4-oxo-3-pyridinecarboxamide,
638. 2-(2-chlorophenyl)-1-(4-chlorophenyl)-N-(2,6-diethylphenyl)-1,4-dihydro-6-methyl-4-oxo-3-pyridinecarboxamide,
639. 2-(2-chlorophenyl)-N-(2,6-diethylphenyl)-1,4-dihydro-6-methyl-1-(2-methylphenyl)-4-oxo-3-pyridinecarboxamide,
640. 2-(2-chlorophenyl)-N-(2,6-diethylphenyl)-1,4-dihydro-6-methyl-1-(3-methylphenyl)-4-oxo-3-pyridinecarboxamide,
641. 2-(2-chlorophenyl)-N-(2,6-diethylphenyl)-1,4-dihydro-6-methyl-1-(4-methylphenyl)-4-oxo-3-pyridinecarboxamide,
642. 2-(3-chlorophenyl)-N-(2,6-diethylphenyl)-1,4-dihydro-6-methyl-4-oxo-1-phenyl-3-pyridinecarboxamide,
643. 1-(2-chlorophenyl)-2-(3-chlorophenyl)-N-(2,6-diethylphenyl)-1,4-dihydro-6-methyl-4-oxo-3-pyridinecarboxamide,
644. 1,2-bis(3-chlorophenyl)-N-(2,6-diethylphenyl)-1,4-dihydro-6-methyl-4-oxo-3-pyridinecarboxamide,
645. 2-(3-chlorophenyl)-1-(4-chlorophenyl)-N-(2,6-diethylphenyl)-1,4-dihydro-6-methyl-4-oxo-3-pyridinecarboxamide,
646. 2-(3-chlorophenyl)-N-(2,6-diethylphenyl)-1,4-dihydro-6-methyl-1-(2-methylphenyl)-4-oxo-3-pyridinecarboxamide,
647. 2-(3-chlorophenyl)-N-(2,6-diethylphenyl)-1,4-dihydro-6-methyl-1-(3-methylphenyl)-4-oxo-3-pyridinecarboxamide,
648. 2-(3-chlorophenyl)-N-(2,6-diethylphenyl)-1,4-dihydro-6-methyl-1-(4-methylphenyl)-4-oxo-3-pyridinecarboxamide,
649. N-(2,6-diethylphenyl)-1,4-dihydro-6-methyl-2-(2-methylphenyl)-4-oxo-1-phenyl-3-pyridinecarboxamide,
650. 1-(2-chlorophenyl)-N-(2,6-diethylphenyl)-1,4-dihydro-6-methyl-2-(2-methylphenyl)-4-oxo-3-pyridinecarboxamide,
651. 1-(3-chlorophenyl)-N-(2,6-diethylphenyl)-1,4-dihydro-6-methyl-2-(2-methylphenyl)-4-oxo-3-pyridinecarboxamide,
652. 1-(4-chlorophenyl)-N-(2,6-diethylphenyl)-1,4-dihydro-6-methyl-2-(2-methylphenyl)-4-oxo-3-pyridinecarboxamide,
653. N-(2,6-diethylphenyl)-1,4-dihydro-6-methyl-1,2-bis(2-methylphenyl)-4-oxo-3-pyridinecarboxamide,
654. N-(2,6-diethylphenyl)-1,4-dihydro-6-methyl-2-(2-methylphenyl)-1-(3-methylphenyl)-4-oxo-3-pyridinecarboxamide,
655. N-(2,6-diethylphenyl)-1,4-dihydro-6-methyl-2-(2-methylphenyl)-1-(4-methylphenyl)-4-oxo-3-pyridinecarboxamide,
656. N-(2,6-diethylphenyl)-1,4-dihydro-6-methyl-2-(3-methylphenyl)-4-oxo-1-phenyl-3-pyridinecarboxamide,
657. 1-(2-chlorophenyl)-N-(2,6-diethylphenyl)-1,4-dihydro-6-methyl-2-(3-methylphenyl)-4-oxo-3-pyridinecarboxamide,
658. 1-(3-chlorophenyl)-N-(2,6-diethylphenyl)-1,4-dihydro-6-methyl-2-(3-methylphenyl)-4-oxo-3-pyridinecarboxamide,
659. 1-(4-chlorophenyl)-N-(2,6-diethylphenyl)-1,4-dihydro-6-methyl-2-(3-methylphenyl)-4-oxo-3-pyridinecarboxamide,
660. N-(2,6-diethylphenyl)-1,4-dihydro-6-methyl-1-(2-methylphenyl)-2-(3-methylphenyl)-4-oxo-3-pyridinecarboxamide,
661. N-(2,6-diethylphenyl)-1,4-dihydro-6-methyl-1,2-bis(3-methylphenyl)-4-oxo-3-pyridinecarboxamide,
662. N-(2,6-diethylphenyl)-1,4-dihydro-6-methyl-1-(2-methylphenyl)-2-(4-methylphenyl)-4-oxo-3-pyridinecarboxamide,
663. N-(2,6-diethylphenyl)-2-(2-furyl)-1,4-dihydro-6-methyl-4-oxo-1-phenyl-3-pyridinecarboxamide,
664. 1-(2-chlorophenyl)-N-(2,6-diethylphenyl)-2-(2-furyl)-1,4-dihydro-6-methyl-4-oxo-3-pyridinecarboxamide,
665. 1-(3-chlorophenyl)-N-(2,6-diethylphenyl)-2-(2-furyl)-1,4-dihydro-6-methyl-4-oxo-3-pyridinecarboxamide,
666. 1-(4-chlorophenyl)-N-(2,6-diethylphenyl)-2-(2-furyl)-1,4-dihydro-6-methyl-4-oxo-3-pyridinecarboxamide,
667. N-(2,6-diethylphenyl)-2-(2-furyl)-1,4-dihydro-6-methyl-1-(2-methylphenyl)-4-oxo-3-pyridinecarboxamide,
668. N-(2,6-diethylphenyl)-2-(2-furyl)-1,4-dihydro-6-methyl-1-(3-methylphenyl)-4-oxo-3-pyridinecarboxamide,
669. N-(2,6-diethylphenyl)-2-(2-furyl)-1,4-dihydro-6-methyl-1-(4-methylphenyl)-4-oxo-1-phenyl-3-pyridinecarboxamide,
670. N-(2,6-diethylphenyl)-1,4-dihydro-6-methyl-4-oxo-1-phenyl)-2-(2-pyridyl)-3-pyridinecarboxamide,
671. 1-(2-chlorophenyl)-N-(2,6-diethylphenyl)-1,4-dihydro-6-methyl-4-oxo-2-(2-pyridyl)-3-pyridinecarboxamide,
672. 1-(3-chlorophenyl)-N-(2,6-diethylphenyl)-1,4-dihydro-6-methyl-4-oxo-2-(2-pyridyl)-3-pyridinecarboxamide, 673. 1-(4-chlorophenyl)-N-(2,6-diethylphenyl)-1,4-dihydro-6-methyl-4-oxo-2-(2-pyridyl)-3-pyridinecarboxamide,
674. N-(2,6-diethylphenyl)-1,4-dihydro-6-methyl-1-(2-methylphenyl)-4-oxo-2-(2-pyridyl)-3-pyridinecarboxamide,
675. N-(2,6-diethylphenyl)-1,4-dihydro-6-methyl-1-(3-methylphenyl)-4-oxo-2-(2-pyridyl)-3-pyridinecarboxamide,
676. N-(2,6-diethylphenyl)-1,4-dihydro-6-methyl-1-(4-methylphenyl)-4-oxo-2-(2-pyridyl)-3-pyridinecarboxamide,
677. N-(2,6-diethylphenyl)-1,4-dihydro-6-methyl-4-oxo-1-phenyl-2-(3-pyridyl)-3-pyridinecarboxamide,
678. 1-(2-chlorophenyl)-N-(2,6-diethylphenyl)-1,4-dihydro-6-methyl-4-oxo-2-(3-pyridyl)-3-pyridinecarboxamide,
679. 1-(3-chlorophenyl)-N-(2,6-diethylphenyl)-1,4-dihydro-6-methyl-4-oxo-2-(3-pyridyl)-3-pyridinecarboxamide,
680. 1-(4-chlorophenyl)-N-(2,6-diethylphenyl)-1,4-dihydro-6-methyl-4-oxo-2-(3-pyridyl)-3-pyridinecarboxamide,
681. N-(2,6-diethylphenyl)-1,4-dihydro-6-methyl-1-(2-methylphenyl)-4-oxo-2-(3-pyridyl)-3-pyridinecarboxamide,
682. N-(2,6-diethylphenyl)-1,4-dihydro-6-methyl-1-(3-methylphenyl)-4-oxo-2-(3-pyridyl)-3-pyridinecarboxamide,
683. N-(2,6-diethylphenyl)-1,4-dihydro-6-methyl-1-(4-methylphenyl)-4-oxo-2-(3-pyridyl)-3-pyridinecarboxamide,
684. N-(2,6-diethylphenyl)-1,4-dihydro-6-methyl-4-oxo-1-phenyl-2-(4-pyridyl)-3-pyridinecarboxamide,
685. 1-(2-chlorophenyl)-N-(2,6-diethylphenyl)-1,4-dihydro-6-methyl-4-oxo-2-(4-pyridyl)-3-pyridinecarboxamide,
686. 1-(3-chlorophenyl)-N-(2,6-diethylphenyl)-1,4-dihydro-6-methyl-4-oxo-2-(4-pyridyl)-3-pyridinecarboxamide,
687. 1-(4-chlorophenyl)-N-(2,6-diethylphenyl)-1,4-dihydro-6-methyl-4-oxo-(4-pyridyl)-3-pyridinecarboxamide,
688. N-(2,6-diethylphenyl)-1,4-dihydro-6-methyl-1-(2-methylphenyl)-4-oxo-2-(4-pyridyl)-3-pyridinecarboxamide,
689. N-(2,6-diethylphenyl)-1,4-dihydro-6-methyl-1-(3-methylphenyl)-4-oxo-2-(4-pyridyl)-3-pyridinecarboxamide,
690. N-(2,6-diethylphenyl)-1,4-dihydro-6-methyl-1-(4-methylphenyl)-4-oxo-2-(4-pyridyl)-3-pyridinecarboxamide,
691. 5-bromo-1-(2-ethoxyethyl)-2-ethyl-N-(2,6-diethylphenyl)-1,4-dihydro-6-methyl-4-oxo-3-pyridinecarboxamide,
692. 5-bromo-2-ethyl-N-(2,6-diethylphenyl)-1,4-dihydro-6-methyl-4-oxo-1-pentyl-3-pyridinecarboxamide,
693. 5-bromo-2-ethyl-N-(2,6-diethylphenyl)-1-hexyl-1,4-dihydro-6-methyl-4-oxo-1-pentyl-3-pyridinecarboxamide,
694. 5-bromo-2-ethyl-N-(2,6-diethylphenyl)-1,4-dihydro-1-(3-methoxypropyl)-6-methyl-4-oxo-3-pyridinecarboxamide,
695. 1-butyl-2-ethyl-N-(2-ethyl-6-methylphenyl)-1,4-dihydro-6-methyl-4-oxo-3-pyridinecarboxamide,
696. 2-ethyl-N-(2-ethyl-6-methylphenyl)-1,4-dihydro-6-methyl-4-oxo-1-pentyl-3-pyridinecarboxamide,
697. 2-ethyl-N-(2-ethyl-6-methylphenyl)-1-hexyl-1,4-dihydro-6-methyl-4-oxo-3-pyridinecarboxamide,
698. 2-ethyl-N-(2-ethyl-6-methylphenyl)-1,4-dihydro-1-(3-methoxypropyl)-6-methyl-4-oxo-3-pyridinecarboxamide,
699. 2-ethyl-N-(2-ethyl-6-methylphenyl)-1,4-dihydro-1-(2-methoxyethyl)-6-methyl-4-oxo-3-pyridinecarboxamide,
700. 1-(2-ethoxyethyl)-2-ethyl-N-(2-ethyl-6-methylphenyl)-1,4-dihydro-6-methyl-4-oxo-3-pyridinecarboxamide,
701. N-(2-ethyl-6-methylphenyl)-1,4-dihydro-6-methyl-4-oxo-N,1-diphenyl-3-pyridinecarboxamide,
702. 1-(2-chlorophenyl)-N-(2-ethyl-6-methylphenyl)-1,4-dihydro-6-methyl-4-oxo-2-phenyl-3-pyridinecarboxamide,
703. 1-(3-chlorophenyl)-N-(2-ethyl-6-methylphenyl)-1,4-dihydro-6-methyl-4-oxo-2-phenyl-3-pyridinecarboxamide,
704. 1-(4-chlorophenyl)-N-(2-ethyl-6-methylphenyl)-1,4-dihydro-6-methyl-4-oxo-2-phenyl-3-pyridinecarboxamide,
705. N-(2-ethyl-6-methylphenyl)-1,4-dihydro-6-methyl-1-(2-methylphenyl)-4-oxo-2-phenyl-3-pyridinecarboxamide,
706. N-(2-ethyl-6-methylphenyl)-1,4-dihydro-6-methyl-1-(3-methylphenyl)-4-oxo-2-phenyl-3-pyridinecarboxamide,
707. N-(2-ethyl-6-methylphenyl)-1,4-dihydro-6-methyl-1-(4-methylphenyl)-4-oxo-2-phenyl-3-pyridinecarboxamide,
708. 2-(2-chlorophenyl)-N-(2-ethyl-6-methylphenyl)-1,4-dihydro-6-methyl-4-oxo-1-phenyl-3-pyridinecarboxamide,
709. 1,2-bis(2-chlorophenyl)-N-(2-ethyl-6-methylphenyl)-1,4-dihydro-6-methyl-4-oxo-3-pyridinecarboxamide,
710. 2-(2-chlorophenyl)-1-(3-chlorophenyl)-N-(2-ethyl-6-methylphenyl)-1,4-dihydro-6-methyl-4-oxo-3-pyridinecarboxamide,
711. 2-(2-chlorophenyl)-1-(4-chlorophenyl)-N-(2-ethyl-6-methylphenyl)-1,4-dihydro-6-methyl-4-oxo-3-pyridinecarboxamide,
712. 2-(2-chlorophenyl)-N-(2-ethyl-6-methylphenyl)-1,4-dihydro-6-methyl-1-(2-methylphenyl)-4-oxo-3-pyridinecarboxamide,
713. 2-(2-chlorophenyl)-N-(2-ethyl-6-methylphenyl)-1,4-dihydro-6-methyl-1-(3-methylphenyl)-4-oxo-3-pyridinecarboxamide,
714. 2-(2-chlorophenyl)-N-(2ethyl-6-methylphenyl)-1,4-dihydro-6-methyl-1-(4-methylphenyl)-4-oxo-3-pyridinecarboxamide,
715. 2-(3-chlorophenyl)-N-(2-ethyl-6-methylphenyl)-1,4-dihydro-6-methyl-4-oxo-1-phenyl-3-pyridinecarboxamide,
716. 1-(2-chlorophenyl)-2-(3-chlorophenyl)-N-(2-ethyl-6-methylphenyl)-1,4-dihydro-6-methyl-4-oxo-3-pyridinecarboxamide,
717. 1,2-bis(3-chlorophenyl)-N-(2-ethyl-6-methylphenyl)-1,4-dihydro-6-methyl-4-oxo-3-pyridinecarboxamide,
718. 2-(3-chlorophenyl)-1-(4-chlorophenyl)-N-(2-ethyl-6-methylphenyl)-1,4-dihydro-6-methyl-4-oxo-3-pyridinecarboxamide,
719. 2-(3-chlorophenyl)-N-(2-ethyl-6-methylphenyl)-1,4-dihydro-6-methyl-1-(2-methylphenyl)-4-oxo-3-pyridinecarboxamide, 720. 2-(3-chlorophenyl)-N-(2-ethyl-6-methylphenyl)-1,4-dihydro-6-methyl-1-(3-methylphenyl)-4-oxo-3-pyridinecarboxamide,
721. 2-(3-chlorophenyl)-N-(2-ethyl-6-methylphenyl)-1,4-dihydro-6-methyl-1-(4-methylphenyl)-4-oxo-3-pyridinecarboxamide,
722. N-(2-ethyl-6-methylphenyl)-1,4-dihydro-6-methyl-2-(2-methylphenyl)-4-oxo-1-phenyl-3-pyridinecarboxamide,
723. 1-(2-chlorophenyl)-N-(2-ethyl-6-methylphenyl)-1,4-dihydro-6-methyl-2-(2-methylphenyl)-4-oxo-3-pyridinecarboxamide,
724. 1-(3-chlorophenyl)-N-(2-ethyl-6-methylphenyl)-1,4-dihydro-6-methyl-2-(2-methylphenyl)-4-oxo-3-pyridinecarboxamide,
725. 1-(4-chlorophenyl)-N-(2-ethyl-6-methylphenyl)-1,4-dihydro-6-methyl-2-(2-methylphenyl)-4-oxo-3-pyridinecarboxamide,
726. N-(2-ethyl-6-methylphenyl)-1,4-dihydro-6-methyl-1,2-bis(2-methylphenyl)-4-oxo-3-pyridinecarboxamide,
727. N-(2-ethyl-6-methylphenyl)-1,4-dihydro-6-methyl-2-(2-methylphenyl)-1-(3-methylphenyl)-4-oxo-3-pyridinecarboxamide,
728. N-(2-ethyl-6-methylphenyl)-1,4-dihydro-6-methyl-2-(2-methylphenyl)-1-(4-methylphenyl)-4-oxo-3-pyridinecarboxamide,
729. N-(2-ethyl-6-methylphenyl)-1,4-dihydro-6-methyl-2-(3-methylphenyl)-4-oxo-1-phenyl-3-pyridinecarboxamide,
730. 1-(2-chlorophenyl)-N-(2-ethyl-6-methylphenyl)-1,4-dihydro-6-methyl-2-(3-methylphenyl)-4-oxo-3-pyridinecarboxamide,
731. 1-(3-chlorophenyl)-N-(2-ethyl-6-methylphenyl)-1,4-dihydro-6-methyl-2-(3-methylphenyl)-4-oxo-3-pyridinecarboxamide,
732. 1-(4-chlorophenyl)-N-(2-ethyl-6-methylphenyl)-1,4-dihydro-6-methyl-2-(3-methylphenyl)-4-oxo-3-pyridinecarboxamide,
733. N-(2-ethyl-6-methylphenyl)-1,4-dihydro-6-methyl-1-(2-methylphenyl)-2-(3-methylphenyl)-4-oxo-3-pyridinecarboxamide,
734. N-(2-ethyl-6-methylphenyl)-1,4-dihydro-6-methyl-1,2-bis(3-methylphenyl)-4-oxo-3-pyridinecarboxamide,
735. N-(2-ethyl-6-methylphenyl)-1,4-dihydro-6-methyl-1-(2-methylphenyl)-2-(4-methylphenyl)-4-oxo-3-pyridinecarboxamide,
736. N-(2-ethyl-6-methylphenyl)-2-(2-furyl)-1,4-dihydro-6-methyl-4-oxo-1-phenyl-3-pyridinecarboxamide,
737. 1-(2-chlorophenyl)-N-(2-ethyl-6-methylphenyl)-2-(2-furyl)-1,4-dihydro-6-methyl-4-oxo-3-pyridinecarboxamide,
738. 1-(3-chlorophenyl)-N-(2-ethyl-6-methylphenyl)-2-(2-furyl)-1,4-dihydro-6-methyl-4-oxo-3-pyridinecarboxamide,
739. 1-(4-chlorophenyl)-N-(2-ethyl-6-methylphenyl)-2-(2-furyl)-1,4-dihydro-6-methyl-4-oxo-3-pyridinecarboxamide,
740. N-(2-ethyl-6-methylphenyl)-2-(2-furyl)-1,4-dihydro-6-methyl-1-(2-methylphenyl)-4-oxo-3-pyridinecarboxamide,
741. N-(2-ethyl-6-methylphenyl)-2-(2-furyl)-1,4-dihydro-6-methyl-1-(3-methylphenyl)-4-oxo-3-pyridinecarboxamide,
742. N-(2-ethyl-6-methylphenyl)-2-(2-furyl)-1,4-dihydro-6-methyl-1-(4-methylphenyl)-4-oxo-3-pyridinecarboxamide,
743. N-(2-ethyl-6-methylphenyl)-1,4-dihydro-6-methyl-4-oxo-1-phenyl-2-(2-pyridyl)-3-pyridinecarboxamide,
744. 1-(2-chlorophenyl)-N-(2-ethyl-6-methylphenyl)-1,4-dihydro-6-methyl-4-oxo-2-(2-pyridyl)-3-pyridinecarboxamide,
745. 1-(3-chlorophenyl)-N-(2-ethyl-6-methylphenyl)-1,4-dihydro-6-methyl-4-oxo-2-(2-pyridyl)-3-pyridinecarboxamide,
746. 1-(4-chlorophenyl)-N-(2-ethyl-6-methylphenyl)-1,4-dihydro-6-methyl-4-oxo-2-(2-pyridyl)-3-pyridinecarboxamide,
747. N-2-ethyl-6-methylphenyl)-1,4-dihydro-6-methyl-1-(2-methylphenyl)-4-oxo-2-(2-pyridyl)-3-pyridinecarboxamide,
748. N-(2-ethyl-6-methylphenyl)-1,4-dihydro-6-methyl-1-(3-methylphenyl)-4-oxo-2-(2-pyridyl)-3-pyridinecarboxamide,
749. N-(2-ethyl-6-methylphenyl)-1,4-dihydro-6-methyl-1-(4-methylphenyl)-4-oxo-2-(2-pyridyl)-3-pyridinecarboxamide,
750. N-(2-ethyl-6-methylphenyl)-1,4-dihydro-6-methyl-4-oxo-1-phenyl-2-(3-pyridyl)-3-pyridinecarboxamide,
751. 1-(2-chlorophenyl)-N-(2-ethyl-6-methylphenyl)-1,4-dihydro-6-methyl-4-oxo-2-(3-pyridyl)-3-pyridinecarboxamide,
752. 1-(3-chlorophenyl)-N-(2-ethyl-6-methylphenyl)-1,4-dihydro-6-methyl-4-oxo-2-(3-pyridyl)-3-pyridinecarboxamide,
753. 1-(4-chlorophenyl)-N-(2-ethyl-6-methylphenyl)-1,4-dihydro-6-methyl-4-oxo-2-(3-pyridyl)-3-pyridinecarboxamide,
754. N-(2-ethyl-6-methylphenyl)-1,4-dihydro-6-methyl-1-(2-methylphenyl)-4-oxo-2-(2-pyridyl)-3-pyridinecarboxamide,
755. N-(2-ethyl-6-methylphenyl)-1,4-dihydro-6-methyl-1-(3-methylphenyl)-4-oxo-2-(3-pyridyl)-3-pyridinecarboxamide,
756. N-(2-ethyl-6-methylphenyl)-1,4-dihydro-6-methyl-1-(4-methylphenyl)-4-oxo-2-(3-pyridyl)-3-pyridinecarboxamide,
757. N-(2-ethyl-6-methylphenyl)-1,4-dihydro-6-methyl-4-oxo-1-phenyl-2-(4-pyridyl)-3-pyridinecarboxamide,
758. 1-(2-chlorophenyl)-N-(2-ethyl-6-methylphenyl)-1,4-dihydro-6-methyl-4-oxo-2-(4-pyridyl)-3-pyridinecarboxamide,
759. 1-(3-chlorophenyl)-N-(2-ethyl-6-methylphenyl)-1,4-dihydro-6-methyl-4-oxo-2-(4-pyridyl)-3-pyridinecarboxamide,
760. 1-(4-chlorophenyl)-N-(2-ethyl-6-methylphenyl)-1,4-dihydro-6-methyl-4-oxo-2-(4-pyridyl)-3-pyridinecarboxamide,
761. N-(2-ethyl-6-methylphenyl)-1,4-dihydro-6-methyl-1-(2-methylphenyl)-4-oxo-2-(4-pyridyl)-3-pyridinecarboxamide,
762. N-(2-ethyl-6-methylphenyl)-1,4-dihydro-6-methyl-1-(3-methylphenyl)-4-oxo-2-(4-pyridyl)-3-pyridinecarboxamide,
763. N-(2-ethyl-6-methylphenyl)-1,4-dihydro-6-methyl-1-(4-methylphenyl)-4-oxo-2-(4-pyridyl)-3-pyridinecarboxamide,
764. 5-bromo-1-butyl-2-ethyl-N-(2-ethyl-6-methylphenyl)-1,4-dihydro-6-methyl-4-oxo-3-pyridinecarboxamide, 765. 5-bromo-2-ethyl-N-(2-ethyl-6-methylphenyl)-1,4-dihydro-6-methyl-4-oxo-1-pentyl-3-pyridinecarboxamide,
766. 5-bromo-2-ethyl-N-(2-ethyl-6-methylphenyl)-1-hexyl-1,4-dihydro-6-methyl-4-oxo-3-pyridinecarboxamide,
767. 5-bromo-2-ethyl-N-(2-ethyl-6-methylphenyl)-1,4-dihydro-1-(3-methoxypropyl)-6-methyl-4-oxo-3-pyridinecarboxamide,
768. 5-bromo-2-ethyl-N-(2-ethyl-6-methylphenyl)-1,4-dihydro-1-(2-methoxyethyl)-6-methyl-4-oxo-3-pyridinecarboxamide,
769. 6-ethyl-1,4-dihydro-2-methyl-1-(4-methylphenylmethyl)-4-oxo-N-phenyl-3-pyridinecarboxamide,
770. 1-(4-chlorophenylmethyl)-6-ethyl-1,4-dihydro-2-methyl-4-oxo-N-phenyl-3-pyridinecarboxamide,
771. 1-cyclohexylmethyl-6-ethyl-1,4-dihydro-2-methyl-4-oxo-N-phenyl-3-pyridinecarboxamide,
772. 6-ethyl-1,4-dihydro-2-methyl-N-(2-methylphenyl)-4-oxo-1-phenylmethyl-3-pyridinecarboxamide,
773. 6-ethyl-1,4-dihydro-2-methyl-N-(2-methylphenyl)-1-(4-methylphenylmethyl)-4-oxo-3-pyridinecarboxamide,
774. 1-(4-chlorophenylmethyl)-6-ethyl-1,4-dihydro-2-methyl-N-(2-methylphenyl)-4-oxo-3-pyridinecarboxamide,
775. 1-cyclohexylmethyl-6-ethyl-1,4-dihydro-2-methyl-N-(2-methylphenyl)-4-oxo-3-pyridinecarboxmide,
776. N-(2-chlorophenyl)-6-ethyl-1,4-dihydro-2-methyl-4-oxo-1-phenylmethyl-3-pyridinecarboxamide,
777. N-(2-chlorophenyl)-6-ethyl-1,4-dihydro-2-methyl-1-(4-methylphenylmethyl)-4-oxo-3-pyridinecarboxamide,
778. N-(2-chlorophenyl)-1-(4-chlorophenylmethyl)-6-ethyl-1,4-dihydro-2-methyl-4-oxo-3-pyridinecarboxamide,
779. N-(2-chlorophenyl)-1-cyclohexylmethyl-6-ethyl-1,4-dihydro-2-methyl-4-oxo-3-pyridinecarboxamide,
780. 6-ethyl-1,4-dihydro-4-oxo-N-phenyl-1-phenylmethyl-2-propyl-3-pyridinecarboxamide,
781. 6-ethyl-1,4-dihydro-1-(4-methylphenylmethyl)-4-oxo-N-phenyl-2-propyl-3-pyridinecarboxamide,
782. 1-(4-chlorophenylmethyl)-6-ethyl-1,4-dihydro-4-oxo-N-phenyl-2-propyl-3-pyridinecarboxamide,
783. 1-cyclohexylmethyl-6-ethyl-1,4-dihydro-4-oxo-N-phenyl-2-propyl-3-pyridinecarboxamide,
784. 6-ethyl-1,4-dihydro-N-(2-methylphenyl)-4-oxo-1-phenylmethyl-2-propyl-3-pyridinecarboxamide,
785. 6-ethyl-1,4-dihydro-N-(2-methylphenyl)-1-(4-methylphenylmethyl)-4-oxo-2-propyl-3-pyridinecarboxamide,
786. 1-(4-chlorophenylmethyl)-6-ethyl-1,4-dihydro-N-(2-methylphenyl)-4-oxo-2-propyl-3-pyridnecarboxamide,
787. 1-cyclohexylmethyl-6-ethyl-1,4-dihydro-N-(2-methylphenyl)-4-oxo-2-propyl-3-pyridinecarboxamide,
788. N-(2-chlorophenyl)-6-ethyl-1,4-dihydro-4-oxo-1-phenylmethyl-2-propyl-3-pyridinecarboxamide,
789. N-(2-chlorophenyl)-6-ethyl-1,4-dihydro-1-(4-methylphenylmethyl)-4-oxo-2-propyl-3-pyridinecarboxamide,
790. N-(2-chlorophenyl)-1-(4-chlorophenylmethyl)-6-ethyl-1,4-dihydro-4-oxo-2-propyl-3-pyridinecarboxamide,
791. N-(2-chlorophenyl)-1-cyclohexylmethyl-6-ethyl-1,4-dihydro-4-oxo-2-propyl-3-pyridinecarboxamide,
792. 2-butyl-6-ethyl-1,4-dihydro-4-oxo-N-phenyl-1-phenylmethyl-3-pyridinecarboxamide,
793. 2-butyl-6-ethyl-1,4-dihydro-1-(4-methylphenylmethyl)-4-oxo-N-phenyl-3-pyridinecarboxamide,
794. 2-butyl-1-(4-chlorophenylmethyl)-6-ethyl-1,4-dihydro-4-oxo-N-phenyl-3-pyridinecarboxamide,
795. 2-butyl-1-cyclohexylmethyl-6-ethyl-1,4-dihydro-4-oxo-N-phenyl-3-pyridinecarboxamide,
796. 2-butyl-6-ethyl-1,4-dihydro-N-(2-methylphenyl)-4-oxo-1-phenylmethyl-3-pyridinecarboxamide,
797. 2-butyl-6-ethyl-1,4-dihydro-N-(2-methylphenyl)-1-(4-methylphenylmethyl)-4-oxo-3-pyridinecarboxamide,
798. 2-butyl-1-(4-chlorophenylmethyl)-6-ethyl-1,4-dihydro-N-(2-methylphenyl)-4-oxo-3-pyridinecarboxamide,
799. 2-butyl-1-cyclohexylmethyl-6-ethyl-1,4-dihydro-N-(2-methylphenyl)-4-oxo-3-pyridinecarboxamide,
800. 2-butyl-N-(2-chlorophenyl)-6-ethyl-1,4-dihydro-4-oxo-1-phenylmethyl-3-pyridinecarboxamide,
801. 2-butyl-N-(2-chlorophenyl)-6-ethyl-1,4-dihydro-1-(4-methylphenylmethyl)-4-oxo-3-pyridinecarboxamide,
802. 2-butyl-N-(2-chlorophenyl)-1-(4-chlorophenylmethyl)-6-ethyl-1,4-dihydro-4-oxo-3-pyridinecarboxamide,
803. 2-butyl-N-(2-chlorophenyl)-1-cyclohexylmethyl-6-ethyl-1,4-dihydro-4-oxo-3-pyridinecarboxamide,
804. 6-ethyl-N-(2,6-diethylphenyl)-1,4-dihydro-2-methyl-4-oxo-1-pentyl-3-pyridinecarboxamide,
805. 6-ethyl-N-(2,6-diethylphenyl)-1-hexyl-1,4-dihydro-2-methyl-4-oxo-3-pyridinecarboxamide,
806. 6-ethyl-N-(2,6-diethylphenyl)-1,4-dihydro-2-methyl-4-oxo-1-phenylmethyl-3-pyridinecarboxamide,
807. 5-bromo-6-ethyl-N-(2,6-diethylphenyl)-1,4-dihydro-2-methyl-4-oxo-1-pentyl-3-pyridinecarboxamide,
808. 5-bromo-6-ethyl-N-(2,6-diethylphenyl)-1-hexyl-1,4-dihydro-2-methyl-4-oxo-3-pyridinecarboxamide,
809. 5-bromo-6-ethyl-N-(2,6-diethylphenyl)-1,4-dihydro-2-methyl-4-oxo-1-phenylmethyl-3-pyridinecarboxamide,
810. 1-butyl-6-ethyl-N-(2,6-diethylphenyl)-1,4-dihydro-2,5-dimethyl-4-oxo-3-pyridinecarboxamide,
811. 6-ethyl-N-(2,6-diethylphenyl)-1,4-dihydro-2,5-dimethyl-4-oxo-1-pentyl-3-pyridinecarboxamide,
812. 6-ethyl-N-(2,6-diethylphenyl)-1-hexyl-1,4-dihydro-2,5-dimethyl-4-oxo-3-pyridinecarboxamide,
813. 6-ethyl-N-(2,6-diethylphenyl)-1,4-dihydro-2,5-dimethyl-4-oxo-1-phenylmethyl-3-pyridinecarboxamide,
814. 6-ethyl-N-(2,6-diethylphenyl)-1,4-dihydro-2,5-dimethyl-4-oxo-1-(2-phenylmethyl)-3-pyridinecarboxamide,
815. 1-butyl-5,6-diethyl-N-(2,6-diethylphenyl)-1,4-dihydro-2-methyl-4-oxo-3-pyridinecarboxamide,
816. 5,6-diethyl-N-(2,6-diethylphenyl)-1,4-dihydro-2-methyl-4-oxo-1-pentyl-3-pyridinecarboxamide,
817. 5,6-diethyl-N-(2,6-diethylphenyl)-1-hexyl-1,4-dihydro-2-methyl-4-oxo-3-pyridinecarboxamide,
818. 5,6-diethyl-N-(2,6-diethylphenyl)-1,4-dihydro-2-methyl-4-oxo-1-phenylmethyl-3-pyridinecarboxamide,
819. 5,6-diethyl-N-(2,6-diethylphenyl)-1,4-dihydro-2-methyl-4-oxo-1-(1-phenylmethyl)-3-pyridinecarboxamide,
820. 1-butyl-6-ethyl-N-(2-ethyl-6-methylphenyl)-1,4-dihydro-2-methyl-4-oxo-3-pyridinecarboxamide, 821. 6-ethyl-N-(2-ethyl-6-methylphenyl)-1,4-dihydro-2-methyl-4-oxo-1-pentyl-3-pyridinecarboxamide,
822. 6-ethyl-N-(2-ethyl-6-methylphenyl)-1-hexyl-1,4-dihydro-2-methyl-4-oxo-3-pyridinecarboxamide,
823. 6-ethyl-N-(2-ethyl-6-methylphenyl)-1,4-dihydro-2-methyl-4-oxo-1-phenylmethyl-3-pyridinecarboxamide,
824. 6-ethyl-N-(2-ethyl-6-methylphenyl)-1,4-dihydro-2-methyl-4-oxo-1-(2-phenylethyl)-3-pyridinecarboxamide,
825. 5-bromo-1-butyl-6-ethyl-N-(2-ethyl-6-methylphenyl)-1,4-dihydro-2-methyl-4-oxo-3-pyridinecarboxamide,
826. 5-bromo-6-ethyl-N-(2-ethyl-6-methylphenyl)-1,4-dihydro-2-methyl-4-oxo-1-pentyl-3-pyridinecarboxamide,
827. 5-bromo-6-ethyl-N-(2-ethyl-6-methylphenyl)-1-hexyl-1,4-dihydro-2-methyl-4-oxo-3-pyridinecarboxamide,
828. 5-bromo-6-ethyl-N-(2-ethyl-6-methylphenyl)-1,4-dihydro-2-methyl-4-oxo-1-phenylmethyl-3-pyridinecarboxamide,
829. 5-bromo-6-ethyl-N-(2-ethyl-6-methylphenyl)-1,4-dihydro-2-methyl-4-oxo-1-(2-phenylethyl)-3-pyridinecarboxamide,
830. 1-butyl-6-ethyl-N-(2-ethyl-6-methylphenyl)-1,4-dihydro-2,5-dimethyl-4-oxo-3-pyridinecarboxamide,
831. 6-ethyl-N-(2-ethyl-6-methylphenyl)-1,4-dihydro-2,5-dimethyl-4-oxo-1-pentyl-3-pyridinecarboxamide,
832. 6-ethyl-N-(2-ethyl-6-methylphenyl)-1-hexyl-1,4-dihydro-2,5-dimethyl-4-oxo-3-pyridinecarboxamide,
833. 6-ethyl-N-(2-ethyl-6-methylphenyl)-1,4-dihydro-2,5-dimethyl-4-oxo-1-phenylmethyl-3-pyridinecarboxamide,
834. 6-ethyl-N-(2-ethyl-6-methylphenyl)-1,4-dihydro-2,5-dimethyl-4-oxo-1-(2-phenylethyl)-3-pyridinecarboxamide,
835. 1-butyl-5,6-diethyl-N-(2-ethyl-6-methylphenyl)-1,4-dihydro-2-methyl-4-oxo-3-pyridinecarboxamide,
836. 5,6-diethyl-N-(2-ethyl-6-methylphenyl)-1,4-dihydro-2-methyl-4-oxo-1-pentyl-3-pyridinecarboxamide,
837. 5,6-diethyl-N-(2-ethyl-6-methylphenyl)-1-hexyl-1,4-dihydro-2-methyl-4-oxo-3-pyridinecarboxamide,
838. 5,6-diethyl-N-(2-ethyl-6-methylphenyl)-1,4-dihydro-2-methyl-4-oxo-1-phenylmethyl-3-pyridinecarboxamide,
839. 5,6-diethyl-N-(2-ethyl-6-methylphenyl)-1,4-dihydro-2-methyl-4-oxo-1-(2-phenylethyl)-3-pyridinecarboxamide,
840. 1-butyl-6-ethyl-N-(2,6-dimethylphenyl)-1,4-dihydro-2-methyl-4-oxo-3-pyridinecarboxamide,
841. 6-ethyl-1,4-dihydro-2-methyl-N-(2,6-dimethylphenyl)-4-oxo-1-pentyl-3-pyridinecarboxamide,
842. 6-ethyl-1-hexyl-1,4-dihydro-2-methyl-N-(2,6-dimethylphenyl)-4-oxo-3-pyridinecarboxamide,
843. 6-ethyl-1,4-dihydro-2-methyl-N-(2,6-dimethylphenyl)-4-oxo-1-phenylmethyl-3-pyridinecarboxamide,
844. 6-ethyl-1,4-dihydro-2-methyl-N-(2,6-dimethylphenyl)-4-oxo-1-(2-phenylethyl)-3-pyridinecarboxamide,
845. 5-bromo-1-butyl-6-ethyl-1,4-dihydro-2-methyl-N-(2,6-dimethylphenyl)-4-oxo-3-pyridinecarboxamide,
846. 5-bromo-6-ethyl-1,4-dihydro-2-methyl-N-(2,6-dimethylphenyl)-4-oxo-1-pentyl-3-pyridinecarboxamide,
847. 5-bromo-6-ethyl-1-hexyl-1,4-dihydro-2-methyl-N-(2,6-dimethylphenyl)-4-oxo-3-pyridinecarboxamide,
848. 5-bromo-6-ethyl-1,4-dihydro-2-methyl-N-(2,6-dimethylphenyl)-4-oxo-1-phenylmethyl-3-pyridinecarboxamide,
849. 5-bromo-6-ethyl-1,4-dihydro-2-methyl-N-(2,6-dimethylphenyl)-4-oxo-1-(2-phenylethyl)-3-pyridinecarboxamide,
850. 1-butyl-6-ethyl-1,4-dihydro-2,5-dimethyl-N-(2,6-dimethylphenyl)-4-oxo-3-pyridinecarboxamide,
851. 6-ethyl-1,4-dihydro-2,5-dimethyl-N-(2,6-dimethylphenyl)-4-oxo-1-pentyl-3-pyridinecarboxamide,
852. 6-ethyl-1-hexyl-1,4-dihydro-2,5-dimethyl-N-(2,6-dimethylphenyl)-4-oxo-3-pyridinecarboxamide,
853. 6-ethyl-1,4-dihydro-2,5-dimethyl-N-(2,6-dimethylphenyl)-4-oxo-1-phenylmethyl-3-pyridinecarboxamide,
854. 6-ethyl-1,4-dihydro-2,5-dimethyl-N-(2,6-dimethylphenyl)-4-oxo-1-(2-phenylethyl)-3-pyridinecarboxamide,
855. 1-butyl-5,6-diethyl-1,4-dihydro-2-methyl-N-(2,6-dimethylphenyl)-4-oxo-3-pyridinecarboxamide,
856. 5,6-diethyl-1,4-dihydro-2-methyl-N-(2,6-dimethylphenyl)-4-oxo-1-pentyl-3-pyridinecarboxamide,
857. 5,6-diethyl-1-hexyl-1,4-dihydro-2-methyl-N-(2,6-dimethylphenyl)-4-oxo-3-pyridinecarboxamide,
858. 5,6-diethyl-1,4-dihydro-2-methyl-N-(2,6-dimethylphenyl)-4-oxo-1-phenylmethyl-3-pyridinecarboxamide,
859. 5,6-diethyl-1,4-dihydro-2-methyl-N-(2,6-dimethylphenyl)-4-oxo-1-(2-phenylethyl)-3-pyridinecarboxamide,
860. 5-ethyl-N-(2,6-diethylphenyl)-1,4-dihydro-1,6-dimethyl-4-oxo-2-propyl-3-pyridinecarboxamide,
861. N-(4-bromo-2,6-diethylphenyl)-5-ethyl-1,4-dihydro-1,6-dimethyl-4-oxo-2-propyl-3-pyridinecarboxamide,
862. 2-butyl-5-ethyl-N-(2,6-diethylphenyl)-1,4-dihydro-1,6-dimethyl-4-oxo-3-pyridinecarboxamide,
863. 5-bromo-1-ethyl-N-(2,6-diethylpentyl)-1,4-dihydro-6-methyl-4-oxo-2-propyl-3-pyridinecarboxamide,
864. 5-bromo-N-(4-bromo-2,6-diethylphenyl)-1-ethyl-1,4-dihydro-6-methyl-4-oxo-2-propyl-3-pyridinecarboxamide,
865. 5-bromo-2-butyl-N-(2,6-diethylphenyl)-1-ethyl-1,4-dihydro-6-methyl-4-oxo-3-pyridinecarboxamide,
866. 5-bromo-N-(4-bromo-2,6-diethylphenyl)-2-butyl-1-ethyl-1,4-dihydro-6-methyl-4-oxo-3-pyridinecarboxamide,
867. 1-ethyl-N-(2,6-diethylphenyl)-1,4-dihydro-5,6-dimethyl-4-oxo-2-propyl-3-pyridinecarboxamide,
868. N-(4-bromo-2,6-diethylphenyl)-1-ethyl-1,4-dihydro-5,6-dimethyl-4-oxo-2-propyl-3-pyridinecarboxamide,
869. 2-butyl-1-ethyl-N-(2,6-diethylphenyl)-1,4-dihydro-5,6-dimethyl-4-oxo-3-pyridinecarboxamide,
870. N-(4-bromo-2,6-diethylphenyl)-2-butyl-1-ethyl-1,4-dihydro-5,6-dimethyl-4-oxo-3-pyridinecarboxamide,
871. 5-bromo-N-(4-bromo-2,6-diethylphenyl)-6-ethyl-1,4-dihydro-1-methyl-4-oxo-2-propyl-3-pyridinecarboxamide,
872. 5-bromo-2-butyl-6-ethyl-N-(2,6-diethylphenyl)-1,4-dihydro-1-methyl-4-oxo-3-pyridinecarboxamide,
873. 5-bromo-N-(4-bromo-2,6-diethylphenyl)-6-ethyl-1,4-dihydro-1,2-dimethyl-4-oxo-3-pyridinecarboxamide,
874. 6-ethyl-N-(2,6-diethylphenyl)-1,4-dihydro-1,5-dimethyl-4-oxo-2-propyl-3-pyridinecarboxamide, 875. N-(4-bromo-2,6-diethylphenyl)-6-ethyl-1,4-dihydro-1,5-dimethyl-4-oxo-2-propyl-3-pyridinecarboxamide,
876. 2-butyl-6-ethyl-N-(2,6-diethylphenyl)-1,4-dihydro-1,5-dimethyl-4-oxo-3-pyridinecarboxamide,
877. N-(4-bromo-2,6-diethylphenyl)-2-butyl-6-ethyl-1,4-dihydro-1,5-dimethyl-4-oxo-3-pyridinecarboxamide,
878. 5-chloro-N-(2,6-diethylphenyl)-1,4-dihydro-1,6-dimethyl-4-oxo-2-propyl-3-pyridinecarboxamide,
879. N-(4-bromo-2,6-diethylphenyl)-5-chloro-1,4-dihydro-1,6-dimethyl-4-oxo-2-propyl-3-pyridinecarboxamide,
880. 2-butyl-5-chloro-N-(2,6-diethylphenyl)-1,4-dihydro-1,6-dimethyl-4-oxo-3-pyridinecarboxamide,
881. N-(4-bromo-2,6-diethylphenyl)-2-butyl-5-chloro-1,4-dihydro-1,6-dimethyl-4-oxo-3-pyridinecarboxamide,
882. 5-bromo-N-(4-chloro-2,6-diethylphenyl)-1,4-dihydro-1,6-dimethyl-4-oxo-2-propyl-3-pyridinecarboxamide,
883. N-(4-chloro-2,6-diethylphenyl)-1,4-dihydro-1,5,6-trimethyl-4-oxo-2-propyl-3-pyridinecarboxamide,
884. 5-bromo-2-butyl-N-(4-chloro-2,6-diethylphenyl)-1,4-dihydro-1,6-dimethyl-4-oxo-3-pyridinecarboxamide,
885. 2-butyl-N-(4-chloro-2,6-diethylphenyl)-1,4-dihydro-1,5,6-trimethyl-4-oxo-3-pyridinecarboxamide,
886. 5-bromo-N-(2,6-diethyl-4-methylphenyl)-1,4-dihydro-1,6-dimethyl-4-oxo-2-propyl-3-pyridinecarboxamide,
887. N-(2,6-diethyl-4-methylphenyl)-1,4-dihydro-1,5,6-trimethyl-4-oxo-2-propyl-3-pyridinecarboxamide,
888. 5-bromo-2-butyl-N-(2,6-diethyl-4-methylphenyl)-1,4-dihydro-1,6-dimethyl-4-oxo-3-pyridinecarboxamide,
889. 2-butyl-N-(2,6-diethyl-4-methylphenyl)-1,4-dihydro-1,5,6-trimethyl-4-oxo-3-pyridinecarboxamide,
890. N-(4-bromo-2,6-diethylphenyl)-2-ethyl-1,4-dihydro-5,6-dimethyl-4-oxo-1-propyl-3-pyridinecarboxamide,
891. N-(4-bromo-2,6-diethylphenyl)-6-ethyl-1,4-dihydro-2,5-dimethyl-4-oxo-1-propyl-3-pyridinecarboxamide,
892. 2-ethyl-N-(2,6-diethylphenyl)-1,4-dihydro-5,6-dimethyl-4-oxo-1-propyl-3-pyridinecarboxamide,
893. 6-ethyl-N-(2,6-diethylphenyl)-1,4-dihydro-2,5-dimethyl-4-oxo-1-propyl-3-pyridinecarboxamide,
894. N-(4-bromo-2,6-diethylphenyl)-2-ethyl-1,4-dihydro-5,6-dimethyl-4-oxo-1-pentyl-3-pyridinecarboxamide,
895. N-(4-bromo-2,6-diethylphenyl)-6-ethyl-1,4-dihydro-2,5-dimethyl-4-oxo-1-pentyl-3-pyridinecarboxamide,
896. 2-ethyl-N-(2,6-diethylphenyl)-1,4-dihydro-5,6-dimethyl-4-oxo-1-pentyl-3-pyridinecarboxamide,
897. 6-ethyl-N-(2,6-diethylphenyl)-1,4-dihydro-2,5-dimethyl-4-oxo-1-pentyl-3-pyridinecarboxamide,
898. N-(4-bromo-2,6-diethylphenyl)-1-butyl-2-ethyl-1,4-dihydro-5,6-dimethyl-4-oxo-3-pyridinecarboxamide,
899. N-(4-bromo-2,6-diethylphenyl)-1-butyl-6-ethyl-1,4-dihydro-2,5-dimethyl-4-oxo-3-pyridinecarboxamide,
900. 1-butyl-2-ethyl-N-(2,6-diethylphenyl)-1,4-dihydro-5,6-dimethyl-4-oxo-3-pyridinecarboxamide,
901. 1-butyl-6-ethyl-N-(2,6-diethylphenyl)-1,4-dihydro-2,5-dimethyl-4-oxo-3-pyridinecarboxamide,
902. 1-(3-chlorophenyl)-2-ethyl-1,4-dihydro-6-methyl-4-oxo-N-phenyl-3-pyridinecarboxamide,
903. 1-(3-bromophenyl)-2-ethyl-1,4-dihydro-6-methyl-4-oxo-N-phenyl-3-pyridinecarboxamide,
904. 2-ethyl-1-(3-fluorophenyl)-1,4-dihydro-6-methyl-4-oxo-N-phenyl-3-pyridinecarboxamide,
905. 2-ethyl-1,4-dihydro-1-(3-iodophenyl)-6-methyl-4-oxo-N-phenyl-3-pyridinecarboxamide,
906. 2-ethyl-1-(3-trifluoromethylphenyl)-1,4-dihydro-6-methyl-4-oxo-N-phenyl-3-pyridinecarboxamide,
907. 1-(3-chlorophenyl)-1,4-dihydro-6-methyl-4-oxo-N-phenyl-2-propyl-3-pyridinecarboxamide,
908. 1-(3-bromophenyl)-1,4-dihydro-6-methyl-4-oxo-N-phenyl-2-propyl-3-pyridinecarboxamide,
909. 1-(3-fluorophenyl)-1,4-dihydro-6-methyl-4-oxo-N-phenyl-2-propyl-3-pyridinecarboxamide,
910. 1,4-dihydro-1-(3-iodophenyl)-6-methyl-4-oxo-N-phenyl-2-propyl-3-pyridinecarboxamide,
911. 1-(3-trifluoromethylphenyl)-1,4-dihydro-6-methyl-4-oxo-N-phenyl-2-propyl-3-pyridinecarboxamide,
912. 1-(3-chlorophenyl)-1,4-dihydro-6-methyl-4-oxo-2-pentyl-N-phenyl-3-pyridinecarboxamide,
913. 1-(3-bromophenyl)-1,4-dihydro-6-methyl-4-oxo-2-pentyl-N-phenyl-3-pyridinecarboxamide.
914. 1-(3-fluorophenyl)-1,4-dihydro-6-methyl-4-oxo-2-pentyl-N-phenyl-3-pyridinecarboxamide,
915. 1,4-dihydro-1-(3-iodophenyl)-6-methyl-4-oxo-2-pentyl-N-phenyl-3-pyridinecarboxamide,
916. 1-(3-trifluoromethylphenyl)-1,4-dihydro-6-methyl-4-oxo-2-pentyl-N-phenyl-3-pyridinecarboxamide,
917. 2-butyl-1-(2,4-dichlorophenyl)-1,4-dihydro-6-methyl-4-oxo-N-phenyl-3-pyridinecarboxamide,
918. 2-butyl-1-(2,5-dichlorophenyl)-1,4-dihydro-6-methyl-4-oxo-N-phenyl-3-pyridinecarboxamide,
919. 2-butyl-1-(2,6-dichlorophenyl)-1,4-dihydro-6-methyl-4-oxo-N-phenyl-3-pyridinecarboxamide,
920. 1-(3-chlorophenyl)-1,4-dihydro-6-methyl-4-oxo-N,2-diphenyl-3-pyridinecarboxamide,
921. 1-(3-bromophenyl)-1,4-dihydro-6-methyl-4-oxo-N,2-diphenyl-3-pyridinecarboxamide,
922. 1-(3-fluorophenyl)-1,4-dihydro-6-methyl-4-oxo-N,2-diphenyl-3-pyridinecarboxamide,
923. 1,4-dihydro-1-(3-iodophenyl)-6-methyl-4-oxo-N,2-diphenyl-3-pyridinecarboxamide,
924. 1-(3-trifluoromethylphenyl)-1,4-dihydro-6-methyl-4-oxo-N,2-diphenyl-3-pyridinecarboxamide,
925. 1-(3-chlorophenyl)-2-ethyl-1,4-dihydro-6-methyl-N-(2-methylphenyl)-4-oxo-3-pyridinecarboxamide,
926. 1-(3-chlorophenyl)-1,4-dihydro-6-methyl-N-(2-methylphenyl)-4-oxo-2-propyl-3-pyridinecarboxamide,
927. 2-butyl-1-(3-chlorophenyl)-1,4-dihydro-6-methyl-N-(2-methylphenyl)-4-oxo-3-pyridinecarboxamide,
928. 1-(3-chlorophenyl)-1,4-dihydro-6-methyl-N-(2-methylphenyl)-4-oxo-2-pentyl-3-pyridinecarboxamide,
929. 1-(3-chlorophenyl)-1,4-dihydro-6-methyl-N-(2-methylphenyl)-4-oxo-2-phenyl-3-pyridinecarboxamide,
930. N-(2-chlorophenyl)-1-(3-chlorophenyl)-2-ethyl-1,4-dihydro-6-methyl-4-oxo-3-pyridinecarboxamide,
931. N-(2-chlorophenyl)-1-(3-chlorophenyl)-1,4-dihydro-6-methyl-4-oxo-2-propyl-3-pyridinecarboxamide,
932. 2-butyl-N-(2-chlorophenyl)-1-(3-chlorophenyl)-1,4-dihydro-6-methyl-4-oxo-3-pyridinecarboxamide.
933. N-(2-chlorophenyl)-1-(3-chlorophenyl)-1,4-dihydro-6-methyl-4-oxo-2-pentyl-3-pyridinecarboxamide, 934. N-(2-chlorophenyl)-1-(3-chlorophenyl)-1,4-dihydro-6-methyl-4-oxo-2-phenyl-3-pyridinecarboxamide,
935. 5-bromo-N-(2,6-diethylphenyl)-1,4-dihydro-2-methoxymethyl-1,6-dimethyl-4-oxo-3-pyridinecarboxamide,
936. 5-bromo-N-(2,6-diethylphenyl)-1,4-dihydro-1,6-dimethyl-2-methylthiomethyl-4-oxo-3-pyridinecarboxamide,
937. 5-bromo-N-(2,6-diethyl-4-methylphenyl)-1,4-dihydro-2-methoxymethyl-1,6-dimethyl-4-oxo-3-pyridinecarboxamide,
938. 5-bromo-N-(2,6-diethyl-4-methylphenyl)-1,4-dihydro-1,6-dimethyl-2-methylthiomethyl-4-oxo-3-pyridinecarboxamide,
939. 5-bromo-2-butyl-N-(2,4,6-triethylphenyl)-1,4-dihydro-1,6-dimethyl-4-oxo-3-pyridinecarboxamide,
940. 5-bromo-N-(2,4,6-triethylphenyl)-1,4-dihydro-2-methoxymethyl-1,6-dimethyl-4-oxo-3-pyridinecarboxamide,
941. 5-bromo-N-(2,4,6-triethylphenyl)-1,4-dihydro-1,6-dimethyl-2-methylthiomethyl-4-oxo-3-pyridinecarboxamide,
942. 5-bromo-N-(2,6-diethyl-4-propylphenyl)-1,4-dihydro-1,6-dimethyl-4-oxo-2-propyl-3-pyridinecarboxamide,
943. 5-bromo-2-butyl-N-(2,6-diethyl-4-propylphenyl)-1,4-dihydro-1,6-dimethyl-4-oxo-3-pyridinecarboxamide,
944. 5-bromo-N-(2,6-diethyl-4-propylphenyl)-1,4-dihydro-2-methoxymethyl-1,6-dimethyl-4-oxo-3-pyridinecarboxamide,
945. 5-bromo-N-(2,6-diethyl-4-propylphenyl)-1,4-dihydro-1,6-dimethyl-2-methylthiomethyl-4-oxo-3-pyridinecarboxamide,
946. 5-bromo-N-{2,6-diethyl-4-(1-methylethyl)phenyl}-1,4-dihydro-1,6-dimethyl-4-oxo-2-propyl-3-pyridinecarboxamide,
947. 5-bromo-2-butyl-N-{2,6-diethyl-4-(1-methylethyl)phenyl}-1,4-dihydro-1,6-dimethyl-4-oxo-3-pyridinecarboxamide,
948. 5-bromo-N-{2,6-diethyl-4-(1-methylethyl)phenyl}-1,4-dihydro-2-methoxymethyl-1,4-dimethyl-4-oxo-3-pyridinecarboxamide,
949. 5-bromo-N-{2,6-diethyl-4-(1-methylethyl)phenyl}-1,4-dihydro-1,6-dimethyl-2-methylthiomethyl-4-oxo-3-pyridinecarboxamide,
950. 5-bromo-N-{2,6-diethyl-4-(1,1-dimethylethyl)phenyl}-1,4-dihydro-1,6-dimethyl-4-oxo-2-propyl-3-pyridinecarboxamide,
951. 5-bromo-2-butyl-N-{2,6-diethyl-4-(1,1-dimethylethyl)phenyl}1,4-dihydro-1,6-dimethyl-4-oxo-3-pyridinecarboxamide,
952. 5-bromo-N-{2,6-diethyl-4-(1,1-dimethylethyl)phenyl}-1,4-dihydro-2-methoxymethyl-1,6-dimethyl-4-oxo-3-pyridinecarboxamide,
953. 5-bromo-N-{2,6-diethyl-4-(1,1-dimethylethyl)phenyl}-1,4-dihydro-1,6-dimethyl-2-methylthiomethyl-4-oxo-3-pyridinecarboxamide,
954. 5-bromo-N-(2,6-diethyl-4-trifluoromethylphenyl)-1,4-dihydro-1,6-dimethyl-4-oxo-2-propyl-3-pyridinecarboxamide,
955. 5-bromo-2-butyl-N-(2,6-diethyl-4-trifluoromethylphenyl)-1,4-dihydro-1,6-dimethyl-4-oxo-3-pyridinecarboxamide,
956. 5-bromo-N-(2,6-diethyl-4-trifluoromethylphenyl)-1,4-dihydro-2-methoxymethyl-1,6-dimethyl-4-oxo-3-pyridinecarboxamide,
957. 5-bromo-N-(2,6-diethyl-4-trifluoromethylphenyl)-1,4-dihydro-1,6-dimethyl-2-methylthiomethyl-4-oxo-3-pyridinecarboxamide,
958. 5-bromo-N-(4-bromo-2,6-diethylphenyl)-1,4-dihydro-1,6-dimethyl-4-oxo-2-propyl-3-pyridinecarboxamide,
959. 5-bromo-N-(bromo-2,6-diethylphenyl)-2-butyl-1,4-dihydro-1,6-dimethyl-4-oxo-3-pyridinecarboxamide,
960. 5-bromo-2-butyl-N-(2,6-diethyl-4-iodophenyl)-1,4-dihydro-1,6-dimethyl-4-oxo-3-pyridinecarboxamide,
961. 5-bromo-N-(2,6-diethyl-4-iodophenyl)-1,4-dihydro-2-methoxymethyl-1,6-dimethyl-4-oxo-3-pyridinecarboxamide,
962. 5-bromo-N-(2,6-diethyl-4-iodophenyl)-1,4-dihydro-1,6-dimethyl-2-methylthiomethyl-4-oxo-3-pyridinecarboxamide,
963. 5-bromo-2-butyl-N-(2,6-diethyl-4-hydroxyphenyl)-1,4-dihydro-1,6-dimethyl-4-oxo-3-pyridinecarboxamide,
964. 5-bromo-N-(2,6-diethyl-4-hydroxyphenyl)-1,4-dihydro-2-methoxymethyl-1,6-dimethyl-4-oxo-3-pyridinecarboxamide,
965. 5-bromo-N-(2,6-diethyl-4-hydroxyphenyl)-1,4-dihydro-1,6-dimethyl-2-methylthiomethyl-4-oxo-3-pyridinecarboxamide,
966. 5-bromo-2-butyl-N-(2,6-diethyl-4-methoxyphenyl)-1,4-dihydro-1,6-dimethyl-4-oxo-3-pyridinecarboxamide,
967. 5-bromo-N-(2,6-diethyl-4-methoxyphenyl)-1,4-dihydro-2-methoxymethyl-1,6-dimethyl-4-oxo-3-pyridinecarboxamide,
968. 5-bromo-N-(2,6-diethyl-4-methoxyphenyl)-1,4-dihydro-1,6-dimethyl-2-methylthiomethyl-4-oxo-3-pyridinecarboxamide,
969. 5-bromo-N-(2,6-diethyl-4-phenoxyphenyl)-1,4-dihydro-1,6-dimethyl-4-oxo-2-propyl-3-pyridinecarboxamide,
970. 5-bromo-2-butyl-N-(2,6-diethyl-4-phenoxyphenyl)-1,4-dihydro-1,6-dimethyl-4-oxo-3-pyridinecarboxamide,
971. 5-bromo-N-(2,6-diethyl-4-phenoxyphenyl)-1,4-dihydro-2-methoxymethyl-1,6-dimethyl-4-oxo-3-pyridinecarboxamide,
972. 5-bromo-N-(2,6-diethyl-4-phenoxyphenyl)-1,4-dihydro-1,6-dimethyl-2-methylthiomethyl-4-oxo-3-pyridinecarboxamide,
973. N-(4-amino-2,6-diethylphenyl)-5-bromo-1,4-dihydro-1,6-dimethyl-4-oxo-2-propyl-3-pyridinecarboxamide,
974. N-(4-amino-2,6-diethylphenyl)-5-bromo-2-butyl-1,4-dihydro-1,6-dimethyl-4-oxo-3-pyridinecarboxamide,
975. N-(4-amino-2,6-diethylphenyl)-5-bromo-1,4-dihydro-2-methoxymethyl-1,6-dimethyl-4-oxo-3-pyridinecarboxamide,
976. N-(4-amino-2,6-diethylphenyl)-5-bromo-1,4-dihydro-1,6-dimethyl-2-methylthiomethyl-4-oxo-3-pyridinecarboxamide,
977. 5-bromo-N-(2,6-diethyl-4-nitrophenyl)-1,4-dihydro-1,6-dimethyl-4-oxo-2-propyl-3-pyridinecarboxamide,
978. 5-bromo-2-butyl-N-(2,6-diethyl-4-nitrophenyl)-1,4-dihydro-1,6-dimethyl-4-oxo-3-pyridinecarboxamide,
979. 5-bromo-N-(2,6-diethyl-4-nitrophenyl)-1,4-dihydro-2-methoxymethyl-1,6-dimethyl-4-oxo-3-pyridinecarboxamide, 980. 5-bromo-N-(2,6-diethyl-4-nitrophenyl)-1,4-dihydro-1,6-dimethyl-2-methylthiomethyl-4-oxo-3-pyridinecarboxamide,
981. 5-bromo-N-(4-cyano-2,6-diethylphenyl)-1,4-dihydro-1,6-dimethyl-4-oxo-2-propyl-3-pyridinecarboxamide,
982. 5-bromo-2-butyl-N-(4-cyano-2,6-diethylphenyl)-1,4-dihydro-1,6-dimethyl-4-oxo-3-pyridinecarboxamide,
983. 5-bromo-N-(4-cyano-2,6-diethylphenyl)-1,4-dihydro-2-methoxymethyl-1,6-dimethyl-4-oxo-3-pyridinecarboxamide,
984. 5-bromo-N-(4-cyano-2,6-diethylphenyl)-1,4-dihydro-1,6-dimethyl-2-methylthiomethyl-4-oxo-3-pyridinecarboxamide,
985. 5-bromo-N-(2,6-diethyl-4-methoxycarbonylphenyl)-1,4-dihydro-1,6-dimethyl-4-oxo-2-propyl-3-pyridinecarboxamide,
986. 5-bromo-2-butyl-N-(2,6-diethyl-4-methoxycarbonylphenyl)-1,4-dihydro-1,6-dimethyl-4-oxo-3-pyridinecarboxamide,
987. 5-bromo-N-(2,6-diethyl-4-methoxycarbonylphenyl)-1,4-dihydro-2-methoxymethyl-1,6-dimethyl-4-oxo-3-pyridinecarboxamide,
988. 5-bromo-N-(2,6-diethyl-4-methoxycarbonylphenyl)-1,4-dihydro-1,6-dimethyl-2-methylthiomethyl-4-oxo-3-pyridinecarboxamide,
989. 5-bromo-N-(2,6-diethyl-4-ethoxycarbonylphenyl)-1,4-dihydro-1,6-dimethyl-4-oxo-2-propyl-3-pyridinecarboxamide,
990. 5-bromo-2-butyl-N-(2,6-diethyl-4-ethoxycarbonylphenyl)-1,4-dihydro-1,6-dimethyl-4-oxo-3-pyridinecarboxamide,
991. 5-bromo-N-(2,6-diethyl-4-ethoxycarbonylphenyl)-1,4-dihydro-2-methoxymethyl-1,6-diethyl-4-oxo-3-pyridinecarboxamide,
992. 5-bromo-N-(2,6-diethyl-4-ethoxycarbonylphenyl)-1,4-dihydro-1,6-dimethyl-2-methylthiomethyl-4-oxo-3-pyridinecarboxamide,
993. 5-bromo-N-(2,6-diethyl-4-hydroxyphenyl)-1,4-dihydro-1,6-dimethyl-4-oxo-2-propyl-3-pyridinecarboxamide,
994. 2-butyl-N-(2,4,6-triethylphenyl)-1,4-dihydro-1,5,6-trimethyl-4-oxo-3-pyridinecarboxamide,
995. N-(2,6-diethyl-4-propylphenyl)-1,4-dihydro-1,5,6-trimethyl-4-oxo-2-propyl-3-pyridinecarboxamide,
996. 2-butyl-N-(2,6-diethyl-4-propylphenyl)-1,4-dihydro-1,5,6-trimethyl-4-oxo-3-pyridinecarboxamide,
997. N-{2,6-diethyl-4-(1-methylethyl)phenyl}-1,4-dihydro-1,5,6-trimethyl-4-oxo-2-propyl-3-pyridinecarboxamide,
998. 2-butyl-N-{2,6-diethyl-4-(1-methylethyl)phenyl}-1,4-dihydro-1,5,6-trimethyl-4-oxo-3-pyridinecarboxamide,
999. N-{2,6-diethyl-4-(1,1-dimethylethyl)phenyl}-1,4-dihydro-1,5,6-trimethyl-4-oxo-2-propyl-3-pyridinecarboxamide,
1000. 2-butyl-N-{2,6-diethyl-4-(1,1-dimethylethyl)phenyl}-1,4-dihydro-1,5,6-trimethyl-4-oxo-3-pyridinecarboxamide,
1001. N-(2,6-diethyl-4-trifluoromethylphenyl)-1,4-dihydro-1,5,6-trimethyl-4-oxo-2-propyl-3-pyridinecarboxamide,
1002. 2-butyl-N-(2,6-diethyl-4-trifluoromethylphenyl)-1,4-dihydro-1,5,6-trimethyl-4-oxo-3-pyridinecarboxamide,
1003. 2-butyl-N-(2,6-diethyl-4-iodophenyl)-1,4-dihydro-1,5,6-trimethyl-4-oxo-3-pyridinecarboxamide,
1004. N-(2,6-diethyl-4-hydroxyphenyl)-1,4-dihydro-1,5,6-trimethyl-4-oxo-2-propyl-3-pyridinecarboxamide,
1005. 2-butyl-N-(2,6-diethyl-4-hydroxyphenyl)-1,4-dihydro-1,5,6-trimethyl-4-oxo-3-pyridinecarboxamide,
1006. N-(2,6-diethyl-4-methoxyphenyl)-1,4-dihydro-1,5,6-trimethyl-4-oxo-2-propyl-3-pyridinecarboxamide,
1007. 2-butyl-N-(2,6-diethyl-4-methoxyphenyl)-1,4-dihydro-1,5,6-trimethyl-4-oxo-3-pyridinecarboxamide,
1008. N-(2,6-diethyl-4-phenoxyphenyl)-1,4-dihydro-1,5,6-trimethyl-4-oxo-2-propyl-3-pyridinecarboxamide,
1009. 2-butyl-N-(2,6-diethyl-4-phenoxyphenyl)-1,4-dihydro-1,5,6-trimethyl-4-oxo-3-pyridinecarboxamide,
1010. N-(4-amino-2,6-diethylphenyl)-1,4-dihydro-1,5,6-trimethyl-4-oxo-2-propyl-3-pyridinecarboxamide,
1011. N-(4-amino-2,6-diethylphenyl)-2-butyl-1,4-dihydro-1,5,6-trimethyl-4-oxo-3-pyridinecarboxamide,
1012. N-(2,6-diethyl-4-nitrophenyl)-1,4-dihydro-1,5,6-trimethyl-4-oxo-2-propyl-3-pyridinecarboxamide,
1013. 2-butyl-N-(2,6-diethyl-4-nitrophenyl)-1,4-dihydro-1,5,6-trimethyl-4-oxo-3-pyridinecarboxamide,
1014. N-(4-cyano-2,6-diethylphenyl)-1,4-dihydro-1,5,6-trimethyl-4-oxo-2-propyl-3-pyridinecarboxamide,
1015. 2-butyl-N-(4-cyano-2,6-diethylphenyl)-1,4-dihydro-1,5,6-trimethyl-4-oxo-3-pyridinecarboxamide,
1016. N-(2,6-diethyl-4-methoxycarbonylphenyl)-1,4-dihydro-1,5,6-trimethyl-4-oxo-2-propyl-3-pyridinecarboxamide,
1017. 2-butyl-N-(2,6-diethyl-4-methoxycarbonylphenyl)-1,4-dihydro-1,5,6-trimethyl-4-oxo-3-pyridinecarboxamide,
1018. N-(2,6-diethyl-4-ethoxycarbonylphenyl)-1,4-dihydro-1,5,6-trimethyl-4-oxo-2-propyl-3-pyridinecarboxamide,
1019. 2-butyl-N-(2,6-diethyl-4-ethoxycarbonylphenyl)-1,4-dihydro-1,5,6-trimethyl-4-oxo-3-pyridinecarboxamide,
1020. 5-ethyl-N-(2,6-diethyl-4-methylphenyl)-1,4-dihydro-1,6-dimethyl-4-oxo-2-propyl-3-pyridinecarboxamide,
1021. 2-butyl-5-ethyl-N-(2,6-diethyl-6-methylphenyl)-1,4-dihydro-1,6-dimethyl-4-oxo-3-pyridinecarboxamide,
1022. 5-ethyl-N-(2,4,6-triethylphenyl)-1,4-dihydro-1,6-dimethyl-4-oxo-2-propyl-3-pyridinecarboxamide,
1023. 2-butyl-5-ethyl-N-(2,4,6-triethylphenyl)-1,4-dihydro-1,6-dimethyl-4-oxo-3-pyridinecarboxamide,
1024. 5-ethyl-N-(2,6-diethyl-4-propylphenyl)-1,4-dihydro-1,6-dimethyl-4-oxo-2-propyl-3-pyridinecarboxamide,
1025. 2-butyl-5-ethyl-N-(2,6-diethyl-4-propylphenyl)-1,4-dihydro-1,6-dimethyl-4-oxo-3-pyridinecarboxamide,
1026. 5-ethyl-N-{2,6-diethyl-4-(1-methylethyl)phenyl}-1,4-dihydro-1,6-dimethyl-4-oxo-2-propyl-3-pyridinecarboxamide,
1027. 2-butyl-5-ethyl-N-{2,6-diethyl-4-(1-methylethyl)phenyl}-1,4-dihydro-1,6-dimethyl-4-oxo-3-pyridinecarboxamide,
1028. 5-ethyl-N-{2,6-diethyl-4-(1,1-dimethylethyl)phenyl}-1,4-dihydro-1,6-dimethyl-4-oxo-2-propyl-3-pyridinecarboxamide, 1029. 2-butyl-5-ethyl-N-{2,6-diethyl-4-(1,1-dimethylethyl)phenyl}-1,4-dihydro-1,6-dimethyl-4-oxo-3-pyridinecarboxamide,
1030. 5-ethyl-N-(2,6-diethyl-4-trifluoromethylphenyl)-1,4-dihydro-1,6-dimethyl-4-oxo-2-propyl-3-pyridinecarboxamide,
1031. 2-butyl-5-ethyl-N-(2,6-diethyl-4-trifluoromethylphenyl)-1,4-dihydro-1,6-dimethyl-4-oxo-3-pyridinecarboxamide,
1032. 5-ethyl-N-(2,6-diethyl-4-iodophenyl)-1,4-dihydro-1,6-dimethyl-4-oxo-2-propyl-3-pyridinecarboxamide,
1033. 2-butyl-5-ethyl-N-(2,6-diethyl-4-iodophenyl)-1,4-dihydro-1,6-dimethyl-4-oxo-3-pyridinecarboxamide,
1034. 5-ethyl-N-(2,6-diethyl-4-hydroxyphenyl)-1,4-dihydro-1,6-dimethyl-4-oxo-2-propyl-3-pyridinecarboxamide,
1035. 2-butyl-5-ethyl-N-(2,6-diethyl-4-hydroxyphenyl)-1,4-dihydro-1,6-dimethyl-4-oxo-3-pyridinecarboxamide,
1036. 5-ethyl-N-(2,6-diethyl-4-methoxyphenyl)-1,4-dihydro-1,6-dimethyl-4-oxo-2-propyl-3-pyridinecarboxamide,
1037. 2-butyl-5-ethyl-N-(2,6-diethyl-4-methoxyphenyl)-1,4-dihydro-1,6-dimethyl-4-oxo-3-pyridinecarboxamide,
1038. 5-ethyl-N-(2,6-diethyl-4-phenoxyphenyl)-1,4-dihydro-1,6-dimethyl-4-oxo-2-propyl-3-pyridinecarboxamide,
1039. 2-butyl-5-ethyl-N-(2,6-diethyl-4-phenoxyphenyl)-1,4-dihydro-1,6-dimethyl-4-oxo-3-pyridinecarboxamide,
1040. N-(4-amino-2,6-diethylphenyl)-5-ethyl-1,4-dihydro-1,6-dimethyl-4-oxo-2-propyl-3-pyridinecarboxamide,
1041. N-(4-amino-2,6-diethylphenyl)-2-butyl-5-ethyl-1,4-dihydro-1,6-dimethyl-4-oxo-3-pyridinecarboxamide,
1042. 5-ethyl-N-(2,6-diethyl-4-nitrophenyl)-1,4-dihydro-1,6-dimethyl-4-oxo-2-propyl-3-pyridinecarboxamide,
1043. 2-butyl-5-ethyl-N-(2,6-diethyl-4-nitrophenyl)-1,4-dihydro-1,6-dimethyl-4-oxo-3-pyridinecarboxamide,
1044. N-(4-cyano-2,6-diethylphenyl)-5-ethyl-1,4-dihydro-1,6-dimethyl-4-oxo-2-propyl-3-pyridinecarboxamide,
1045. 2-butyl-N-(4-cyano-2,6-diethylphenyl)-5-ethyl-1,4-dihydro-1,6-dimethyl-4-oxo-3-pyridinecarboxamide,
1046. 5-ethyl-N-(2,6-diethyl-4-methoxycarbonylphenyl)-1,4-dihydro-1,6-dimethyl-4-oxo-2-propyl-3-pyridinecarboxamide,
1047. 2-butyl-5-ethyl-N-(2,6-diethyl-4-methoxycarbonylphenyl)-1,4-dihydro-1,6-dimethyl-4-oxo-3-pyridinecarboxamide,
1048. 5-ethyl-N-(2,6-diethyl-4-ethoxycarbonylphenyl)-1,4-dihydro-1,6-dimethyl-4-oxo-2-propyl-3-pyridinecarboxamide,
1049. 2-butyl-5-ethyl-N-(2,6-diethyl-4-ethoxycarbonylphenyl)-1,4-dihydro-1,6-dimethyl-4-oxo-3-pyridinecarboxamide.

EXAMPLE 1

1-butyl-1,4-dihydro-6-methyl-4-oxo-N,2-diphenyl-3-pyridinecarboxamide

A mixture of 4.42 g (18.47 mmol) of α-benzoylacetanilide, 1.89 g (25.84 mmol) of n-butylamine, one drop of acetic acid and 25 ml of toluene was refluxed for 1.5 hours, while the resulted water and excess of butylamine were removed through a Dean-Stark's water separator, together with about 12 ml of toluene. While heating, to the mixture was dropwise added a solution of 7.2 g (46.18 mmol) of 2-ethyl-2,6-dimethyl-4H-1,3-dioxin-4-one in 16 ml of toluene within about 30 minutes and after the resulted mixture was refluxed for forty minutes, it was cooled to room temperature. The crystals precipitated was separated by filtration and dried under vacuo to afford 3.72 g of the title compound having mp. 189.5°–193° C.

EXAMPLE 2

1,4-dihydro-6-methyl-4-oxo-N,2-diphenyl-1-pentyl-3-pyridinecarboxamide 1 g (3.23 mmol) of 6-methyl-4-oxo-N,2-diphenyl-4H-pyran-3-carboxamide and 590 mg (6.78 mmol) of benzylamine were dissolved in 10 ml of ethanol, and the resulted mixture was stirred over night at room temperature. Ethanol was removed under vacuo. The crystal residue was recrystallized from ethylacetate to afford 700 mg of the title compound having mp. 164°–165.5° C.

EXAMPLE 3

5-bromo-1-butyl-6-ethyl-N-(2,6-diethylphenyl)-1,4-dinydro-2-methyl-4-oxo-3-pyridinecarboxamide To a mixture of 700 mg (1.90 mmol) of 1-butyl-6-ethyl-N-(2,6-diethylphenyl)-1,4-dihydro-2-methyl-4-oxo-3-pyridinecarboxamide, 14 ml of methylene chloride and 1.2 g (7.40 mmol) of sodium carbonate was added a solution of 303 mg (1.90 mmol) of bromine in 5 ml of methylene chloride under vigorous stirring. After the completion of addition the mixture was stirred for 6 hours. The insoluble product in methylene chloride was filtered off and the filtrate was concentrated in vacuo to give a crystalline residue. The residue was recrystallized from benzene and cyclohexane to afford 615 mg of the title compound having mp. 132.5°–133.5° C.

EXAMPLE 4

1,4-dihydro-2-methyl-4-oxo-N,5-diphenyl-1-phenylmethyl-3-pyridinecarboxamide

To a mixture of 2.66 g (10 mmol) of 3-benzylaminocrotonanilide, 0.87 g (11 mmol) of pyridine and 30 ml of methylene chloride was added a mixture of 1.45 ml (11 mmol) of phenylacetylchloride and 5 ml of methylene chloride under ice cooling. After the mixture was stirred for 2.5 hours under ice cooling, it was poured into ice water and extracted. The organic layer was dried and concentrated in an usual manner and the residue was crystallized form benzene and diethylether to afford 1.81 g of 2-phenylacetyl-3-phenylmethylamino-2-butenoylanilide. A mixture of 1.60 g (4.16 mmol) of 2-phenylacetyl-3-phenylmethylamino-2-butenoylanilide, 2.23 g of N,N-dimethylformamide dimethylacetal, 0.2 ml of triethylamine and 5 ml of benzene was refluxed for 80 minutes under nitrogen atmosphere. The reaction mixture was concentrated under vacuo to give an oily residue, which was purified by column chromatography and crystallization from ethylacetate to afford 0.70 g of the title compound.

The following Table 1 and Table 2 show physical properties of the compounds associated with this invention. Numbers in the column "Evaluation" in Table 2 were obtained as follows.

A carrier was prepared by mixing 50 parts (by weight) of talc, 25 parts of bentonite, 2 parts of Solpole- 9047 (Toho Chemical Co., Ltd, Japan) and 3 parts of Solpole-5039 (Toho Chemical Co., Ltd, Japan). 50 parts of a test compound and 200 parts of the carrier were mixed to obtain 20% wettable powder, followed by dispersing the powder in distilled water to make a dispersion of the definite concentrations.

Seeds of *Oryza sativa* L., *Echinochloa crus-galli* L., and *Raphanus sativus* L. were germinated in a laboratory dish, to which the dispersion was added. After breeding for 7 days in a thermostatic box kept at 25° C. under illumination of fluorescent tubes, growth of plant was observed. In the column of "Evaluation" of Table 2, the designation 1 denotes no influence, 2 denotes 25% growth inhibition, 3 denotes 50% growth inhibition, 4 denotes 75% growth inhibition and 5 denotes 100% growth inhibition.

TABLE 1

| Example NO. | R | $R_2$ | $R_3$ | $R_4$ | $R_5$ | $R_6$ | $R_7$ | Melting point (°C.) | Molecular formula | Method |
|---|---|---|---|---|---|---|---|---|---|---|
| 1 | phenylmethyl | $C_2H_5$ | H | H | H | H | $CH_3$ | 155–157 | $C_{22}H_{22}N_2O_2$ | A |
| 2 | 4-methyl phenylmethyl | " | " | " | " | " | " | 153–154 | $C_{23}H_{24}N_2O_2$ | A |
| 3 | butyl | n-$C_3H_7$ | " | " | " | " | " | 116–117 | $C_{20}H_{26}N_2O_2$ | A |
| 4 | phenylmethyl | " | " | " | " | " | " | 150–152 | $C_{23}H_{24}N_2O_2$ | A |
| 5 | 2-phenylethyl | " | " | " | " | " | " | 132–133 | $C_{24}H_{26}N_2O_2$ | A |
| 6 | phenylmethyl | n-$C_4H_9$ | " | " | " | " | " | 132–134 | $C_{24}H_{26}N_2O_2$ | A |
| 7 | 4-methyl phenylmethyl | " | " | " | " | " | " | | $C_{25}H_{28}N_2O_2$ | A |
| 8 | phenylmethyl | iso-$C_4H_9$ | " | " | " | " | " | 112.5–114 | $C_{24}H_{26}N_2O_2$ | A |
| 9 | " | n-$C_5H_{11}$ | " | " | " | " | " | 114–115.5 | $C_{25}H_{28}N_2O_2$ | A |
| 10 | " | n-$C_7H_{15}$ | " | " | " | " | " | 86–88 | $C_{27}H_{32}N_2O_2$ | A |
| 11 | " | n-$C_9H_{19}$ | " | " | " | " | " | | $C_{29}H_{36}N_2O_2$ | A |
| 12 | " | phenylmethyl | " | " | " | " | " | 190.5–193 | $C_{27}H_{24}N_2O_2$ | A |
| 13 | 4-methyl phenylmethyl | phenylmethyl | H | H | H | H | $CH_3$ | 188–189 | $C_{28}H_{26}N_2O_2$ | A |
| 14 | H | phenyl | " | " | " | " | " | 277–279 | $C_{19}H_{16}N_2O_2$ | B |
| 15 | methyl | " | " | " | " | " | " | 215–217 | $C_{20}H_{18}N_2O_2$ | B |
| 16 | ethyl | " | " | " | " | " | " | 207–209 | $C_{21}H_{20}N_2O_2$ | B |
| 17 | propyl | " | " | " | " | " | " | 180–183 | $C_{22}H_{22}N_2O_2$ | B |
| 18 | butyl | " | " | " | " | " | " | 189.5–193 | $C_{23}H_{24}N_2O_2$ | A |
| 19 | pentyl | " | " | " | " | " | " | 170.5–173 | $C_{24}H_{26}N_2O_2$ | B |
| 20 | hexyl | " | " | " | " | " | " | 137–138.5 | $C_{25}H_{28}N_2O_2$ | A |
| 21 | octyl | " | " | " | " | " | " | | $C_{27}H_{32}N_2O_2$ | A |
| 22 | 3-methoxypropyl | " | " | " | " | " | " | 203–204.5 | $C_{23}H_{24}N_2O_3$ | A |
| 23 | 2- | " | " | " | " | " | " | 191–192 | $C_{22}H_{22}N_2O_3$ | A |
| 24 | phenyl | " | " | " | " | " | " | more than 300° C. | $C_{25}H_{20}N_2O_2$ | A |
| 25 | phenylmethyl | phenyl | H | H | H | H | $CH_3$ | 185.5–187.5 | $C_{26}H_{22}N_2O_2$ | A |
| 26 | 4-methyl phenylmethyl | " | " | " | " | " | " | 191.5–193 | $C_{27}H_{24}N_2O_2$ | A |
| 27 | 4-chloro phenylmthyl | " | " | " | " | " | " | 198–200 | $C_{26}H_{21}ClN_2O_2$ | A |
| 28 | 2-phenylethyl | " | " | " | " | " | " | 168–171 | $C_{27}H_{24}N_2O_2$ | A |
| 29 | 2-furylmethyl | " | " | " | " | " | " | | $C_{24}H_{20}N_2O_3$ | A |
| 30 | 2-pyridylmethyl | " | " | " | " | " | " | 209–211 | $C_{25}H_{21}N_3O_2$ | A |
| 31 | phenylmethyl | 3-chloro phenyl | " | " | " | " | " | 227–229 | $C_{26}H_{21}ClN_2O_2$ | A |
| 32 | " | 4-chloro phenyl | " | " | " | " | " | 222.5–228 | $C_{26}H_{21}ClN_2O_2$ | A |
| 33 | " | 4-methyl phenyl | " | " | " | " | " | 172–175 | $C_{27}H_{24}N_2O_2$ | A |
| 34 | " | 2-furyl | " | " | " | " | " | | $C_{24}H_{20}N_2O_3$ | A |
| 35 | " | n-$C_3H_7$ | 2-$CH_3$ | " | " | " | " | 139–140.5 | $C_{24}H_{26}N_2O_2$ | A |
| 36 | 4-chrolo phenylmethyl | " | " | " | " | " | " | 124–125 | $C_{24}H_{25}ClN_2O_2$ | A |
| 37 | 2-phenylethyl | n-$C_3H_7$ | 2-$CH_3$ | H | H | H | $CH_3$ | 132.5–134.5 | $C_{25}H_{28}N_2O_2$ | A |
| 38 | butyl | phenyl | " | " | " | " | " | 166.5–168.0 | $C_{24}H_{26}N_2O_2$ | A |
| 39 | phenylmethyl | " | " | " | " | " | " | 231–233 | $C_{27}H_{24}N_2O_2$ | A |
| 40 | 4-chloro phenylmethyl | " | " | " | " | " | " | 106–109 | $C_{27}H_{23}ClN_2O_2$ | A |
| 41 | butyl | " | 2-Cl | " | " | " | " | 174–175 | $C_{23}H_{23}ClN_2O_2$ | A |
| 42 | " | " | 2-$CH_3$ | 3-$CH_3$ | " | " | " | 221–224 | $C_{25}H_{28}N_2O_2$ | A |
| 43 | phenylmethyl | " | " | " | " | " | " | 214–216 | $C_{28}H_{26}N_2O_2$ | A |
| 44 | 2-phenylethyl | " | " | " | " | " | " | 215–217.5 | $C_{29}H_{28}N_2O_2$ | A |
| 45 | butyl | " | 2-$CH_3$ | 6-$CH_3$ | " | " | " | 166– | $C_{25}H_{28}N_2O_2$ | A |

TABLE 1-continued

| Example NO. | R | R₂ | R₃ | R₄ | R₅ | R₆ | R₇ | Melting point (°C.) | Molecular formula | Method |
|---|---|---|---|---|---|---|---|---|---|---|
| 46 | phenylmethyl | " | " | " | " | " | " | 168.5 | C₂₈H₂₆N₂O₂ | A |
| 47 | butyl | H | 2-C₂H₅ | 6-C₂H₅ | " | " | " | 151–152.5 | C₂₁H₂₈N₂O₂ | C' |
| 48 | " | C₂H₅ | " | " | " | " | " | | C₂₃H₃₂N₂O₂ | A |
| 49 | phenylmethyl | C₂H₅ | 2-C₂H₅ | 6-C₂H₅ | H | H | CH₃ | | C₂₆H₃₀N₂O₂ | A |
| 50 | 2-phenylethyl | " | " | " | " | " | " | | C₂₇H₃₂N₂O₂ | A |
| 51 | propyl | n-C₃H₇ | " | " | " | " | " | | C₂₃H₃₂N₂O₂ | A |
| 52 | butyl | " | " | " | " | " | " | | C₂₄H₃₄N₂O₂ | A |
| 53 | phenylmethyl | " | " | " | " | " | " | 152–154 | C₂₇H₃₂N₂O₂ | A |
| 54 | butyl | n-C₄H₉ | " | " | " | " | " | | C₂₅H₃₆N₂O₂ | A |
| 55 | " | iso-C₄H₉ | " | " | " | " | " | | C₂₅H₃₆N₂O₂ | A |
| 56 | " | phenylmethyl | " | " | " | " | " | | C₂₈H₃₄N₂O₂ | A |
| 57 | " | phenyl | " | " | " | " | " | 152–153 | C₂₇H₃₂N₂O₂ | A |
| 58 | phenyl | " | " | " | " | " | " | more than 300° C. | C₂₉H₂₈N₂O₂ | A |
| 59 | phenylmethyl | " | " | " | " | " | " | 100–103 | C₃₀H₃₀N₂O₂ | A |
| 60 | 2-phenylmethyl | phenyl | " | " | " | " | " | 196–197.5 | C₃₁H₃₂N₂O₂ | A |
| 61 | 2-methylphenyl | phenyl | 2-C₂H₅ | 6-C₂H₅ | H | H | CH₃ | 162.5–163.5 | C₃₀H₃₀N₂O₂ | A |
| 62 | phenyl | 4-methylphenyl | " | " | " | " | " | 297–299 | C₃₀H₃₀N₂O₂ | A |
| 63 | butyl | C₂H₅ | " | " | " | Br | " | | C₂₃H₃₁BrN₂O₂ | D |
| 64 | phenylmethyl | CH₃ | H | H | " | H | C₂H₅ | 135–137 | C₂₂H₂₂N₂O₂ | B |
| 65 | " | " | " | " | " | " | n-C₃H₇ | 112–113 | C₂₃H₂₄N₂O₂ | B |
| 66 | butyl | " | " | " | " | " | phenyl | 181–183 | C₂₃H₂₄N₂O₂ | B |
| 67 | phenylmethyl | " | " | " | " | " | " | 104–106 | C₂₆H₂₂N₂O₂ | B |
| 68 | " | " | " | " | " | " | CF₃ | 78–80 | C₂₁H₁₇F₃N₂O₂ | B |
| 69 | butyl | " | 2-C₂H₅ | 6-C₂H₅ | " | " | C₂H₅ | 112.5–114.5 | C₂₃H₃₂N₂O₂ | B |
| 70 | phenylmethyl | " | " | " | " | " | " | 133.5–135 | C₂₆H₃₀N₂O₂ | B |
| 71 | 2-phenylethyl | " | " | " | " | " | " | 109–111 | C₂₇H₃₂N₂O₂ | B |
| 72 | butyl | " | " | " | " | Br | " | 132.5–133.5 | C₂₃H₃₁BrN₂O₂ | D |
| 73 | 2-phenylethyl | CH₃ | 2-C₂H₅ | 6-C₂H₅ | H | Br | C₂H₅ | 126–129.5 | C₂₇H₃₁BrN₂O₂ | D |
| 74 | butyl | " | " | " | " | H | n-C₃H₇ | | C₂₄H₃₄N₂O₂ | B |
| 75 | 2-phenylethyl | " | " | " | " | " | " | | C₂₈H₃₄N₂O₂ | B |
| 76 | " | " | " | " | " | " | CF₃ | 179–180 | C₂₆H₂₇F₃N₂O₂ | B |
| 77 | butyl | " | " | " | " | " | n-C₄H₉ | | C₂₅H₃₆N₂O₂ | B |
| 78 | 2-phenylethyl | " | " | " | " | " | " | | C₂₉H₃₆N₂O₂ | B |
| 79 | butyl | " | " | " | phenyl | " | H | 180–182 | C₂₇H₃₂N₂O₂ | F |
| 80 | 2-phenylethyl | " | " | " | H | —(CH₂)₄— | | 188–190 | C₂₉H₃₄N₂O₂ | B |
| 81 | phenylmethyl | " | H | H | " | phenyl | H | 166–168 | C₂₆H₂₂N₂O₂ | F |
| 82 | cyclohexylmethyl | C₂H₅ | " | " | " | H | CH₃ | | C₂₂H₂₈N₂O₂ | A |
| 83 | 4-methylphenylmethyl | n-C₃H₇ | " | " | " | " | " | 181–183 | C₂₄H₂₆N₂O₂ | A |
| 84 | cyclohexylmethyl | " | " | " | " | " | " | | C₂₃H₃₀N₂O₂ | A |
| 85 | cyclohexylmethyl | n-C₄H₉ | H | H | H | H | CH₃ | | C₂₄H₃₂N₂O₂ | A |
| 86 | 4-methylpheylmethyl | iso-C₄H₉ | " | " | " | " | | | C₂₅H₂₈N₂O₂ | A |
| 87 | cyclohexylmethyl | " | " | " | " | " | | | C₂₄H₃₂N₂O₂ | A |
| 88 | 4-methylphenylmethyl | n-C₅H₁₁ | " | " | " | " | | 151–152.5 | C₂₆H₃₀N₂O₂ | A |
| 89 | phenylmethyl | C₂H₅ | 2-CH₃ | " | " | " | | | C₂₃H₂₄N₂O₂ | A |
| 90 | 4-chloro- | " | " | " | " | " | | | C₂₃H₂₃ClN₂O₂ | A |
| 91 | phenylmethyl | nC₄H₉ | " | " | " | " | | 161–163.5 | C₂₅H₂₈N₂O₂ | A |
| 92 | 4-chlorophenylmethyl | " | " | " | " | " | | | C₂₅H₂₇ClN₂O₂ | A |
| 93 | phenylmethyl | nC₅H₁₁ | " | " | " | " | | 111.5–113 | C₂₆H₃₀N₂O₂ | A |
| 94 | 4-chloro- | " | " | " | " | " | | 155–156.5 | C₂₆H₂₉ClN₂O₂ | A |
| 95 | phenylmethyl | C₂H₅ | 2-Cl | " | " | " | | 174.5–177 | C₂₂H₂₁ClN₂O₂ | A |
| 96 | phenylmethyl | nC₃H₇ | " | " | " | " | | 171–171.5 | C₂₂H₂₃ClN₂O₂ | A |
| 97 | phenylmethyl | nC₄H₉ | 2-Cl | H | H | H | CH₃ | 121–123 | C₂₄H₂₅N₂O₂ | A |
| 98 | phenylmethyl | nC₃H₇ | 2-CH₃ | 3-CH₃ | " | " | " | 126–128 | C₂₅H₂₈N₂O₂ | A |
| 99 | phenylmethyl | methoxymethyl | H | H | " | " | " | | C₂₂H₂₂N₂O₃ | A |
| 100 | phenylmethyl | 2-methyl- | " | " | " | " | " | 173–174 | C₂₇H₂₄N₂O₂ | A |
| 101 | phenylmethyl | 3-methyl- | " | " | " | " | " | 202.5– | C₂₇H₂₄N₂O₂ | A |

TABLE 1-continued

| Example NO. | R | $R_2$ | $R_3$ | $R_4$ | $R_5$ | $R_6$ | $R_7$ | Melting point (°C.) | Molecular formula | Method |
|---|---|---|---|---|---|---|---|---|---|---|
| 102 | phenylmethyl | phenyl 2-chloro-phenyl | " | " | " | " | " | 204.5 194–196 | $C_{26}H_{21}ClN_2O_2$ | A |
| 103 | phenylmethyl | 2-furyl | " | " | " | " | " | | $C_{24}H_{20}N_2O_3$ | A |
| 104 | methyl | $nC_4H_9$ | 2-$C_2H_5$ | 6-$C_2H_5$ | " | " | " | 95.5–96 | $C_{22}H_{30}N_2O_2$ | B |
| 105 | methyl | " | " | " | " | Br | " | 180–180.5 | $C_{22}H_{29}BrN_2O_2$ | D |
| 106 | methyl | " | " | " | " | $CH_3$ | $CH_3$ | 114.5–115.5 | $C_{23}H_{32}N_2O_2$ | B |
| 107 | methyl | " | " | " | 4-Br | H | " | 170.5–171.0 | $C_{22}H_{29}BrN_2O_2$ | B |
| 108 | methyl | " | " | " | " | Br | " | 179.5–180 | $C_{22}H_{28}Br_2N_2O_2$ | D |
| 109 | methyl | $nC_4H_9$ | 2-$C_2H_5$ | 6-$C_2H_5$ | 4-Br | $CH_3$ | $CH_3$ | 139.0–140.0 | $C_{23}H_{31}BrN_2O_2$ | B |
| 110 | methyl | $nC_3H_7$ | " | " | H | " | " | 148–150.5 | $C_{26}H_{30}N_2O_2$ | B |
| 111 | methyl | " | " | " | 4-Br | " | " | 156.0–156.5 | $C_{26}H_{29}BrN_2O_2$ | B |
| 112 | methyl | $nC_5H_{11}$ | " | " | H | H | " | 98–98.5 | $C_{24}H_{34}N_2O_2$ | B |
| 113 | 3-chlorophenyl | $nC_4H_9$ | H | H | " | " | " | 210–211 | $C_{23}H_{23}ClN_2O_2$ | B |
| 114 | 3-bromophenyl | " | " | " | " | " | " | 204–205 | $C_{23}H_{23}BrN_2O_2$ | B |
| 115 | 3,5-bistri-fluoromethyl-phenyl | " | " | " | " | " | " | 248–249 | $C_{25}H_{22}F_6N_2O_2$ | B |
| 116 | 3-trifluoromethylphenyl | " | " | " | " | " | " | 175–176 | $C_{24}H_{23}F_3N_2O_2$ | B |
| 117 | 3-methylphenyl | " | " | " | " | " | " | 110.5–111 | $C_{24}H_{26}N_2O_2$ | B |
| 118 | 3-iodophenyl | " | " | " | " | " | " | 211.5–216.5 | $C_{23}H_{23}IN_2O_2$ | B |
| 119 | 3-fluorophenyl | " | " | " | " | " | " | 185.5–187 | $C_{23}H_{23}FN_2O_2$ | B |
| 120 | 3-ethylphenyl | " | " | " | " | " | " | 142–142.5 | $C_{25}H_{28}N_2O_2$ | B |
| 121 | 3,5-dichloro-phenyl | $nC_4H_9$ | H | H | H | H | $CH_3$ | 218–218.5 | $C_{23}H_{22}Cl_2N_2O_2$ | B |
| 122 | 3-methoxyphenyl | $n-C_4H_9$ | " | " | " | " | " | 140–142 | $C_{24}H_{26}N_2O_3$ | B |
| 123 | 2,3-dichloro-phenyl | " | " | " | " | " | " | 178–180 | $C_{23}H_{22}ClN_2O_2$ | B |
| 124 | 3,4-dichloro-phenyl | " | " | " | " | " | " | 199.5–200.0 | $C_{23}H_{22}Cl_2N_2O_2$ | B |
| 125 | 3-chlorophenyl | " | 2-$CH_3$ | 3-$CH_3$ | " | " | " | 123–124 | $C_{25}H_{27}ClN_2O_2$ | B |
| 126 | 3-chlorophenyl | " | 2-$C_2H_5$ | 6-$C_2H_5$ | " | " | " | 178–178.5 | $C_{27}H_{31}ClN_2O_2$ | B |
| 127 | 3-chlorophenyl | phenyl | " | " | " | " | " | 242–243 | $C_{29}H_{27}ClN_2O_2$ | B |
| 128 | H | $nC_4H_9$ | 2-$C_2H_5$ | 6-$C_2H_5$ | H | H | $CH_3$ | oil | $C_{21}H_{28}N_2O_2$ | B |
| 129 | H | 3-bromophenyl | H | H | " | " | " | 286.5–289 | $C_{19}H_{15}BrN_2O_2$ | B |
| 130 | methyl | $nC_3H_7$ | 2-$C_2H_5$ | 6-$C_2H_5$ | " | " | " | 99.5–100.5 | $C_{21}H_{28}N_2O_2$ | B |
| 131 | methyl | " | " | " | 4-Br | " | " | 159.0–160.0 | $C_{21}H_{27}BrN_2O_2$ | B |
| 132 | methyl | " | " | " | 4-I | " | " | | $C_{21}H_{27}IN_2O_2$ | B |
| 133 | methyl | $nC_3H_7$ | 2-$C_2H_5$ | 6-$C_2H_5$ | 4-$OCH_3$ | H | $CH_3$ | | $C_{22}H_{30}N_2O_3$ | B |
| 134 | methyl | " | " | " | 4-$C_2H_5$ | " | " | | $C_{23}H_{32}N_2O_2$ | B |
| 135 | methyl | 3-chloro-phenyl | H | H | H | " | " | 191.0–192.5 | $C_{20}H_{17}ClN_2O_2$ | B |
| 136 | ethyl | $nC_4H_9$ | 2-$C_2H_5$ | 6-$C_2H_5$ | 4-Br | " | " | 143.5–145 | $C_{23}H_{31}BrN_2O_2$ | B |
| 137 | H | " | " | " | H | Br | $CH_3$ | 163–166 | $C_{21}H_{27}BrN_2O_2$ | D |
| 138 | methyl | $nC_3H_7$ | " | " | " | " | " | 183–184.5 | $C_{21}H_{27}BrN_2O_2$ | D |
| 139 | methyl | " | " | " | 4-Br | " | " | 204–205 | $C_{21}H_{26}Br_2N_2O_2$ | D |
| 140 | methyl | " | " | " | 4-$C_2H_5$ | " | " | 169–173.5 | $C_{23}H_{31}BrN_2N_2O_2$ | D |
| 141 | ethyl | $nC_4H_9$ | " | " | 4-Br | " | " | 210–210.5 | $C_{23}H_{30}Br_2N_2O_2$ | D |
| 142 | methyl | $nC_3H_7$ | " | " | 4-$C_2H_5$ | $CH_3$ | " | | $C_{24}H_{34}N_2O_2$ | B |
| 143 | methyl | " | " | " | 4-I | " | " | | $C_{22}H_{29}IN_2O_2$ | B |
| 144 | methyl | $nC_4H_9$ | " | " | 4-Br | $C_2H_5$ | " | oil | $C_{24}H_{33}BrN_2O_2$ | B |
| 145 | methyl | $nC_3H_7$ | 2-$C_2H_5$ | 6-$C_2H_5$ | H | H | $C_2H_5$ | | $C_{22}H_{30}N_2O_2$ | B |
| 146 | methyl | $nC_4H_9$ | " | " | 4-Br | $CH_3$ | " | | $C_{24}H_{33}BrN_2O_2$ | B |

TABLE 1-continued

| Example NO. | R | $R_2$ | $R_3$ | $R_4$ | $R_5$ | $R_6$ | $R_7$ | Melting point (°C.) | Molecular formula | Method |
|---|---|---|---|---|---|---|---|---|---|---|
| 147 | phenyl | " | H | H | H | H | $CH_3$ | 213.0–214.0 | $C_{23}H_{24}N_2O_2$ | B |
| 148 | 2-methylphenyl | " | " | " | " | " | " | 183.0–185.0 | $C_{24}H_{26}N_2O_2$ | B |
| 149 | 2-chlorophenyl | " | " | " | " | " | " | 153.0–154.0 | $C_{23}H_{23}ClN_2O_2$ | B |
| 150 | methyl | phenyl | 2-$C_2H_5$ | 6-$C_2H_5$ | " | $CH_3$ | " | | $C_{25}H_{28}N_2O_2$ | B |
| 151 | 3-cyanophenyl | $nC_4H_9$ | H | H | " | H | " | 207.5–209.5 | $C_{24}H_{23}N_3O_2$ | B |
| 152 | 3-nitrophenyl | " | " | " | " | " | " | 184.5–186 | $C_{23}H_{23}N_3O_4$ | B |
| 153 | 4-chlorophenyl | " | " | " | " | " | " | 192.0–192.5 | $C_{23}H_{23}ClN_2O_2$ | B |
| 154 | 4-methylphenyl | " | " | " | " | " | " | 163.5–165.0 | $C_{24}H_{26}N_2O_2$ | B |
| 155 | 3-chloro-2-methylphenyl | " | " | " | " | " | " | 163.0–164.0 | $C_{24}H_{25}ClN_2O_2$ | B |
| 156 | 3-chloro-4-methyphenyl | " | " | " | " | " | " | | $C_{24}H_{25}ClN_2O_2$ | B |
| 157 | 5-chloro-2-methylphenyl | $nC_4H_9$ | H | H | H | H | $CH_3$ | | $C_{24}H_{25}ClN_2O_2$ | B |
| 158 | 3-pyridyl | " | " | " | " | " | " | | $C_{22}H_{23}N_3O_2$ | B |
| 159 | 3-bromophenyl | " | 2-$CH_3$ | 3-$CH_3$ | " | " | " | 157.5–158.0 | $C_{25}H_{27}BrN_2O_2$ | B |
| 160 | 3-methylphenyl | " | " | " | " | " | " | 165.0–166.5 | $C_{26}H_{30}N_2O_2$ | B |
| 161 | 3-trifluoromethyphenyl | " | " | " | " | " | " | 157.5–158.0 | $C_{26}H_{27}F_3N_2O_2$ | B |
| 162 | 3-bromophenyl | " | 2-$C_2H_5$ | 6-$C_2H_5$ | " | " | " | 136.5–137.5 | $C_{27}H_{31}BrN_2O_2$ | B |
| 163 | 3-trifluoromethyphenyl | " | " | " | " | " | " | | $C_{28}H_{31}F_3N_2O_2$ | B |
| 164 | methyl | $n$-$C_3H_7$ | " | " | " | Br | $C_2H_5$ | | $C_{22}H_{29}BrN_2O_2$ | D |
| 165 | methyl | " | " | " | 4-$OCH_3$ | " | $CH_3$ | | $C_{22}H_{29}BrN_2O_3$ | D |
| 166 | methyl | " | " | " | I | " | " | | $C_{21}H_{26}BrIN_2O_2$ | D |

TABLE 2

| Example No. | IR $\nu$ value (cm$^{-1}$) | Method | NMR Chemical shift $\delta$ value | Solvent | Conc. (ppm) | Evaluation Plants X | Y | Z |
|---|---|---|---|---|---|---|---|---|
| 1 | 1617, 1663 | KBr | 1.40(3H,t), 2.26(3H,s), 3.40(2H,q), 5.22(2H,s), 6.43(1H,s), 6.70–7.75(10H,m), 12.76(1H,br) | CDCl$_3$ | 20<br>100 | 4<br>4 | 4<br>4 | 1<br>2 |
| 2 | 1600, 1638, 1664 | KBr | 1.37(3H,t), 2.26(3H,s), 2.32(3H,s), 3.25(2H,q), 5.18(2H,s), 6.43(1H,s), 6.60–7.75(9H,m), 12.83(1H,br) | " | 20<br>100 | 4<br>4 | 4<br>4 | 1<br>1 |
| 3 | 1630, 1675 | KBr | 1.04(6H,t), 0.7–2.0(6H,m), 2.31(3H,s), 3.27(2H,t), 3.87(2H,t), 6.31(1H,s), 6.90–7.60(5H,m), 12.60(1H,br) | " | 20<br>100 | 3<br>3 | 4<br>4 | 3<br>3 |
| 4 | 1627, 1667 | KBr | 0.98(3H,t), 1.80(2H,six), 2.24(3H,s), 3.18(2H,t), 5.16(2H,s), 6.40(1H,s), 6.70–7.70(10H,m), 12.75(1H,br) | " | 20<br>100 | 4<br>4 | 4<br>4 | 1<br>1 |
| 5 | 1625, 1673 | KBr | 1.07(3H,t), 1.63(2H,six), 2.31(3H,s), 2.91(2H,t), 3.36(2H,t), 4.10(2H,t), 6.32(1H,s), 6.90–7.70(10H,m), 12.69(1H,br) | " | 20<br>100 | 3<br>3 | 4<br>4 | 1<br>1 |
| 6 | 1630, 1675 | KBr | 0.89(3H,t), 1.00–2.00(4H,m), 2.25(3H,s), 3.22(2H,t), 5.19(2H,s), 6.41(1H,s), 6.70–7.70(10H,m), 12.70(1H,br) | CDCl$_3$ | 20<br>100 | 4<br>4 | 4<br>4 | 1<br>2 |
| 7 | 1640, 1665 | KBr | 0.92(3H,t), 1.10–2.20(4H,m), 2.24(3H,s), 2.30(3H,s), 3.25(2H,t), 5.15(2H,s), 6.41(1H,s), 6.70–7.75(9H,m), 12.74(1H,br) | " | 20 | 4 | 4 | 1 |
| 8 | 1620, | KBr | 0.95(6H,d), 2.90(1H,m), | " | 20 | 4 | 4 | 1 |

TABLE 2-continued

| Example No. | IR ν value (cm⁻¹) | Method | NMR Chemical shift δ value | Solvent | Conc. (ppm) | Evaluation Plants X | Y | Z |
|---|---|---|---|---|---|---|---|---|
| | 1660 | | 2.23(3H,s), 3.46(2H,d), 5.20(2H,s), 6.41(1H,s), 6.70-7.70(10H,m), 12.42(1H,br) | | | | | |
| 9 | 1627, 1670 | KBr | 0.83(3H,t), 1.00-2.10(6H,m), 2.22(3H,s), 3.23(2H,t), 5.16(2H,s), 6.40(1H,s), 6.70-7.70(10H,m), 12.63(1H,br) | " | 20 100 | 3 4 | 4 4 | 1 1 |
| 10 | 1637, 1663 | KBr | 0.83(3H,t), 1.00-2.00(10H,m), 2.22(3H,s), 3.20(2H,t), 5.14(2H,s), 6.36(1H,s), 6.70-7.75(10H,m), 12.70(1H,br) | " | 20 100 | 3 4 | 4 4 | 1 1 |
| 11 | 1600, 1630, 1670 | Neat | 0.86(3H,t), 0.90-2.00(14H,m), 2.24(3H,s), 3.20(2H,t), 5.18(2H,s), 6.40(1H,s), 6.70-7.70(10H,m), 12.65(1H,br) | CDCl₃ | 20 100 | 3 3 | 4 4 | 1 1 |
| 12 | 1623, 1660 | KBr | 2.23(3H,s), 4.70(2H,s), 5.00(2H,s), 6.47(1H,s), 6.60-7.65(15H,m), 12.83(1H,br) | " | 20 100 | 1 1 | 4 4 | 1 1 |
| 13 | 1627, 1657 | KBr | 2.20(3H,s), 2.31(3H,s), 4.73(2H,s), 5.00(2H,s), 6.50(1H,s), 6.65-7.70(15H,m), 12.83(1H,br) | " | 20 100 | 2 2 | 4 4 | 1 1 |
| 14 | 1610, 1640, 1660 | KBr | | | 20 100 | 1 2 | 3 4 | 1 1 |
| 15 | 1625, 1663 | KBr | 2.36(3H,s), 3.14(3H,s), 6.51(1H,s), 6.85-7.60(10H,m), 12.53(1H,br) | CDCl₃ | 20 100 | 2 2 | 3 4 | 3 5 |
| 16 | 1617, 1663 | KBr | 1.06(3H,t), 2.42(3H,s), 3.68(2H,q), 6.51(1H,s), 6.90-7.60(10H,m), 12.45(1H,br) | CDCl₃ | 20 100 | 1 4 | 4 4 | 1 1 |
| 17 | 1617, 1677 | KBr | 0.59(3H,t), 1.45(2H,six), 2.40(3H,s), 3.48(2H,t), 6.48(1H,s), 6.80-7.65(10H,m), 12.50(1H,br) | " | 20 100 | 4 4 | 4 4 | 1 1 |
| 18 | 1600, 1617, 1680 | KBr | 0.66(3H,t), 0.50-1.80(4H,m), 2.40(3H,s), 3.58(2H,t), 6.51(1H,s), 6.60-7.65(10H,m), 12.49(1H,br) | " | 20 100 | 3 3 | 4 4 | 1 2 |
| 19 | 1617, 1675 | KBr | 0.71(3H,t), 0.50-1.70(6H,m), 2.38(3H,s), 3.50(2H,t), 6.32(1H,s), 6.80-7.50(10H,m), 12.53(1H,br) | " | 20 100 | 4 4 | 4 4 | 1 3 |
| 20 | 1617, 1675 | KBr | 0.77(3H,t), 0.50-1.80(8H,m), 2.41(3H,s), 3.57(2H,t), 6.51(1H,s), 6.85-7.60(10H,m), 12.57(1H,br) | " | 20 100 | 4 4 | 4 4 | 1 1 |
| 21 | 1600, 1620, 1680 | KBr | 0.58(3H,t), 0.40-1.60(12H,m), 2.38(3H,s), 3.66(2H,t), 6.43(1H,s), 6.80-7.50(10H,m), 12.07(1H,br) | CDCl₃ | 20 100 | 4 4 | 4 4 | 1 1 |
| 22 | 1617, 1677 | KBr | 1.67(2H,m), 2.40(3H,s), 3.00(2H,t), 3.12(3H,s), 3.70(2H,t), 6.48(1H,s), 6.80-7.60(10H,m), 12.46(1H,br) | " | 20 100 | 3 3 | 4 5 | 1 1 |
| 23 | 1623, 1670 | KBr | 2.44(3H,s), 3.12(3H,s), 3.22(2H,t), 3.85(2H,t), 6.48(1H,s), 6.80-7.60(10H,m), 12.35(1H,br) | " | 20 100 | 4 4 | 4 4 | 1 1 |
| 24 | 1623, 1675 | KBr | | | 20 100 | 1 1 | 4 4 | 1 1 |
| 25 | 1620, 1675 | KBr | 2.27(3H,s), 4.89(2H,s) 6.59(1H,s), 6.55-7.60(15H,m), 12.46(1H,br) | CDCl₃ | 20 100 | 4 4 | 4 4 | 1 1 |
| 26 | 1620, 1673 | KBr | 2.25(3H,s), 2.28(3H,s), 4.79(2H,s), 6.55(1H,s), 6.50-7.60(14H,m), 12.48(1H,br) | CDCl₃ | 20 100 | 4 4 | 4 4 | 1 1 |
| 27 | 1625, 1665 | KBr | 2.25(3H,s), 4.80(2H,s), 6.58(1H,s), 6.55-7.60(14H,m), 12.38(1H,br) | " | 20 100 | 4 4 | 4 4 | 1 1 |

TABLE 2-continued

| Example No. | IR ν value (cm⁻¹) | Method | NMR Chemical shift δ value | Solvent | Conc. (ppm) | Evaluation Plants X | Y | Z |
|---|---|---|---|---|---|---|---|---|
| 28 | 1613, 1673 | KBr | 2.42(3H,s), 2.68(2H,t), 3.80(2H,t), 6.52(1H,t), 6.50–7.60(15H,m), 12.43(1H,br) | " | 20 100 | 1 3 | 4 4 | 1 1 |
| 29 | 1623, 1673 | KBr | 2.43(3H,s), 4.78(2H,s), 5.75(1H,m), 6.20(1H,dd), 6.50(1H,s), 6.80–7.55(11H,m), 12.35(1H,br) | " | 20 100 | 4 4 | 4 4 | 1 1 |
| 30 | 1617, 1667 | KBr | 2.30(3H,s), 4.91(2H,s), 6.58(1H,s), 6.50–8.45(14H,m), 12.53(1H,br) | " | 20 100 | 4 4 | 4 4 | 1 1 |
| 31 | 1615, 1665 | KBr | 2.30(3H,s), 4.82(2H,s), 6.59(1H,s), 6.60–7.60(14H,m), 12.60(1H,br) | CDCl₃ | 20 100 | 4 4 | 4 4 | 1 1 |
| 32 | 1623, 1670 | KBr | 2.26(3H,s), 4.82(2H,s), 6.57(1H,s), 6.55–7.60(14H,m), 12.55(1H,br) | " | | | | |
| 33 | 1623, 1673 | KBr | 2.22(3H,s), 2.30(3H,s), 4.82(2H,s), 6.52(1H,s), 6.55–7.60(14H,m), 12.39(1H,br) | " | 20 100 | 3 3 | 4 4 | 1 1 |
| 34 | 1625, 1675 | Neat | 2.23(3H,s), 4.86(2H,s), 6.18(1H,m), 6.35(1H,dd), 6.57(1H,s), 6.70–7.70(11H,m), 12.30(1H,br) | " | 20 100 | 4 4 | 4 4 | 1 3 |
| 35 | 1623, 1660 | KBr | 1.00(3H,t), 1.75(2H,six), 2.24(3H,s), 2.40(3H,s), 3.20(2H,t), 5.17(2H,s), 6.39(1H,s), 6.70–8.05(9H,m), 12.43(1H,br) | " | 20 100 | 4 4 | 4 4 | 1 1 |
| 36 | 1630, 1675 | KBr | 1.00(3H,t), 1.75(2H,six) 2.21(3H,s), 2.39(3H,s), 3.20(2H,t), 5.11(2H,s), 6.38(1H,s), 6.70–8.05(8H,m), 12.50(1H,br) | CDCl₃ | 20 100 | 4 4 | 4 4 | 1 2 |
| 37 | 1627, 1653 | KBr | 1.06(3H,t), 1.75(2H,six), 2.30(3H,s), 2.37(3H,s), 2.90(2H,t), 3.40(2H,t), 4.08(2H,t), 6.30(1H,s), 6.80–8.00(9H,m), 12.50(1H,br) | " | 20 100 | 4 4 | 4 4 | 2 2 |
| 38 | 1610, 1675 | KBr | 0.66(3H,t), 0.50–1.80(4H,m), 2.32(3H,s), 2.39(3H,s), 3.50(2H,t), 6.51(1H,s), 6.80–7.90(9H,m), 12.25(1H,br) | " | 20 100 | 4 4 | 4 4 | 1 3 |
| 39 | 1623, 1667 | KBr | 2.27(3H,s), 2.36(3H,s), 4.83(2H,s), 6.57(1H,s), 6.55–7.85(14H,m), 12.28(1H,br) | " | 20 100 | 4 4 | 4 4 | 1 2 |
| 40 | 1623, 1673 | KBr | 2.27(3H,s), 2.35(3H,s), 4.81(2H,s), 6.57(1H,s), 6.55–7.85(13H,m), 12.21(1H,br) | " | 20 100 | 3 4 | 4 4 | 1 2 |
| 41 | 1623, 1680 | KBr | 0.65(3H,t), 0.40–1.80(4H,m), 2.41(3H,s), 3.52(2H,t), 6.50(1H,s), 6.70–8.17(9H,m), 12.90(1H,br) | CDCl₃ | 20 100 | 4 4 | 4 4 | 1 1 |
| 42 | 1607, 1680 | KBr | 0.65(3H,t), 0.40–1.80(4H,m), 2.12(3H,s), 2.21(3H,s), 2.43(3H,s), 3.62(2H,t), 6.46(1H,s), 6.70–7.50(8H,s), 11.63(1H,br) | CDCl₃ + DMSO-d⁶ | 20 100 | 4 4 | 4 4 | 1 1 |
| 43 | 1605, 1617, 1677 | KBr | 2.20(6H,s), 2.23(3H,s), 4.81(2H,s), 6.53(1H,s), 6.50–7.60(13H,m), 12.05(1H,m) | CDCl₃ | 20 100 | 4 4 | 4 4 | 1 1 |
| 44 | 1603, 1625 1675 | KBr | 2.20(6H,ms), 2.42(3H,s), 2.66(2H,t), 3.80(2H,t), 6.50(1H,s), 6.50–7.60(13H,m), 12.00(1H,br) | " | 20 100 | 1 1 | 2 3 | 1 1 |
| 45 | 1620, 1675 | KBr | 0.67(3H,t), 0.40–1.80(4H,m), 2.20(6H,s), 2.40(3H,s), 3.60(2H,t), 6.49(1H,s), 6.87–7.20(8H,m), 11.13(1H,br) | " | 20 100 | 3 3 | 4 4 | 5 5 |
| 46 | 1625, | KBr | 2.10(6H,s), 2.24(3H,s), | CDCl₃ | 20 | 4 | 4 | 1 |

TABLE 2-continued

| Example No. | IR ν value (cm⁻¹) | Method | NMR Chemical shift δ value | Solvent | Conc. (ppm) | Plants X | Y | Z |
|---|---|---|---|---|---|---|---|---|
| | 1650 | | 4.84(2H,s), 6.60(1H,s), 6.60-7.30(13H,m), 11.05(1H,br) | | 100 | 4 | 4 | 1 |
| 47 | 1630, 1675 | KBr | 1.06(3H,t), 1.18(6H,t), 0.75-2.10(4H,m), 2.35(3H,s), 2.63(4H,q), 3.89(2H,t), 6.43(1H,s), 7.25(3H,s), 8.44(1H,s), 11.80(1H,br) | " | 20 100 | 1 1 | 2 2 | 4 4 |
| 48 | 1630, 1660 | Neat | 1.20(6H,t), 0.70-2.00(10H,m), 2.40(3H,s), 2.65(4H,q), 3.35(2H,q), 3.90(2H,t), 6.37(1H,s), 7.03(3H,s), 11.80(1H,br) | " | 20 100 | 3 5 | 3 4 | 5 5 |
| 49 | 1630, 1660 | Neat | 1.20(6H,t), 1.33(3H,t), 2.27(3H,s), 2.70(4H,q), 3.30(2H,q), 5.23(2H,s), 6.49(1H,s), 6.80-7.50(8H,m), 11.81(1H,br) | " | 20 100 | 1 3 | 2 4 | 3 5 |
| 50 | 1630, 1650 | Neat | 1.19(6H,t), 1.21(3H,t), 2.35(3H,s), 2.66(4H,q), 2.95(2H,t), 3.37(2H,q), 4.15(2H,t), 6.39(1H,s), 7.00-7.40(8H,m), 11.70(1H,br) | " | 20 100 | 5 5 | 5 5 | 5 5 |
| 51 | 1625, 1660 | KBr | 1.18(6H,t), 0.80-2.10(10H,m), 2.37(3H,s), 2.67(4H,q), 3.30(2H,t), 3.85(2H,t), 6.39(1H,s), 7.03(3H,s), 11.80(1H,br) | CDCl₃ | 20 100 | 1 4 | 1 4 | 3 4 |
| 52 | 1627, 1650, 1663 | Neat | 1.17(6H,t), 0.60-2.00(12H,m), 2.37(3H,s), 2.65(4H,q), 3.20(2H,t), 3.90(2H,t), 6.37(1H,s), 7.03(3H,s), 11.82(1H,br) | " | 20 100 | 2 4 | 3 4 | 5 5 |
| 53 | 1630, 1665 | KBr | 0.95(3H,t), 1.19(6H,t), 1.70(2H,six), 2.26(3H,s), 2.70(4H,q), 3.23(2H,t), 5.18(2H,s), 6.44(1H,s), 6.80-7.50(8H,m), 11.80(1H,br) | " | 20 100 | 3 3 | 4 4 | 1 4 |
| 54 | 1630, 1665 | Neat | 1.18(6H,t), 0.60-2.00(14H,m), 2.38(3H,s), 2.65(4H,q), 3.23(2H,t), 3.92(2H,t), 6.39(1H,s), 7.03(3H,s), 11.78(1H,br) | " | 20 100 | 2 4 | 1 4 | 4 4 |
| 55 | 1647 | Neat | 0.98(6H,d), 1.17(6H,t), 0.50-2.00(8H,m), 2.39(3H,s), 2.65(4H,q), 3.22(2H,d), 3.95(2H,t), 6.38(1H,s), 7.02(3H,s), 12.05(1H,s) | " | 20 100 | 1 5 | 2 5 | 4 4 |
| 56 | 1630, 1660 | Neat | 0.91(3H,t), 1.10(6H,t), 0.70-2.00(4H,m), 2.36(3H,s), 2.55(4H,q), 3.80(2H,t), 4.93(2H,s), 6.46(1H,s), 7.00-7.35(8H,m), 12.70(1H,br) | CDCl₃ | 20 100 | 3 5 | 4 4 | 5 5 |
| 57 | 1620, 1667 | KBr | 0.59(3H,t), 1.10(6H,t), 0.50-1.80(4H,m), 2.43(3H,s), 2.50(4H,q), 3.62(2H,t), 6.53(1H,s), 7.00-7.50(8H,m), 11.06(1H,br) | " | 20 100 | 2 4 | 4 4 | 4 4 |
| 58 | 1623, 1673 | KBr | | | 20 100 | 4 4 | 4 4 | 1 1 |
| 59 | 1625, 1667 | KBr | 1.10(6H,t), 2.29(3H,s), 2.50(4H,q), 4.91(2H,s), 6.60(1H,s), 6.60-7.40(13H,m), 10.98(1H,br) | CDCl₃ | 20 100 | 4 4 | 4 4 | 1 3 |
| 60 | 1620, 1660 | KBr | 1.10(6H,t), 2.44(3H,s), 2.50(4H,q), 2.67(2H,t), 3.83(2H,t), 6.50(1H,s), 6.50-7.40(13H,m), 11.02(1H,br) | " | 20 100 | 1 1 | 1 2 | 1 1 |
| 61 | 1600, 1620, 1665 | KBr | 1.10(6H,t), 1.90(3H,s), 2.02(3H,s), 2.52(4H,q), 6.59(1H,s), 6.80-7.10(12H,m), 11.02(1H,br) | CDCl₃ | 20 100 | 3 3 | 4 4 | 3 4 |
| 62 | 1620, 1673 | KBr | | | 20 100 | 2 3 | 3 4 | 1 1 |
| 63 | 1660 | Neat | 1.18(6H,t), 0.80-2.00(10H,m), 2.65(4H,q), 2.74(3H,s), 3.32(2H,q), 4.06(2H,t), 7.10(3H,s), 11.20(1H,br) | CDCl₃ | 20 100 | 4 5 | 5 5 | 5 5 |

TABLE 2-continued

| Example No. | IR ν value (cm⁻¹) | Method | NMR Chemical shift δ value | Solvent | Conc. (ppm) | Evaluation Plants | | |
|---|---|---|---|---|---|---|---|---|
| | | | | | | X | Y | Z |
| 64 | 1625, 1660 | KBr | 1.19(3H,t), 2.51(2H,q), 2.82(3H,s), 5.16(2H,s), 6.43(1H,s), 6.70–7.75(10H,m), 12.68(1H,br) | " | 20 100 | 4 4 | 4 4 | 2 2 |
| 65 | 1600, 1620, 1673 | KBr | 0.93(3H,t), 1.65(2H,six), 2.45(2H,t), 2.87(3H,s), 5.25(2H,s), 6.40(1H,s), 6.70–7.75(10H,m), 12.70(1H,br) | " | 20 100 | 3 3 | 3 3 | 1 1 |
| 66 | 1600, 1630, 1665 | KBr | 0.62(3H,t), 0.50–1.80(4H,m), 2.95(3H,s), 3.85(2H,t), 6.36(1H,s), 6.90–7.75(10H,m), 12.60(1H,br) | CDCl₃ | 20 100 | | | |
| 67 | 1600, 1615, 1665 | KBr | 2.85(3H,s), 5.09(2H,s), 6.47(1H,s), 6.64–7.75(15H,m), 12.53(1H,br) | " | 20 100 | 1 2 | 1 1 | 1 2 |
| 68 | 1607, 1630, 1680 | KBr | 2.76(3H,s), 5.30(2H,s), 6.47(1H,s), 6.72–7.75(10H,m), 11.62(1H,br) | " | 20 100 | 2 3 | 4 4 | 1 1 |
| 69 | 1620, 1650 | KBr | 1.19(6H,t), 0.80–2.00(10H,m), 2.65(6H,q), 2.90(3H,s), 3.93(2H,t), 6.42(1H,s), 7.06(3H,s), 11.71(1H,br) | " | 20 100 | 4 5 | 4 5 | 5 5 |
| 70 | 1625, 1660 | KBr | 1.18(6H,t), 1.22(3H,t), 2.55(2H,q), 2.65(4H,q), 2.79(3H,s), 5.20(2H,s), 6.49(1H,s), 6.80–7.50(8H,m), 11.80(1H,br) | " | 20 100 | 1 3 | 1 4 | 4 4 |
| 71 | 1627, 1650 | KBr | 1.19(6H,t), 1.27(3H,t), 2.63(2H,q), 2.65(4H,q), 2.92(3H,s), 2.90(2H,t), 4.18(2H,t), 6.42(1H,s), 7.00–7.30(8H,m), 11.75(1H,br) | CDCl₃ | 20 100 | 4 5 | 5 5 | 5 5 |
| 72 | 1605, 1650 | KBr | 1.18(6H,t), 0.80–2.00(10H,m), 2.65(4H,q), 2.84(3H,s), 3.08(2H,q), 4.00(2H,t), 7.06(3H,s), 11.05(1H,br) | " | 20 100 | 1 4 | 2 4 | 5 5 |
| 73 | 1615, 1645, 1665 | KBr | 1.16(6H,t), 1.27(3H,t), 2.65(4H,q), 2.85(3H,s), 3.00(2H,t), 3.05(2H,q), 4.22(2H,t), 6.95–7.30(8H,m), 10.89(1H,br) | " | 20 100 | 4 5 | 5 5 | 5 5 |
| 74 | 1630, 1660 | KBr | 1.18(6H,t), 0.80–2.00(12H,m), 2.60(2H,t), 2.65(4H,q), 2.86(3H,s), 3.90(2H,t), 6.38(1H,s), 7.02(3H,s), 11.72(1H,br) | " | 20 100 | 2 5 | 3 5 | 5 5 |
| 75 | 1625, 1660 | KBr | 1.00(3H,t), 1.19(6H,t), 1.20–1.70(2H,m), 2.52(2H,t), 2.63(4H,q), 2.89(3H,s), 2.95(2H,t), 4.11(2H,t), 6.38(1H,s), 6.95–7.30(8H,m), 11.57(1H,br) | " | 20 100 | 1 2 | 1 3 | 3 4 |
| 76 | 1630, 1653 | KBr | 1.18(6H,t), 2.63(4H,q), 2.96(3H,s), 3.00(2H,t), 4.23(2H,t), 6.97(1H,s), 6.95–7.30(8H,m), 10.88(1H,br) | CDCl₃ | 20 100 | 4 5 | 4 5 | 3 3 |
| 77 | 1630, 1660 | KBr | 1.20(6H,t), 0.80–2.00(14H,m), 2.60(2H,t), 2.65(4H,q), 2.86(3H,s), 3.93(2H,t), 6.40(1H,s), 7.05(3H,s), 11.73(1H,br) | " | 20 100 | 1 3 | 1 3 | 3 3 |
| 78 | 1625, 1660 | KBr | 1.20(6H,t), 0.80–1.80(7H,m), 2.60(2H,t), 2.67(4H,q), 2.93(3H,s), 2.97(2H,t) 4.15(2H,t), 6.41(1H,s), 7.00–7.40(8H,m), 11.61(1H,br) | " | 20 100 | 1 2 | 2 2 | 4 4 |
| 79 | 1655 | KBr | 1.17(6H,t), 0.80–2.00(7H,m), 2.65(4H,q), 2.83(3H,s), 3.92(2H,t), 7.02(3H,s), 7.10–7.60(6H,m), 11.57(1H,br) | " | 20 100 | 1 2 | 2 2 | 1 1 |
| 80 | 1620, 1650 | KBr | 1.19(6H,t), 1.70(4H,m), 2.62(4H,m), 2.67(4H,q), 2.93(3H,s), 2.95(2H,t), 4.20(2H,t), 7.00–7.40(8H,m), 11.72(1H,br) | " | 20 100 | 1 2 | 3 3 | 4 4 |
| 81 | 1630, 1650, | KBr | 2.79(3H,s), 5.10(2H,s), 6.80–7.70(16H,m), | CDCl₃ | 20 100 | 1 1 | 1 2 | 1 1 |

TABLE 2-continued

| Example No. | IR ν value (cm$^{-1}$) | Method | NMR Chemical shift δ value | Solvent | Conc. (ppm) | Evaluation Plants X | Y | Z |
|---|---|---|---|---|---|---|---|---|
| | 1670 | | 12.60(1H,br) | | | | | |
| 82 | | | 0.80–2.00(13H,m), 1.28(3H,s), 2.36(3H,ms), 3.80(2H,d), 6.35(1H,s), 6.80–7.80(5H,m), 12.66(1H,br) | " | 20 100 | 4 4 | 4 4 | 1 1 |
| 83 | 1630, 1673 | KBr | | | 20 100 | 4 4 | 4 4 | 1 1 |
| 84 | | | 0.70–2.10(18H,m), 2.36(3H,s), 3.78(2H,d), 6.36(1H,s), 6.80–7.75(5H,m), 12.57(1H,br) | CDCl$_3$ | 20 100 | 4 4 | 4 4 | 2 1 |
| 85 | 1625, 1670 | Neat | 0.50–2.10(20H,m), 2.34(3H,s), 3.75(2H,d), 6.30(1H,s), 6.80–7.70(5H,m), 12.60(1H,br) | " | 20 100 | 3 4 | 4 4 | 1 1 |
| 86 | 1630, 1663 | Neat | 0.97(6H,d), 1.70–2.30(3H,m), 2.25(3H,s), 2.31(3H,s), 3.50(2H,d), 5.65(2H,d), 6.40(1H,s), 6.70–7.70(9H,m), 12.45(1H,br) | CDCl$_3$ | 20 100 | 4 4 | 4 4 | 1 1 |
| 87 | 1623, 1663 | Neat | 0.60–2.30(14H,m), 0.95(6H,d), 2.32(3H,s), 3.82(2H,d), 6.33(1H,s), 6.80–7.70(5H,m), 12.38(1H,br) | " | 20 100 | 4 4 | 4 4 | 2 2 |
| 88 | 1600, 1645, 1667 | KBr | | | 20 100 | 4 3 | 4 4 | 1 1 |
| 89 | 1630, 1667 | KBr | | | 20 100 | 4 4 | 4 4 | 4 4 |
| 90 | 1633, 1667 | Neat | | | 20 100 | 4 4 | 4 4 | 1 3 |
| 91 | 1613, 1627, 1667 | KBr | | | 20 100 | 4 4 | 4 4 | 1 1 |
| 92 | 1633, 1667 | Neat | 0.70–2.00(7H,m), 2.22(3H,s), 2.39(3H,s), 3.20(2H,t), 5.13(2H,s), 6.40(1H,s), 6.70–8.07(8H,m), 12.47(1H,br) | CDCl$_3$ | 20 100 | 4 4 | 4 4 | 1 1 |
| 93 | 1610, 1627, 1657 | KBr | 0.60–2.00(9H,m), 2.26(3H,s), 2.41(3H,s), 3.26(2H,t), 5.19(2H,s), 6.41(1H,s), 6.70–8.05(9H,m), 12.54(1H,br) | " | 20 100 | 4 4 | 4 4 | 1 1 |
| 94 | 1630, 1670 | Neat | | | 20 100 | 1 1 | 4 4 | 1 1 |
| 95 | 1633, 1675 | KBr | 1.37(3H,t), 2.26(3H,s), 3.22(2H,q), 5.13(2H,s), 6.44(1H,s), 6.70–8.43(9H,m), 13.22(1H,br) | CDCl$_3$ | 20 100 | 4 4 | 4 4 | 1 2 |
| 96 | | | 1.00(3H,t), 1.77(2H,m), 2.26(3H,s), 3.20(2H,t), 5.20(2H,s), 6.43(1H,s), 6.70–8.33(9H,m), 13.18(1H,br) | CDCl$_3$ | 20 100 | 4 4 | 4 4 | 1 1 |
| 97 | 1637, 1680 | KBr | 0.70–2.00(7H,m), 2.26(3H,s), 3.18(2H,t), 5.16(2H,s), 6.39(1H,s), 6.70–8.40(9H,m), 13.18(1H,br) | " | 20 100 | 4 4 | 4 4 | 1 1 |
| 98 | 1605, 1630, 1673 | KBr | | | 20 100 | 4 4 | 4 4 | 1 3 |
| 99 | 1630, 1670 | Neat | 2.25(3H,s), 3.41(3H,s), 5.01(2H,s), 5.45(2H,s), 6.50(1H,s), 6.70–7.77(10H,m), 12.45(1H,br) | CDCl$_3$ | 20 100 | 4 4 | 4 4 | 1 1 |
| 100 | | | 2.05(3H,s), 2.30(3H,s), 4.83(2H,d), 6.31(1H,s), 6.60–7.60(14H,m), 12.50(1H,br) | " | 20 100 | 3 3 | 4 4 | 1 1 |
| 101 | 1600, 1623, 1670 | KBr | 2.16(3H,s), 2.25(3H,s), 4.79(2H,d), 6.53(1H,s), 6.50–7.60(14H,m), 12.40(1H,br) | CDCl$_3$ | 20 100 | 4 4 | 4 4 | 1 1 |
| 102 | 1627, 1677 | KBr | 2.32(3H,s), 4.66(1Hd,), 5.05(1H,d), 6.63(1H,s), 6.60–7.60(14H,m), 12.67(1H,br) | " | 20 100 | 4 4 | 4 4 | 1 1 |
| 103 | 1625, 1680 | Neat | | | 20 100 | 4 4 | 4 4 | 1 3 |
| 104 | 1630, 1657, | KBr | 0.80–2.00(7H,m), 1.18(6H,t), 2.36(3H,s), 2.65(4H,q), 3.38(2H,t), 3.60(3H,s), 6.42(1H,s), 7.08(3H,s), | CDCl$_3$ | 20 100 | 5 5 | 5 5 | 5 5 |

TABLE 2-continued

| Example No. | IR ν value (cm⁻¹) | Method | NMR Chemical shift δ value | Solvent | Evaluation Conc. (ppm) | Plants X | Y | Z |
|---|---|---|---|---|---|---|---|---|
| 105 | 1667 | KBr | 11.80(1H,br) | | 20 | 4 | 5 | 5 |
| | | | | | 100 | 4 | 5 | 5 |
| 106 | 1620, 1655 | KBr | 0.70–2.00(7H,m), 1.18(6H,t), 2.17(3H,s), 2.30(3H,s), 2.67(4H,q), 3.40(2H,t), 3.61(3H,s), 7.08(3H,s), 11.85(1H,br) | CDCl₃ | 20 100 | 4 5 | 5 5 | 5 5 |
| 107 | 1640, 1667 | KBr | 0.70–2.00(7H,m), 1.16(6H,t), 2.36(3H,s), 2.61(4H,q), 3.34(2H,t), 3.57(3H,s), 6.38(1H,s), 7.16(2H,s), 11.99(1H,br) | " | 20 100 | 5 5 | 5 5 | 5 5 |
| 108 | 1625, 1660 | KBr | 0.70–2.00(7H,m), 1.18(6H,t), 2.36(3H,s), 2.62(4H,q), 3.35(2H,t), 3.57(3H,s), 7.16(2H,s), 11.75(1H,br) | " | 20 100 | 5 5 | 5 5 | 5 5 |
| 109 | | | 0.70–2.00(7H,m), 1.16(6H,t), 2.16(3H,s), 2.40(3H,s), 2.63(4H,q), 3.33(2H,t), 3.61(3H,s), 7.16(2H,s), 12.07(1H,br) | " | 20 100 | 5 5 | 5 5 | 5 5 |
| 110 | 1620, 1650 | KBr | 1.03(3H,t), 1.20(6H,t), 1.73(2H,m), 2.17(3H,s), 2.40(3H,s), 2.63(4H,q), 3.27(2H,t), 3.62(3H,s), 7.11(3H,s), 11.83(1H,br) | " | 20 100 | 5 5 | 5 5 | 5 5 |
| 111 | 1625, 1655 | KBr | 1.17(6H,t), 0.70–2.00(5H,m), 2.16(3H,s), 2.40(3H,s), 2.62(4H,q), 3.31(2H,t), 3.61(3H,s), 7.19(2H,s), 12.04(1H,br) | CDCl₃ | 20 100 | 5 5 | 5 5 | 5 5 |
| 112 | 1620, 1657 | KBr | 0.70–2.00(9H,m), 1.18(6H,t), 2.17(3H,s), 2.30(3H,s), 2.67(4H,a), 3.40(2H,t), 3.61(3H,s), 7.00(3H,s), 11.85(1H,br) | " | 20 100 | 4 5 | 4 4 | 4 4 |
| 113 | 1630, 1677 | KBr | 0.60–1.90(7H,m), 1.89(3H,s), 4.01(2H,t), 6.41(1H,s), 6.90–7.70(9H,m), 12.73(1H,br) | " | 20 100 | 4 4 | 4 4 | 1 1 |
| 114 | 1600, 1637, 1677 | KBr | | | 20 100 | 4 4 | 4 5 | 1 1 |
| 115 | 1635, 1687 | KBr | 0.50–1.90(7H,m), 1.78(3H,s), 2.95(2H,t), 6.44(1H,s), 7.00–8.10(8H,m), 12.60(1H,br) | CDCl₃ | 20 100 | 3 4 | 5 5 | 1 1 |
| 116 | 1600, 1635, 1680 | KBr | 0.40–2.10(7H,m), 1.81(3H,s), 2.89(2H,t), 6.41(1H,s), 6.80–8.00(9H,m), 12.78(1H,br) | CDCl₃ | 20 100 | 4 4 | 4 4 | 1 1 |
| 117 | 1603, 1640, | KBr | 0.40–2.00(7H,m), 1.78(3H,s), .234(3H,s), 3.00(2H,t), 6.35(1H,s), 6.70–7.90(9H,m), 13.11(1H,br) | " | 20 100 | 4 4 | 3 3 | 1 1 |
| 118 | 1600, 1635, 1675 | KBr | 0.35–2.00(7H,m), 1.87(3H,s), 3.00(2H,t), 6.37(1H,s), 6.70–8.00(9H,m), 12.90(1H,br) | " | 20 100 | 1 1 | 4 4 | 1 1 |
| 119 | 1600, 1640, 1685 | KBr | 0.40–2.00(7H,m), 1.85(3H,s), 3.03(2H,t), 6.38(1H,s), 6.75–7.80(9H,m), 12.82(1H,br) | " | 20 100 | 4 4 | 4 4 | 1 1 |
| 120 | 1605, 1640, 1675 | KBr | 0.40–2.00(7H,m), 1.24(3H,t), 1.84(3H,s), 2.69(2H,q), 3.05(2H,t), 6.39(1H,s), 6.70–7.85(9H,m), 13.07(1H,br) | " | 20 100 | 4 4 | 4 4 | 1 1 |
| 121 | 1600, 1637, 1695 | KBr | 0.50–2.00(7H,m), 1.88(3H,s), 3.00(2H,t), 6.37(1H,s), 6.75–7.80(8H,m), 12.72(1H,br) | CDCl₃ | 20 100 | 1 1 | 4 4 | 1 1 |
| 122 | 1600, 1633, 1673 | KBr | 0.40–2.00(7H,m), 1.91(3H,s), 3.08(2H,t), 3.82(3H,s), 6.42(1H,s), 6.60–7.80(9H,m), 12.90(1H,br) | " | 20 100 | 4 4 | 4 4 | 1 1 |
| 123 | 1603, 1640, 1675 | KBr | 0.40–2.00(7H,m), 2.00–2.70(1H,m), 1.85(3H,s), 3.10–3.90(1H,m), 6.46(1H,s), 6.80–7.85(8H,m), 12.73(1H,br) | " | 20 100 | 4 4 | 4 4 | 1 1 |
| 124 | 1600, 1635, 1680 | KBr | 0.50–2.00(7H,m), 1.85(3H,s), 3.00(2H,t), 6.36(1H,s), 6.70–7.80(8H,m), 12.75(1H,br) | " | 20 100 | 4 4 | 4 4 | 1 1 |
| 125 | 1610, | KBr | 0.50–1.80(7H,m), 1.87(3H,s), | " | 20 | 4 | 4 | 1 |

TABLE 2-continued

| Example No. | IR ν value (cm⁻¹) | Method | NMR Chemical shift δ value | Solvent | Conc. (ppm) | X | Y | Z |
|---|---|---|---|---|---|---|---|---|
| | 1640, 1673 | | 2.29(6H,s), 3.03(2H,t), 6.43(1H,s), 6.40–7.83(7H,m), 12.40(1H,br) | | 100 | 4 | 4 | 2 |
| 131 | 1637, 1663 | KBr | 1.03(3H,t), 1.16(6H,t), 1.67(2H,six), 2.32(3H,s), 2.62(4H,q), 3.30(2H,t), 3.53(3H,s), 6.35(1H,s), 7.16(2H,s), 12.05(1H,br) | CDCl₃ | 20<br>100 | 5<br>5 | 5<br>5 | 5<br>5 |
| 132 | | | 1.01(3H,t), 1.16(6H,t), 1.70(2H,six), 2.34(3H,s), 2.57(4H,q), 3.30(2H,t), 3.57(3H,s), 6.38(1H,s), 7.35(2H,s), 12.00(1H,br) | " | 20<br>100 | 5<br>5 | 5<br>5 | 5<br>5 |
| 133 | | | 1.04(3H,t), 1.18(6H,t), 1.70(2H,six), 2.36(3H,s), 2.63(4H,q), 3.32(2H,t), 3.58(3H,s), 3.77(3H,s), 6.40(1H,s), 6.64(2H,s), 11.47(1H,br) | " | 20<br>100 | 5<br>5 | 5<br>5 | 5<br>5 |
| 134 | | | 1.18(6H,t), 1.22(3H,t), 0.80–2.10(5H,m), 2.35(3H,s), 2.62(6H,q), 3.32(2H,t), 3.56(3H,s), 6.37(1H,s), 6.87(2H,s), 11.60(1H,br) | " | 20<br>100 | 4<br>5 | 5<br>5 | 5<br>5 |
| 135 | 1600, 1633, 1675 | KBr | 2.32(3H,s), 3.11(3H,s), 6.47(1H,s), 6.70–7.70(9H,m), 12.75(1H,br) | " | 20<br>100 | 1<br>1 | 3<br>3 | 2<br>5 |
| 136 | 1633, 1667 | KBr | 1.18(6H,t), 1.38(3H,t) 0.70–2.00(7H,m), 2.40(3H,s), 2.64(4H,q), 3.10–3.70(2H,m), 4.02(2H,q), 6.41(1H,s), 7.20(2H,s), 12.08(1H,br) | CDCl₃ | 20<br>100 | 5<br>5 | 5<br>5 | 5<br>5 |
| 137 | 1657 | KBr | 1.16(6H,t), 0.45–2.00(7H,m), 2.44(3H,s), 2.63(4H,q), 2.80–3.40(2H,m), 7.09(3H,s), 11.75(2H,br) | " | 20<br>100 | 1<br>1 | 3<br>5 | 5<br>5 |
| 138 | 1613, 1660 | KBr | 1.03(3H,t), 1.18(6H,t), 1.70(2H,six), 2.70(3H,s), 2.68(4H,q), 3.28(2H,t), 3.68(3H,s), 7.11(3H,s), 11.07(1H,br) | " | 20<br>100 | 5<br>5 | 5<br>5 | 5<br>5 |
| 139 | 1610, 1660 | KBr | 1.03(3H,t), 1.16(6H,t), 1.70(2H,six), 2.62(4H,q), 2.69(3H,s), 3.27(2H,t), 3.67(3H,s), 7.17(2H,s), 11.27(1H,br) | " | 20<br>100 | 5<br>5 | 5<br>5 | 5<br>5 |
| 140 | 1600, 1667 | KBr | 1.03(3H,t), 1.18(6H,t), 1.23(3H,t), 1.70(2H,six), 2.61(2H,q), 2.66(4H,q), 2.68(3H,s), 3.27(2H,t), 3.67(3H,s), 6.93(2H,s), 10.86(1H,br) | " | 20<br>100 | 4<br>5 | 5<br>5 | 5<br>5 |
| 141 | 1607, 1663 | KBr | 1.17(6H,t), 1.43(3H,t), 0.60–2.00(7H,m), 2.63(4H,q), 2.75(3H,s), 3.00–3.60(2H,m), 4.14(2H,q), 7.19(2H,s), 11.35(1H,br) | CDCl₃ | 20<br>100 | 5<br>5 | 5<br>5 | 5<br>5 |
| 142 | | | 1.03(3H,t), 1.18(6H,t), 1.23(3H,t), 1.70(2H,six), 2.17(3H,s), 2.40(3H,s), 2.60(2H,q), 2.65(4H,q), 3.32(2H,t), 3.61(3H,s), 6.91(2H,s), 11.62(1H,br) | " | 20<br>100 | 4<br>5 | 5<br>5 | 5<br>5 |
| 143 | 1620, 1660 | KBr | 1.03(3H,t), 1.16(6H,t), 1.70(2H,six), 2.16(3H,s), 2.40(3H,s), 2.60(4H,q), 3.32(2H,t), 3.62(3H,s), 7.38(2H,s), 12.05(1H,br) | " | 20<br>100 | 4<br>4 | 5<br>5 | 5<br>5 |
| 144 | 1617, 1650 | KBr | 1.17(6H,t), 1.23(3H,t), 0.70–2.20(7H,m), 2.39(3H,s), 2.63(4H,q), 2.67(2H,q), 3.33(2H,t), 3.61(3H,s), 7.20(2H,s), 12.16(1H,br) | " | 20<br>100 | 5<br>5 | 5<br>5 | 5<br>5 |
| 145 | 1633, 1663 | Neat | 1.03(3H,t), 1.19(6H,t), 1.28(3H,t), 1.70(2H,six), 2.67(6H,q), 3.40(2H,t), 3.59(3H,s), 6.46(1H,s), 7.10(3H,s), 11.82(1H,br) | " | 20<br>100 | 3<br>4 | 5<br>5 | 5<br>5 |
| 146 | 1617, 1667 | KBr | 1.18(6H,t), 1.25(3H,t), 0.70–2.00(7H,m), 2.17(3H,s) | CDCl₃ | 20<br>100 | 3<br>4 | 4<br>5 | 5<br>5 |

TABLE 2-continued

| Example No. | IR ν value (cm⁻¹) | Method | NMR Chemical shift δ value | Solvent | Evaluation Conc. (ppm) | Plants X | Y | Z |
|---|---|---|---|---|---|---|---|---|
| | | | 2.65(4H,q), 2.81(2H,q), 3.10–3.60(2H,m), 3.67(3H,s), 7.19(2H,s), 12.08(1H,br) | | | | | |
| 147 | 1625, 1690 | KBr | 0.40–1.20(7H,m), 1.83(3H,s), 3.02(2H,t), 6.41(1H,s), 6.80–7.90(10H,m), 13.02(1H,br) | " | 20 100 | 4 4 | 4 4 | 1 1 |
| 148 | 1633, 1677 | KBr | 0.35–2.00(7H,m), 1.73(3H,s), 1.93(3H,s), 2.00–2.55(1H,m), 3.25–3.95(1H,m), 6.43(1H,s), 6.70–7.85(9H,m), 13.13(1H,br) | " | 20 100 | 4 4 | 4 4 | 1 1 |
| 149 | 1603, 1640, 1673 | KBr | 0.40–2.00(7H,m), 1.84(3H,s), 2.00–3.90(2H,m), 6.40(1H,s), 6.80–8.00(9H,m), 12.87(1H,br) | " | 20 100 | 4 4 | 4 4 | 1 1 |
| 150 | | | 1.10(6H,t), 2.24(3H,s), 2.41(3H,s), 2.51(4H,q), 3.23(3H,s), 6.85–7.55(8H,m), 11.23(1H,br) | " | 20 100 | 4 5 | 5 5 | 5 5 |
| 151 | 1633, 1680, 2280 | KBr | 0.40–2.00(7H,m), 1.81(3H,s), 2.97(2H,t), 6.43(1H,s), 6.80–8.00(9H,m), 12.63(1H,br) | CDCl₃ | 20 100 | 4 4 | 4 4 | 1 1 |
| 152 | 1600, 1637, 1680 | KBr | 0.40–2.00(7H,m), 1.87(3H,s), 2.97(2H,t), 6.44(1H,s), 6.80–8.70(9H,m), 12.60(1H,br) | CDCl₃ -DMSO-d⁶ | 20 100 | 4 4 | 3 4 | 1 1 |
| 153 | 1633, 1685 | KBr | 0.40–2.00(7H,m), 1.82(3H,s), 3.01(2H,t), 6.37(1H,s), 6.80–7.85(9H,m), 12.82(1H,br) | CDCl₃ | 20 100 | 1 1 | 4 4 | 1 1 |
| 154 | 1600, 1633, 1675 | KBr | 0.40–2.00(7H,m), 1.86(3H,s), 2.41(3H,s), 2.83(2H,t), 6.33(1H,s), 6.80–8.00(9H,m), 12.56(1H,br) | CDCl₃ -DMSO-d⁶ | 20 100 | 4 4 | 4 4 | 1 1 |
| 155 | 1600, 1637, 1673 | KBr | 0.40–2.00(7H,m), 1.80(3H,s), 2.05(3H,s), 2.00–2.60(1H,m), 3.25–3.90(1H,m), 6.46(1H,s), 6.80–7.80(8H,m) 12.90(1H,br) | CDCl₃ | 20 100 | 4 4 | 4 4 | 1 1 |
| 156 | | | 0.40–2.00(7H,m), 1.86(3H,s), 2.45(3H,s), 3.03(2H,t), 6.40(1H,s), 6.80–7.85(8H,s), 12.85(1H,br), | CDCl₃ | 20 100 | 4 4 | 4 4 | 1 1 |
| 157 | | | 0.30–2.50(7H,m), 1.83(3H,s), 1.98(3H,s), 1.90–2.50(1H,m), 3.20–4.10(1H,m), 6.49(1H,s), 6.75–7.90(8H,m), 12.87(1H,s) | " | 20 100 | 4 4 | 3 3 | 1 1 |
| 158 | | | 0.40–2.00(7H,m), 1.79(3H,s), 2.50–3.40(2H,m), 6.42(1H,s), 6.80–8.90(9H,m), 12.70(1H,s), | " | 20 100 | 1 4 | 4 4 | 1 1 |
| 159 | 1613, 1637, 1683 | KBr | 0.40–2.00(7H,m), 1.88(3H,s), 2.31(6H,s), 3.03(2H,t), 6.42(1H,s), 6.75–7.90(7H,m), 12.41(1H,br) | " | 20 100 | 4 4 | 4 4 | 1 1 |
| 160 | 1605, 1637, 1673 | KBr | 0.40–2.00(7H,m), 1.88(3H,s), 2.29(6H,s), 2.41(3H,s), 3.05(2H,t), 6.42(1H,s), 6.70–7.90(7H,m), 12.56(1H,br) | " | 20 100 | 4 4 | 4 4 | 1 2 |
| 161 | 1613, 1640, 1680 | KBr | 0.40–2.00(7H,m), 1.86(3H,s), 2.30(6H,s), 2.50–3.50(2H,m), 6.44(1H,s), 6.70–8.00(7H,m), 12.38(1H,br) | CDCl₃ | 20 100 | 4 4 | 4 4 | 1 2 |
| 162 | 1635, 1667 | KBr | 0.40–2.00(7H,m), 1.22(6H,t), 2.50–3.50(2H,m), 6.47(1H,s), 2.50–3.50(2H,m), 6.47(1H,s), 6.80–8.00(7H,m), 11.93(1H,br) | " | 20 100 | 3 4 | 4 4 | 2 2 |
| 163 | 1633, 1665 | KBr | 0.40–2.00(7H,m), 1.19(6H,t), 1.87(3H,s), 2.65(4H,q), 2.20–4.10(2H,m), 6.47(1H,s), 6.80–7.90(7H,m), 11.85(1H,br) | " | 20 100 | 1 4 | 2 5 | 1 3 |
| 164 | | | 1.03(3H,t), 1.16(6H,t), 1.29(3H,t), 1.70(2H,six), 2.63(4H,q), 3.07(2H,q), 3.27(2H,t), 3.72(3H,s), 7.06(3H,s), 10.95(1H,br) | " | 20 100 | 5 5 | 5 5 | 5 5 |
| 165 | | | 1.04(3H,t), 1.18(6H,t), 1.70(2H,six), 2.64(4H,q), 2.76(3H,s), 3.34(2H,t), 3.68(3H,s), 3.77(3H,s), 6.64(2H,s), 10.64(1H,br) | " | 20 100 | 5 5 | 5 5 | 5 |

TABLE 2-continued

| Example No. | IR v value (cm$^{-1}$) | Method | NMR Chemical shift δ value | Solvent | Evaluation Conc. (ppm) | Plants X | Y | Z |
|---|---|---|---|---|---|---|---|---|
| 166 | | | 1.01(3H,t), 1.18(6H,t), 1.70(2H,six), 2.74(3H,s), 2.61(4H,q), 3.32(2H,t), 3.76(3H,s), 7.39(2H,s), 11.13(1H,br) | CDCl$_3$ | 20 100 | 5 5 | 5 5 | 5 5 |

X: *Oryza sativa L.*
Y: *Echinochloa crus-galli L.*
Z: *Raphanus sativus L.*

What we claim is:

1. A compound of the formula:

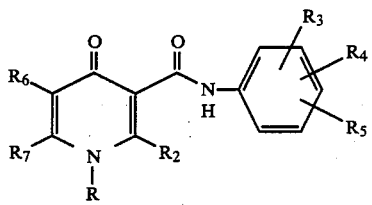

wherein:

R is a group —(CH$_2$)n—R$_1$, wherein n is an integer from 1 to 3 and R$_1$ is hydrogen, hydroxy, lower alkoxy, mercapto, lower alkylthio, amino, di-lower alkylamino, C$_{3-11}$ alkyl, lower alkenyl, lower alkynyl, C$_{3-6}$ cycloalkyl or phenyl substituted by halogen, lower alkyl or lower alkoxy;

R$_2$ and R$_7$ are different and may each be hydrogen, C$_{1-11}$ alkyl, lower alkenyl, lower alkynyl, cycloalkyl, phenyl, or phenyl substituted by halogen, lower alkyl, lower alkoxy, trihalomethyl, nitro or cyano;

R$_3$, R$_4$ and R$_5$ are, independently, hydrogen, halogen, cyano, nitro, amino, lower alkyl, lower haloalkyl, hydroxy, lower alkoxy, phenyloxy, carboxy or lower alkoxycarbonyl;

R$_6$ is hydrogen or halogen; and addition salts thereof with acids or bases.

2. The compound of claim 1, wherein

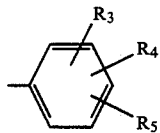

is phenyl, 2-methylphenyl, 2-chlorophenyl, 2,3-dimethylphenyl, 2,6-dimethylphenyl, 2,6-diethylphenyl, 2,6-diethyl-4-substituted (halo, cyano, nitro, amino, lower alkyl, lower haloalkyl, hydroxy, lower alkoxy, phenyloxy, carboxy or lower alkoxy carbonyl) phenyl or 2-ethyl-6-methylphenyl.

3. The compound of claim 1, wherein

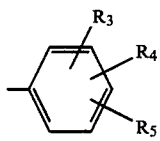

is 2-chloro-6-methylphenyl, 3-chloro-2-methylphenyl, 2-ethylphenyl, 2-3-dichlorophenyl, 2,4-dichlorophenyl, 2-5-dichlorophenyl, or 2,6-dichlorophenyl.

4. The compound of claim 1, wherein the R$_2$ alkyl, lower alkenyl or lower alkynyl group has from 2 to 5 carbon atoms.

5. The compound of claim 1, wherein R$_6$ is hydrogen or bromine.

6. The compound of claim 1, wherein R$_7$ is methyl or ethyl.

7. The compound of claim 1, wherein —(CH$_2$)$_n$—R$_1$ is methyl, ethyl, propyl, butyl, isobutyl, pentyl, isopentyl or hexyl.

8. The compound of claim 1, wherein —(CH$_2$)$_n$—R$_1$ is 2-methoxyethyl, 2-ethoxyethyl, 3-methoxypropyl or 3-ethoxypropyl.

9. The compound of claim 1, wherein —(CH$_2$)$_n$—R$_1$ is allyl or 2-propynyl.

10. The compound of claim 1, wherein —(CH$_2$)$_n$—R$_1$ is phenylmethyl, substituted phenylmethyl, 2-phenylethyl, 2-(substituted phenyl) ethyl or 3-phenylpropyl.

11. A compound of claim 1, which is
2-ethyl-1,4-dihydro-6-methyl-4-oxo-N-phenyl-1-phenylmethyl-3-pyridinecarboxamide,
2-ethyl-1,4-dihydro-6-methyl-1-(4-methylphenylmethyl)-N-phenyl-4-oxo-3-pyridinecarboxamide,
1,4-dihydro-6-methyl-4-oxo-N-phenyl-1-phenylmethyl-2-propyl-3-pyridinecarboxamide,
2-butyl-1,4-dihydro-6-methyl-4-oxo-N-phenyl-1-phenylmethyl-3-pyridinecarboxamide,
2-butyl-1,4-dihydro-6-methyl-1-(4-methylphenylmethyl)-4-oxo-N-phenyl-3-pyridinecarboxamide,
1,4-dihydro-6-methyl-2-(2-methylpropyl)-4-oxo-N-phenyl-1-phenylmethyl-3-pyridinecarboxamide,
1,4-dihydro-6-methyl-4-oxo-2-pentyl-N-phenyl-1-phenylmethyl-3-pyridinecarboxamide,
1,4-dihydro-1-(3-methoxypropyl)-6-methyl-4-oxo-N,2-diphenyl-3-pyridinecarboxamide,
1,4-dihydro-1-(2-methoxyethyl)-6-methyl-4-oxo-N,2-diphenyl-3-pyridinecarboxamide,
1,4-dihydro-6-methyl-4-oxo-N,2-diphenyl-1-phenylmethyl-3-pyridinecarboxamide,
1,4-dihydro-6-methyl-1-(4-methylphenylmethyl)-4-oxo-N,2-diphenyl-3-pyridinecarboxamide,
1-(4-chlorophenylmethyl)-1,4-dihydro-6-methyl-4-oxo-N,2-diphenyl-3-pyridinecarboxamide,
2-(3-chlorophenyl)-1,4-dihydro-6-methyl-4-oxo-N-phenyl-1-phenylmethyl-3-pyridinecarboxamide,
1,4-dihydro-6-methyl-N-(2-methylphenyl)-4-oxo-1-phenylmethyl-2-propyl-3-pyridinecarboxamide,
1-(4-chlorophenylmethyl)-1,4-dihydro-6-methyl-N-(2-methylphenyl)-4-oxo-1-propyl-3-pyridinecarboxamide, 1,4-dihydro-6-methyl-N-(2-methylphenyl)-4-oxo-2-phenyl-1-phenylmethyl-3-pyridinecarboxamide,
1-(4-chlorophenylmethyl)-1,4-dihydro-6-methyl-N-(2-methylphenyl)-4-oxo-2-phenyl-3-pyridinecarboxamide,
1,4-dihydro-6-methyl-N-(2,3-dimethylphenyl)-4-oxo-2-phenyl-1-phenylmethyl-3-pyridinecarboxamide,
1,4-dihydro-6-methyl-N-(2,6-dimethylphenyl)-4-oxo-2-phenyl-1-phenylmethyl-3-pyridinecarboxamide,
6-ethyl-1,4-dihydro-2-methyl-4-oxo-N-phenyl-1-phenylmethyl-3-pyridinecarboxamide,
6-ethyl-N-(2,6-diethylphenyl)-1,4-dihydro-2-methyl-4-oxo-1-(2-phenylethyl)-3-pyridinecarboxamide, or
5-bromo-6-ethyl-N-(2,6-diethylphenyl)-1,4-dihydro-2-methyl-4-oxo-1-(2-phenylethyl)-3-pyridinecarboxamide.
1-butyl-1,4-dihydro-6-methyl-4-oxo-N-phenyl-2-propyl-3-pyridinecarboxamide,
1-butyl-1,4-dihydro-6-methyl-4-oxo-N,2-diphenyl-3-pyridine-carboxamide,
1,4-dihydro-6-methyl-4-oxo-1-pentyl-N,2-diphenyl-3-pyridine-carboxamide,
1-hexyl-1,4-dihydro-6-methyl-4-oxo-N,2-diphenyl-3-pyridine-carboxamide,
1-butyl-1,4-dihydro-6-methyl-N-(2-methylphenyl)-4-oxo-2-phenyl-3-pyridinecarboxamide,
1-butyl-N-(2-chlorophenyl)-1,4-dihydro-6-methyl-4-oxo-2-phenyl-3-pyridinecarboxamide,
1-butyl-1,4-dihydro-6-methyl-N-(2,3-dimethylphenyl)-4-oxo-2-phenyl-3-pyridinecarboxamide,
1-butyl-1,4-dihydro-6-methyl-N-(2,6-dimethylphenyl)-4-oxo-2-phenyl-3-pyridinecarboxamide,
1-butyl-2-ethyl-N-(2,6-diethylphenyl)-1,4-dihydro-6-methyl-4-oxo-3-pyridinecarboxamide,
5-bromo-1-butyl-2-ethyl-N-(2,6-diethylphenyl)-1,4-dihydro-6-methyl-4-oxo-3-pyridinecarboxamide,
N-(2,6-diethylphenyl)-1,4-dihydro-6-methyl-1-(2-methylphenyl)-4-oxo-2-phenyl-3pyridinecarboxamide,
1-butyl-6-ethyl-N-(2,6-diethylphenyl)-1,4-dihydro-2-methyl-4-oxo-3-pyridinecarboxamide,
1-butyl-5-bromo-6-ethyl-N-(2,6-diethylphenyl)-1,4-dihydro-2-methyl-4-oxo-3-pyridinecarboxamide,
2-butyl-N-(2,6-diethylphenyl)-1,4-dihydro-1,6-dimethyl-4-oxo-3-pyridinecarboxamide,
5-bromo-2-butyl-N-(2,6-diethylphenyl)-1,4-dihydro-1,6-dimethyl-4-oxo-3-pyridinecarboxamide,
N-(4-bromo-2,6-diethylphenyl)-2-butyl-1,4-dihydro-1,6-dimethyl-4-oxo-3-pyridinecarboxamide,
5-bromo-N-(4-bromo-2,6-diethylphenyl)-2-butyl-1,4-dihydro-1,6-dimethyl-4-oxo-3-pyridinecarboxamide,
N-(4-bromo-2,6-diethylphenyl)-1,4-dihydro-1,6-dimethyl-4-oxo-2-propyl-3-pyridinecarboxamide,
5-bromo-N-(4-bromo-2,6-diethylphenyl)-1,4-dihydro-1,6-dimethyl-4-oxo-2-propyl-3-pyridinecarboxamide,
N-(2,6-diethylphenyl)-1,4-dihydro-1,6-dimethyl-4-oxo-2-propyl-3-pyridinecarboxamide,
5-bromo-N-(2,6-diethylphenyl)-1,4-dihydro-1,6-dimethyl-4-oxo-2-propyl-3-pyridinecarboxamide,
N-(2,4,6-triethylphenyl)-1,4-dihydro-1,6-dimethyl-4-oxo-2-propyl-3-pyridinecarboxamide,
5-bromo-N-(2,4,6-triethylphenyl)-1,4-dihydro-1,6-dimethyl-4-oxo-2-propyl-3-pyridinecarboxamide,
6-ethyl-N-(2,6-diethylphenyl)-1,4-dihydro-1-methyl-4-oxo-2-propyl-3-pyridinecarboxamide,
5-bromo-N-(2,4,6-triethylphenyl)-1,4-dihydro-1,6-dimethyl-4-oxo-2-propyl-3-pyridinecarboxamide,
5-bromo-6-ethyl-N-(2,6-diethylphenyl)-1,4-dihydro-1-methyl-4-oxo-2-propyl-3-pyridinecarboxamide,
N-(2,6-diethyl-4-iodophenyl)-1,4-dihydro-1,6-dimethyl-4-oxo-2-propyl-3-pyridinecarboxamide,
5-bromo-N-(2,6-diethyl-4-iodophenyl)-1,4-dihydro-1,6-dimethyl-4-oxo-2-propyl-3-pyridinecarboxamide,
N-(2,6-diethyl-4-methoxyphenyl)-1,4-dihydro-1,6-dimethyl-4-oxo-2-propyl-3-pyridinecarboxamide, or
5-bromo-N-(2,6-diethyl-4-methoxyphenyl)-1,4-dihydro-1,6-dimethyl-4-oxo-2-propyl-3-pyridinecarboxamide.

12. A plant growth inhibitor composition wherein the active component consists essentially of an effective amount of the compound of claim 1 in admixture with an inert carrier.

* * * * *